United States Patent
Niyogi et al.

(10) Patent No.: US 10,336,989 B2
(45) Date of Patent: Jul. 2, 2019

(54) ***CHLAMYDOMONAS* VIOLAXANTHIN DE-EPOXIDASE ENZYME AND ITS USES**

(71) Applicant: The Regents of the University of California, Oakland, CA (US)

(72) Inventors: Krishna K. Niyogi, Oakland, CA (US); Zhirong Li, El Cerrito, CA (US); Rachel Dent, Berkeley, CA (US); Graham Peers, Fort Collins, CO (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/625,798

(22) Filed: Jun. 16, 2017

(65) Prior Publication Data
US 2018/0057800 A1   Mar. 1, 2018

Related U.S. Application Data

(60) Provisional application No. 62/351,535, filed on Jun. 17, 2016.

(51) Int. Cl.
*C12N 15/82* (2006.01)
*C12N 9/02* (2006.01)

(52) U.S. Cl.
CPC ......... *C12N 9/0055* (2013.01); *C12N 15/825* (2013.01); *C12N 15/8269* (2013.01); *C12Y 110/99003* (2013.01)

(58) Field of Classification Search
None
See application file for complete search history.

(56) References Cited

U.S. PATENT DOCUMENTS 6,841,719 B1 *  1/2005  Yamamoto ........... C12N 9/0071
800/282

OTHER PUBLICATIONS

Merchant et al (2007, Science, 318:245-250).*
Anwaruzzaman, et al., "Genomic analysis of mutants affecting xanthophyll biosynthesis and regulation of photosynthetic light harvesting in *Chlamydomonas reinhardtii*." *Photosynth Research* 82, pp. 265-276 (2004).
Bradbury, et al., "Lycopene cyclase paralog CruP protects against reactive oxygen species in oxygenic photosynthetic organisms," *Proceedings of the National Academy of Sciences* 109, pp. E1888-E1897 (2012).I.
Maresca, et al., "Identification of a fourth family of lycopene cyclases in photosynthetic bacteria," *Proceedings of the National Academy of Sciences* 104, pp. 11784-11789 (2007).
Merchant, et al., "The Chlamydomonas genome reveals the evolution of key animal and plant functions," *Science* 318 (5848), pp. 245-250 (2007) GenBank Accession No. PNW84115.
Niyogi, et al., "Chlamydomonas xanthophyll cycle mutants identified by video imaging of chlorophyll fluorescence quenching," *The Plant Cell* 9, pp. 1369-1380 (1997).
Niyogi, et al., "*Arabidopsis* mutants define a central role for the xanthophyll cycle in the regulation of photosynthetic energy conversion," *The Plant Cell* 10, pp. 1121-1134 (1998).

* cited by examiner

*Primary Examiner* — Jason Deveau Rosen
(74) *Attorney, Agent, or Firm* — Kilpatrick Townsend & Stockton LLP

(57) ABSTRACT

This disclosure provides *Chlamydomonas* violaxanthin de-epoxidase (CVDE) gene, polypeptides, and variants thereof as well as host cells that are genetically modified to express a CVDE polypeptide or variant. The disclosure additionally provides methods of producing such a genetically modified host cell and methods of using the cells, e.g., to increase zeaxanthin production.

20 Claims, 17 Drawing Sheets

Specification includes a Sequence Listing.

Xanthophyll cycle

Figure 8a

```
SynCruA     1  LKVFAWASGFPQPQSLCRQLKSDLEQAFPNQYPAPPEIQPGQSIFDALAA
CrCVDE      1  ------------------------------------SAGKRFDSLAA
VocarCVDE   1  ------------------------------------STPPTQSASAA
OsttaCruP   1  ------------------------------------RTIEIMESIAS
SynCruP     1  ---------------------------------------------MGQ
CrCruP      1  ------------------------------------REGIRQRSVAA
VocarCruP   1  -------------------------------------------------
PhysCruP    1  ------------------------------------RTQRIMENTPG
AtCruP      1  ------------------------------------LTQKIMESISV SynCruA    51  D------YPKTVEYFQKFPQGEFDLQRAIWEKRWRETVKNPQAPQPVIF
CrCVDE     12  YGLARDVLTKQASNIEGNPIEFIDVTEKFWRALRNQKHEPEKKGPKVVTY
VocarCVDE  12  PGLARTILA--QPGIEGDPLAFLEVSEAIWRALRNQKHDPERKGPSVVTR
OsttaCruP  12  ARDD-DDASAARGAGGTTTLEGLMRLDAAWTSMRRGAGRGD--GEAFARR
SynCruP     4  --------VKTILGAMPGDPLKGLRAADQRWQNWRQGKIGAPA-MVQIG--
CrCruP     12  -------NAQAAGAGGRTTYAAFKAADEQWLKLRTQPEGEAA--GPAPQ-
VocarCruP   1  -----------------------------------GTPS-GPAAPK-
PhysCruP   12  --------SAEAGGAGGAMSYQALKRLDEHWRKLEKARTPMTGP-APEVVTR
AtCruP     12  --------GGEAGGAGGAYSYNALKRLDNIWSNICTQPTGPQE-TQQIVSR SynCruA    95  --------------EKNQPADEQFAQTDLVVIGGALGVIHAAVMARLGYKV
CrCVDE     62  ADELLFPDSASSSSASTSSPHPDIDVVICGGTLGLFLATALQLQGWRV
VocarCVDE  60  ADLGPLPTPPRPSSHAAAGLRQQHDFDVVICGGTLGLPLATALQLRGWRV
OsttaCruP  59  R-----------RRRHATETASDAFDVAVCGGTLGILVACALQRRCGRV
SynCruP    44  ------------------TEDCPDYDCDVLVCGGTLGLLLAAALQRRGWRV
CrCruP     52  ---PV------TESAQPLEAAPQIDVVVCGGTLGIFAAAALAARGLRV
VocarCruP  11  ---PI------SESSEPLQTSPEFDVVVCGGTLGIFAAAAILARGLRV
PhysCruP   54  RQGKW--------ADSGLADRSQAVFDVVVCGGTLGVFLATALARGLKV
AtCruP     54  VSGFS--------QDYSMGNNLVGTFDIVVCGGTLGIFLATALCAKGLRV SynCruA   132  LLIDRLPFGRMNREWNISRSELQSLINLGLFDETDIETLVARDYKNGFNK
CrCVDE    112  AIVEKRLVQGRNQEWNISWGELEVLVELGLLSEEBLKGCVISEFNPIRVC
VocarCVDE 110  AIVEKRLVQGRNQEWNISWGELEVLVELGLLSRTELREAVVSEFNPIRVC
OsttaCruP  97  CVIERGELRGREQEWNVSRAELEALVRACALTAEDADEVTMIELNPIRCG
SynCruP    77  ILLERGPLQGRVQEWNISRSELQTLLDLELLSETELREVIATEFNPURIQ
CrCruP     91  AVVERGPLRGRAQEWNISRKELYELEHVGVASREELEACVAIEFNPVRIG
VocarCruP  50  AVLERGPLRGRAQEWNISRKELLELESVGVATREELEACVAIEVRKL---
PhysCruP   96  AILERGPLRGRVQDWNVSRKELKELVYAGVLTEDEIEEVISLETNPSRVC
AtCruP     96  AVVERNAIKGRDQEWNISRKEMKELTSVRVLTEDEIEEVIAAKTNPNRCG SynCruA   182  PFDGNNP---------SHLKANILYTPTVLNIAVASELHLEKCGEKLRA
CrCVDE    162  P---------------KGGEDIVTQDVLNLGVHPRTILDSLKRRFHA
VocarCVDE 160  P---------------QGGQDMWTSDVLNLGVQPRRILEALRRRFTA
OsttaCruP 147  PH--------------GSEKEDIVTRDVLNCGVSPARLVAKCRERFEE
SynCruP   127  P---------------HGGDPLWVKDILNIGVSPRRILAVLKEKFLT
CrCruP    141  PAWDLSPATFSAASSASTSSRLTEVWTRDVLNLGVRPDALVQLMRAKLEE
VocarCruP  97  ---------------CSISGLSEVWTRDILNLGVSPNAIVGLMRRKLEE
PhysCruP  146  P---------------AGGTELWVNDILNLGVSPAKLIEVCKKRFVD
AtCruP    146  P---------------ENLGDIWVEDILNLGVSPAKLVETVKQRFIS
```

Figure 8b

```
SynCruA     222  AGGEIWDQKEFIRADIGRERAQIFTKSL-----------------
CrCVDE      194  AGGIIFENTAFKHADVHEDGIRLSLAPGGAAAPVAVGDTNRPNGLTTGGA
VocarCVDE   192  AGGAVYENTAFRAATINSDCLLENLSPGGSAQDLAVGDTNRPNGLDAASA
OsttaCruP   181  AGGRVMGRASLNGVDVYDDCAVLDV------------------------
SynCruP     159  WGGKIFENHPCTGITVSPQGAIART-----------------------
CrCruP      191  LGGAVLEQARLAGISVHPFGPSEPSATDSGA------------------
VocarCruP   131  QGCVVLERTALEGVAARRD--------DDD-------------------
PhysCruP    178  VGGEVLEFTGLSKLDVFNDGAVVSLD-----------------------
AtCruP      178  LGGVILEDSSLSSIVIYNDLAVMQLS-----------------------

SynCruA     250  --------VTGDEKIVQARLLMDAMGTASFAAQLNQGRPFDSVCPTVGAV
CrCVDE      244  A--PAPSGPVAPRSMTTRLLLDCMGHVSDIVKQIRGRVKPDGVVLVVGCC
VocarCVDE   242  SSSRAEPSPEPFRTLTCRLLLDCMGHVSDIVKQIRCRVKPDGVCVVGSC
OsttaCruP   206  ---------DCNAVHARLVLDCMGFNSPIVRQIRGGAKPDGVCVVGTC
SynCruP     184  ---------EKFQFHTRLILDCMGHFSPIAQQVRGQKPDGVCLVVGSC
CrCruP      222  ------GAGARAARLTARLVVDCMGHFSPIVRQVRWGTKPDGVCLVVCTC
VocarCruP   153  ------DGSPAAATVTARLVVDCMGHFSPIVRQVRRGALKPDGVCLVVGTM
PhysCruP    204  ---------NCATLVGRLLLDVNGNQSPIVRQIRWGQHPDGVCLVVGAC
AtCruP      204  ---------KGDTLESRLVIDAMGNFSPILKQIKRGRKPDGVCLVVGSC SynCruA     293  VKGFDFAVWDSEYGDVLNSHGDESR------GRQLIWELFPGQGD--EME
CrCVDE      292  AEGFPAEANI--SADLLYGLSHARD------DVQLFWEAFPAEGC-QART
VocarCVDE   292  AEGFPEDRNQ--SADLLYSLSHARH------DLQLFWEAFPAEGC-AART
OsttaCruP   246  AEGFDASKME--SADLIRTVDDET----DYRGQYFWEAFPASSGPGDRT
SynCruP     224  AQGFA--ANS--KGDLIYSFTPIIN------QCQYFWEAFPAHDC---RT
CrCruP      266  GSGFAEGNNT--TADVILTNTPLQPAEAAFNRAQYFWEAFPASSGPSDRT
VocarCruP   197  GSGFT--MNT--TADVILTSTPLQPEDA---KAQYFWEAFPASGPTDRT
PhysCruP    244  ARGFE--MNS--TSDLIVTNLQVTQ--VGSSKTQYFWEAFPACSGPTDRT
AtCruP      244  AHGFK--ENS--SSDVLISSSSVTR--VADSNVQLFWEAFPASGPLDRT SynCruA     335  IVLPHTHEVNFENPGSILEMYEDFFSILPFYRRCD-MAQLTFEKATFGYI
CrCVDE      333  TYMFAYSDAHPDRP-SFEALLDTFQMLPEYQCIP-LDQLKFKRVLFGGF
VocarCVDE   333  TYMFAYSDAHPDRP-TFEQLLATYPEMLPYQGVS-LDQLRFKRVLFGGF
OsttaCruP   290  TIMFTLMDAEEARP-SIASMLEDYWEYMPAYQGLSSMDDVKVKRVLFGLF
SynCruP     261  TILFTYLDAHPQLF-DLAFILESVLKLLPDYCQVD-LAALDFQRFLFGFF
CrCruP      314  TIMFTYIDAALYQK-PLAAMMEDYINRLMPQYQGVR-LEDITFKRVLFGFF
VocarCruP   240  TMFTYILTADDYRP-PLAAMMEDYWRLMPQYQGVR-LEDITFKRVLFGMF
PhysCruP    288  TYMFSYILDATESRP-LLEEMLEDYWDLMPQYQGVK-LEDLEIRRVLFGCF
AtCruP      288  TIMFTITEPQSTSE-SLEDLLETYWRLMPRYQGVS-LDDLEILRVVYGIL SynCruA     384  PGIFNVGAGDRQVAFDRLLAIGDAASLQSPLVFTGFGSLVRNLDRLTKLE
CrCVDE      381  PCYSN---GPLAPAFDRVLQIGDASAAQSPLSFGGFGSMMRHIPRLARGL
VocarCVDE   381  PCYNN---GPLPPAFDRVLQIGDASASQSPLSFGGFGSMMRHLGRLTRGL
OsttaCruP   339  PLFRN---SPLKTEIDRVLAIGDASGIQSPLSFGGLAALRHVNRITGAV
SynCruP     309  PSLRR---SPLHYPWDRTLPIGDSSGGQSPVSFGGFGALRHLERLTNGL
CrCruP      362  PTFKD---TPLRPAFDRLIQIGDASGLQSPLSFGGFCALTRHLARLTNAL
VocarCruP   288  PTFKD---TPLRPAFDRVLQIGDASGLQSPLSFGGFGALTRHLARLTAAL
PhysCruP    336  PTYRA---SPLFSAFDRVLQIGDASGIQSPISFGGFGALTRHIGRLSNGL
AtCruP      336  PTFRN---SPLPAAFDRVLQFGDASGIQSPVSFGGFCSLTRHLGRLSNGT
```

Figure 8c

```
SynCruA    434  DIALQKDLLDQQNLSKIRALQSNIAVIWLFSKGMMVPTGMKL---------
CrCVDE     428  DQALQEDRLAHPDLNWLHPYQPSLSASWLFQRSMSLAVGQVALPPDCPHA
VocarCVDE  428  NQALAEDRLHQKDLAWLQPYQPSLSASWLFQRSMSFCVGQVSYPSSYPYT
OsttaCruP  386  EEALDANALDRDALRSINAVQPALSAAWLFQRCMSVRIGAKP---------
SynCruP    356  DDALTQDCCDRQSLAQLQPYQPNLSVTWLFQKAMSVGVNQSC---------
CrCruP     409  TELAEADALDRNSLGLIHAUNPGLSSWMMQKAMSVREGDKP---------
VocarCruP  335  TEAVEADALDRGSLSLVQSYKPGLSSSWMMQKAMSVRRGEQP---------
PhysCruP   383  YDALQADLLDKNNLALLNPYLPNLSGVMYQRAMSVRLDIES---------
AtCruP     383  YDAIDGDLLDSDSLSKLNPYMPNLSASWLFQRAMSAKQQLDV---------

SynCruA    476  --------------------------------------------------
CrCVDE     478  PAYYAAAKEAKAFAAAAAVDRAEGFDGLVST---AGERALSLQEAAMEAV
VocarCVDE  478  PPYCTTDVTLPPAL---ATDSTESFSDTASAVLVMCA-GAGPAAAFQEAV
OsttaCruP  428  --------------------------------------------------
SynCruP    398  --------------------------------------------------
CrCruP     451  --------------------------------------------------
VocarCruP  377  --------------------------------------------------
PhysCruP   425  --------------------------------------------------
AtCruP     425  --------------------------------------------------

SynCruA    476  --------------------------------------------------
CrCVDE     525  EAVAARFAAGSADPADYFHVEQEVPGAGSDRRT--------PQE---ASG
VocarCVDE  524  AMAAARFAAGAADPADYFHEEPDQDMGAAAAAAAAATTAAATKLAAAATT
OsttaCruP  428  --------------------------------------------------
SynCruP    398  --------------------------------------------------
CrCruP     451  --------------------------------------------------
VocarCruP  377  --------------------------------------------------
PhysCruP   425  --------------------------------------------------
AtCruP     425  --------------------------------------------------

SynCruA    476  --------------------PPQRLNAMLNTPLGLIADSSPEV
CrCVDE     564  KAQPAPPKLKKKLFERDFRTAPEWQRLPYTHVNEILGTNFGVMGVLGDRV
VocarCVDE  574  TTTSQRQQQPRTLFERDFRRGPTWLRLPYTHVNEILGCNFGVMGILGDRV
OsttaCruP  428  --------------------KRDFINRLMTNFGVMEALGEDV
SynCruP    398  --------------------PPNQINDLLNAVFGVMAQLGEDT
CrCruP     451  --------------------PPELINRMLAGNFRAMEKLGEAT
VocarCruP  377  --------------------PPDLINRMLAGNFKAMERLGDPV
PhysCruP   425  --------------------PPDFINNLISINFECMERLGDPV
AtCruP     425  --------------------SRGFTNELLHVNFSCMQRLGDPV SynCruA    499  AETFIKDRTSWLMFNKLALVAARQNPALLVWIWQMAGAKDFIRWVGAYFA
CrCVDE     614  LKPFLQDTIQLVPLSLSMTGMMLSNPVTVSRVLMQVGPKTLVSWFAHYFA
VocarCVDE  624  LRPFLQDTIQLVPLSLSMMGMMLANPVTVSRVLLQVGPRTLVGMFAHIAA
OsttaCruP  451  MRPFLQDVVTFKGLGKTLVSMTASKPLFVPELLINAGPGPIADWFRHFIA
SynCruP    421  LNPFLQDVVQFQGLTKTLPRVNFK---TVLPILPHLCVCALADWLRHYLA
CrCruP     474  MKPFLQDVIQFQPMLATMGAQILTGPLSVPSLMAHVGPCPLAEWLGHMAN
VocarCruP  400  MKPFLQDVVQFQGPMMRLMAAQILTDPASIPSLIRHVGPAPLLEWLSHMAN
PhysCruP   448  VRPFLQDVVQFWPQVRLLSLIMLKPLFIPQIFRQVGFFPLIDWFRHFIA
AtCruP     448  LRPFLQDTIQPGPLAKTLGLVMLTKPQIIPSIFRQVGIPVLLDWSVHFFM
```

Figure 8d

```
SynCruA    549  FSFDAVESLLMGWLPQ-----W---------------LENSEAWLSEKY
CrCVDE     664  LVAVSLGHVLLSPL-------------------RGV--VPSYSFQRM
VocarCVDE  674  LVAYSIAYLVLRPL-------------------RQL--VPYYAFQRL
OsttaCruP  501  LCMLDLLSSPAGAVAHALRPAGQDESNANPLVEAVSGSLSPRQKGFIKTH
SynCruP    468  LCLKTSSYAL-------------------------SQRLPMGDSYQAKRR
CrCruP     524  LGAYTALHGAAGAAGLRA--------------ALAPGGAAAGLPAHARFALGRL
VocarCruP  450  LAAYIALHGAASMADLRT--------------AVSG---AAVLTPRERFALNRL
PhysCruP   498  LAMLTLWLALSG-------------------SPRTWVNSLPKEKQLVWKGR
AtCruP     498  LCLTTLISAYIDP-------------------LLRPSLEGLPSKTRFEWRRC SynCruA    579  PSLQLSLLSLKFRETVGL---------------------
CrCVDE     690  LDALEYGSGSDYRYHPAGPLLGAAVSA-----GRGAPVAALSAARSI
VocarCVDE  700  LDALEYGSGSDYRYHGPMSLAAGPEGASSAVAGSQGAAAA-AAAAATAA
OsttaCruP  551  AEAVILGCGRDAR------------------------
SynCruP    493  REAYQYGSGQDFHQAGLLEQD-----------------
CrCruP     564  LDAWEYGSGKDYKL-------------------------
VocarCruP  487  LDAWEYGSGMDYKL-------------------------
PhysCruP   531  FEAWQYGSGLDIHP------------------------
AtCruP     531  LEAWKYGAGLDYEL------------------------

SynCruA         -------------------------------------
CrCVDE     735  DGGAAT-ESLDGGDGGDAAGEAGAAGKSEGGSVKGRKAPKQQQ-PAEPM
VocarCVDE  749  EGALAVRQQMPTSPSPKENGATNSDGDGDG---PGLDVLRGVDSSVAVPM
OsttaCruP       -------------------------------------
SynCruP         -------------------------------------
CrCruP          -------------------------------------
VocarCruP       -------------------------------------
PhysCruP        -------------------------------------
AtCruP          -------------------------------------

SynCruA         -------------------------------------
CrCVDE     783  PIPVPV----AAATAAAAAMAAATMVVGLPGIGPVTLG
VocarCVDE  796  SAAVHTPTVTAGAAVAAAAAAAPHLEGESRT------
OsttaCruP       -------------------------------------
SynCruP         -------------------------------------
CrCruP          -------------------------------------
VocarCruP       -------------------------------------
PhysCruP        -------------------------------------
AtCruP          -------------------------------------
```

CHLAMYDOMONAS VIOLAXANTHIN DE-EPOXIDASE ENZYME AND ITS USES

CROSS-REFERENCE TO RELATED APPLICATIONS

This application claims priority to U.S. Provisional Application No. 62/351,535, filed Jun. 17, 2016, which is herein incorporated by reference for all purposes.

STATEMENT AS TO RIGHT TO INVENTIONS MADE UNDER FEDERALLY SPONSORED RESEARCH AND DEVELOPMENT

This invention was made with government support under Contract No. DE-AC02-05CH11231 awarded by the U.S. Department of Energy. The government has certain rights in this invention.

REFERENCE TO A "SEQUENCE LISTING" SUBMITTED AS ASCII TEXT FILES VIA EFS-WEB

The Sequence Listing written in file 077429-014110US-1052076_SequenceListing.txt created on Aug. 31, 2017, 92,241 bytes, machine format IBM-PC, MS-Windows operating system, in accordance with 37 C.F.R. §§ 1.821- to 1.825, is hereby incorporated by reference in its entirety for all purposes.

BACKGROUND OF THE INVENTION

Plants, algae and cyanobacteria need to regulate photosynthetic light harvesting in response to the constantly changing light environment. Rapid adjustments are required to maintain fitness because of a tradeoff between efficient solar energy conversion and photoprotection. Photosynthetic organisms are subjected to a large dynamic range of light intensities, which can vary rapidly due to canopy shading, passing clouds, or sunflecks, as well as on a daily or seasonal basis. To allow optimal photosynthesis at low light intensities and to avoid photo-oxidative damage due to the formation of reactive oxygen species (ROS) under excess light, photosynthetic organisms have evolved the ability to regulate light harvesting. Under excess light, photosynthetic light harvesting is regulated by nonphotochemical quenching (NPQ) mechanisms that are responsible for dissipating excess absorbed light as heat[4-7]. The major and most intensively investigated component of NPQ is called qE, which is turned on and off on the time scale of seconds to minutes. qE depends on acidification of the thylakoid lumen upon formation of high ΔpH across the thylakoid membrane in excess light[8]. In plants, this results in two important changes that facilitate qE: conformational changes of light-harvesting complex proteins by protonation and the activation of a lumen-localized violaxanthin (Vio) de-epoxidase (VDE) enzyme. VDE catalyzes the conversion of Vio to zeaxanthin (Zea) via the intermediate antheraxanthin (Anthera). Zea and Anthera (xanthophylls with a de-epoxidized 3-hydroxy β-ring end group) are the major xanthophyll pigments that are involved in qE in plants. Zea epoxidase converts Zea back to Vio in limiting light. Together, these light intensity-dependent interconversions are known as the xanthophyll cycle (FIG. 1a).

The xanthophyll cycle is ubiquitous among green algae and plants and as explained above, is necessary for the regulation of light harvesting, protection from oxidative stress, and adaptation to different light conditions[1,2]. VDE is the key enzyme responsible for zeaxanthin synthesis from violaxanthin under excess light.

Mutants defective in the xanthophyll cycle and qE have been identified in the unicellular green alga *Chlamydomonas reinhardtii* and the model plant *Arabidopsis thaliana*[9,10]. The npq1 mutants are defective in VDE activity and are unable to convert Vio to Anthera and Zea in high light (FIGS. 1a and d). Although the *Arabidopsis* npq1 mutant was shown to affect the VDE gene[10], the molecular basis of the *Chlamydomonas* npq1 mutant has been mysterious, because the *Chlamydomonas* genome lacks an obvious ortholog of the VDE gene found in plants and other algae.

BRIEF SUMMARY OF CERTAIN ASPECTS OF THE DISCLOSURE

This disclosure is based, in part, on the discovery that the CVDE gene from the green alga *Chlamydomonas reinhardtii* encodes an atypical VDE. This protein is not homologous to the VDE found in plants and is instead related to a lycopene cyclase from photosynthetic bacteria[3]. Unlike the plant-type VDE that is located in the thylakoid lumen, the *Chlamydomonas* CVDE protein is located on the stromal side of the thylakoid membrane. Phylogenetic analysis suggests that CVDE evolved from an ancient de-epoxidase that was present in the common ancestor of green algae and plants, providing evidence of unexpected diversity in photoprotection in the green lineage. The CVDE enzyme can be overexpressed in a plant or photosynthetic organism to speed up the kinetics of non-photochemical quenching (NPQ) and further, may be overexpressed to increase the production of zeaxanthin in algae and plants relative to a counterpart plant of the same strain that does not overexpress the CVDE enzyme.

This disclosure thus provides methods and compositions to overexpress *Chlamydomonas* CVDE protein in photosynthetic organism such as green algae and in plants. In some embodiments, green algae are genetically modified to overexpress *Chlamydomonas* CVDE relative to a wildtype strain of green algae. Examples of green algae include *Chlamydomonas reinhardtii; Dunaliella salina; Chlorella fusca; Chlorella vulgaris; Scenedesmus obliquus; Botryococcus braunii*. In some embodiments, plants are genetically modified to overexpress *Chlamydomonas* CVDE protein. In some embodiments, the photosynthetic organism is a plant. The plant may be a monocotyledonous plant or a dicotyledonous plant. In certain embodiments of the invention, the plant is corn, switchgrass, sorghum, miscanthus, sugarcane, poplar, alfalfa, pine, wheat, rice, soy, cotton, barley, turf grass, tobacco, potato, bamboo, rape, sugar beet, sunflower, willow, eucalyptus, millet, or any other plant or moss. In some embodiments, the photosynthetic organism is a diatom, a golden-brown algae (Chrysophyta), a fire algae (Pyrrophyta), a brown algae (Phaeophyta), a yellow-green algae (Xanthophyta), or a eustigmatophyte (e.g., a Nannochloropsis sp).

BRIEF DESCRIPTION OF THE FIGURES

FIG. 1a, Xanthophyll cycle reactions. The de-epoxidation of violaxanthin to zeaxanthin via antheraxanthin is defective in the npq1 mutant. FIG. 1b, Schematic showing the Cre04.g221550 (CrCVDE) gene model and the 164-bp deletion in the npq1 mutant allele. FIG. 1c, Phylogenetic analysis of CVDE and CruP proteins. Syn, *Synechococcus* sp. strain PCC7002; Phys, *Physcomitrella patens;* At, *Arabidopsis thaliana;* Ostta, *Ostreococcus tauri;* Cr, *Chlamydomonas reinhardtii;* Vocar, *Volvox carteri. * FIG. 1*d*, HPLC phenotype of wild type, npq1, and two independent complemented lines. Arrows denote the Zea peak resulting from CVDE activity.

FIG. 2*a*, Constructs used for transformation of the *Arabidopsis* vde1 mutant and their ability to complement the zeaxanthin accumulation and NPQ phenotypes. "+" indicates successful rescue of the phenotype. FIG. 2*b*, HPLC phenotypes of wild type, vde1 mutant, and two complemented lines. Arrows denote the Zea peak resulting from CVDE activity (or plant-type VDE activity in the wild type). FIG. 2*c*, NPQ induction and relaxation of wild type, vde1 mutant, and two independent complemented lines. White bar above graph indicates illumination with 1250 µmol photons $m^{-2}$ $sec^{-1}$; black bar indicates darkness (with only very weak measuring light).

FIG. 3*a*, Immunoblot analysis of total cell (T), membrane (M), and soluble (S) fractions of *Chlamydomonas* strains. The FLAG-tagged CrCVDE protein is detected in the membrane fraction and not in the soluble fraction in two independent transformants. Subcellular markers: D2 for membrane fraction and RbcL for soluble fraction. FIG. 3*b*, Protease protection assay of isolated intact thylakoids from *Chlamydomonas* complemented lines. Isolated thylakoids were treated with thermolysin in the presence and absence of Triton X-100. Aliquots were removed at the specified times, samples were separated by SDS-PAGE, and immunodetection was performed with specified antibodies. Thermolysin-resistant Atpβ was used as a loading control. The FLAG-tagged CrCVDE protein was probed with both the N-terminal epitope antibody and the C-terminal FLAG antibody. Subcellular markers: PsaD for stroma-exposed membrane protein, PsbO for thylakoid lumen. FIG. 3*c*, Immunoblot analysis and protease protection assay of the FLAG-tagged CrCVDE protein expressed in the *Arabidopsis* vde1 mutant. Left section of panel c: the CrCVDE protein is detected in the thylakoid membrane fraction and not in the soluble stroma fraction in *Arabidopsis*. Subcellular markers: PsaD for stroma-exposed membrane protein, PsbO for thylakoid lumen, and RbcL for stroma. Right section of FIG. 3*c*: protease protection assay of isolated thylakoids from *Arabidopsis* complemented lines. RbcL was not present in the thylakoid fraction. Lower section of FIG. 3*c*: the location of the plant-type VDE in the thylakoid lumen was confirmed by analysis of a transformant expressing the FLAG-tagged *Arabidopsis* VDE protein in the vde1 mutant. The migration of the VDE protein in the chloroplast fraction is altered by the comigration of a protein that is absent from the thylakoid fraction. FIG. 3*d*, Proposed topology of CrCVDE in both *Chlamydomonas* and *Arabidopsis*.

FIG. 8*a*-8*d*. Alignment used for phylogenetic analysis. Syn, *Synechococcus* sp. strain PCC7002 (SynCruA=SEQ ID NO:9, SynCruP=SEQ ID NO:13); Cr, *Chlamydomonas reinhardtii* (CrCVDE=SEQ ID NO:10, CrCruP=SEQ ID NO:14); Vocar, *Volvox carteri* (VocarCVDE=SEQ ID NO:11, VocarCruP=SEQ ID NO:15); Ostta, *Ostreococcus tauri* (OsttaCruP=SEQ ID NO:12); Phys, *Physcomitrella patens* (PhysCruP=SEQ ID NO:16); At, *Arabidopsis thaliana* (AtCruP=SEQ ID NO:17).

FIG. 10*a*, NPQ induction curve of tobacco leaf spots transformed with CrCVDE and control. NPQ was induced by illumination with 990 µmol photons $m^{-2}$ $sec^{-1}$. Error bars represent standard deviation (n=4). FIG. 10*b*, False-colored image of NPQ of tobacco leaf spots transformed with CrCVDE and control after 60 sec of high light exposure. FIG. 10*c*, Immunoblot analysis of leaf spots transformed with CrCVDE and control. The CrCVDE protein was probed with the specific N-terminal peptide antibody. Rubisco was used as a loading control.

DETAILED DESCRIPTION OF THE DISCLOSURE

Terminology

Figure 1A:
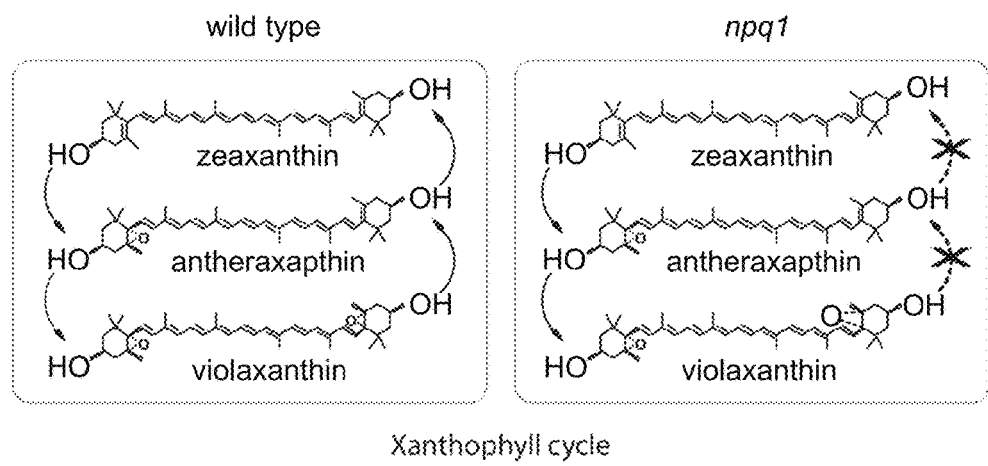
FIGS. 1a-1d. Molecular analysis and complementation of npq1 mutation in *Chlamydomonas*.
Figure 1B:
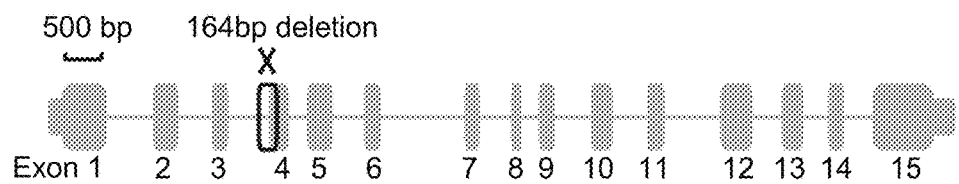

The term "naturally-occurring" or "native" as used herein as applied to a nucleic acid, a protein, a cell, or an organism, refers to a nucleic acid, protein, cell, or organism that is found in nature. For example, a polypeptide or polynucleotide sequence that is present in an organism that can be isolated from a source in nature and which has not been intentionally modified by a human in the laboratory is naturally occurring.

The term "heterologous nucleic acid," as used herein, refers to a nucleic acid wherein at least one of the following is true: (a) the nucleic acid is foreign ("exogenous") to (i.e., not naturally found in) a given host microorganism or host cell; (b) the nucleic acid comprises a nucleotide sequence that is naturally found in (e.g., is "endogenous to") a given host microorganism or host cell (e.g., the nucleic acid comprises a nucleotide sequence endogenous to the host microorganism or host cell. In some embodiments, a "heterologous" nucleic acid may comprise a nucleotide sequence that differs in sequence from the endogenous nucleotide sequence but encodes the same protein (having the same amino acid sequence) as found endogenously; or two or more nucleotide sequences that are not found in the same relationship to each other in nature, e.g., the nucleic acid is recombinant. An example of a heterologous nucleic acid is a nucleotide sequence encoding a fusion protein comprising two proteins that are not joined to one another in nature.

The term "recombinant" polynucleotide or nucleic acid refers to one that is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. A "recombinant" protein is encoded by a recombinant polynucleotide. In the context of a genetically modified host cell, a "recombinant" host cell refers to both the original cell and its progeny.

As used herein, the term "genetically modified" refers to any change in the endogenous genome of a cell from a photosynthetic organism, e.g., a plant or green algae cell, compared to a wild-type cell. Thus, changes that are introduced through recombinant DNA technology and/or classical mutagenesis techniques are both encompassed by this term. The changes may involve protein coding sequences or non-protein coding sequences such as regulatory sequences as promoters or enhancers.

An "expression construct" or "expression cassette" as used herein refers to a recombinant nucleic acid construct, which, when introduced into a host cell in accordance with the present disclosure, results in increased expression of a protein encoded by the nucleic acid construct. The expression construct may comprise a promoter sequence operably linked to a nucleic acid sequence encoding the protein or the expression cassette may comprise the nucleic acid sequence encoding the protein where the construct is configured to be inserted into a location in a genome such that a promoter endogenous to the host cell is employed to drive expression of the fusion protein.

By "construct" is meant a recombinant nucleic acid, generally recombinant DNA, which has been generated for the purpose of the expression of a specific nucleotide sequence(s), or is to be used in the construction of other recombinant nucleotide sequences.

As used herein, the term "exogenous protein" refers to a protein that is not normally or naturally found in and/or produced by a given organism or cell in nature. As used herein, the term "endogenous protein" refers to a protein that is normally found in and/or produced by a given organism or cell in nature.

An "endogenous" protein or "endogenous" nucleic acid" is also referred to as a "native" protein or nucleic acid that is found in a cell or organism in nature.

A polynucleotide sequence is "heterologous to" a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from any naturally occurring allelic variants.

The terms "increased expression" and "overexpression" of a CVDE polypeptide are used interchangeably herein to refer to an increase in the amount of polypeptide in a genetically modified cell, e.g., a cell into which an expression construct encoding a CVDE polypeptide has been introduced, compared to the amount of CVDE polypeptide in a counterpart cell that does not have the genetic modification, i.e., a cell of the same strain or organism without the modification, such as a wildtype host cell. An increased level of expression for purposes of this application is at least 5%, or at least 10%, 20%, 30%, 40%, 50%, 60%, 70%, 80%, 90%, 100%, or greater, compared to the counterpart unmodified cell. The unmodified counterpart cell need not express the CVDE polypeptide. Thus, the term "overexpression" also includes embodiments in which a CVDE polypeptide is expressed in a host cell that does not natively express the polypeptide. Increased expression can be assessed by any number of assays, including, but not limited to, measuring the level of RNA transcribed from the CVDE gene, the level of CVDE polypeptide, and/or the level of polypeptide activity. Illustrative assays are provided in the Examples section. "Overexpression" in the context of protein activity includes overexpression relative to enodogenous VDE activity such that the overall level of VDE in the host cell is increased in the genetically modified host cell.

The term "plant" includes whole plants, shoot vegetative organs and/or structures (e.g., leaves, stems and tubers), roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, plant tissue (e.g., vascular tissue, ground tissue, and the like), cells (e.g., guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid, and hemizygous.

One of skill will recognize that individual substitutions, in a nucleic acid, peptide, polypeptide, or protein sequence that alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Examples of amino acid groups defined in this manner can include: a "charged/polar group" including Glu (Glutamic acid or E), Asp (Aspartic acid or D), Asn (Asparagine or N), Gln (Glutamine or Q), Lys (Lysine or K), Arg (Arginine or R) and His (Histidine or H); an "aromatic or cyclic group" including Pro (Proline or P), Phe (Phenylalanine or F), Tyr (Tyrosine or Y) and Trp (Tryptophan or W); and an "aliphatic group" including Gly (Glycine or G), Ala (Alanine or A), Val (Valine or V), Leu (Leucine or L), Ile (Isoleucine or I), Met (Methionine or M), Ser (Serine or S), Thr (Threonine or T) and Cys (Cysteine or C). Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His and Trp; and the "phenyl sub-group" comprising Phe and Tyr. In another further example, the aliphatic group can be sub-divided into sub-groups including: the "large aliphatic non-polar sub-group" comprising Val, Leu and Ile; the "aliphatic slightly-polar sub-group" comprising Met, Ser, Thr and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained.

The terms "nucleic acid" and "polynucleotide" are used synonymously and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones. Thus, nucleic acids or polynucleotides may also include modified nucleotides, that permit correct read through by a polymerase. "Polynucleotide sequence" or "nucleic acid sequence" may include both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses conservatively modified variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc The term "promoter" or "regulatory element" refers to a region or sequence determinants located upstream or downstream from the start of transcription that are involved in recognition and binding of RNA polymerase and other proteins to initiate transcription. A "plant promoter" is a promoter capable of initiating transcription in plant cells. Such promoters need not be of plant origin, for example, promoters derived from bacteria bacteria or plant viruses, can be used in the present invention.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Optimal alignment of sequences for comparison may be conducted by the local homology algorithm of Smith and Waterman Add. APL. Math. 2:482 (1981), by the homology alignment algorithm of Needle man and Wunsch J. Mol. Biol. 48:443 (1970), by the search for similarity method of Pearson and Lipman Proc. Natl. Acad. Sci. (U.S.A.) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" in the context of polynucleotide or polypeptide sequences means that a polynucleotide or polypeptide comprises a sequence that has at least 50% sequence identity to a reference nucleic acid or polypeptide sequence. Alternatively, percent identity can be any integer from 40% to 100%. Exemplary embodiments include at least: 50%, 55%, 60%, 65%, 70%, 75%, 80%, 85%, 90%, 95%, or 99% compared to a reference sequence using the programs described herein; preferably BLAST using standard parameters, as described below.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C.

The term "isolated", when applied to a nucleic acid or protein, denotes that the nucleic acid or protein is essentially free of other cellular components with which it is associated in the natural state. It is preferably in a homogeneous state and may be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest.

DETAILED DESCRIPTION OF ASPECTS OF THE DISCLOSURE

The disclosure employs various routine recombinant nucleic acid techniques. Generally, the nomenclature and the laboratory procedures in recombinant DNA technology described below are those commonly employed in the art. Many manuals that provide direction for performing recombinant DNA manipulations are available, e.g., Molecular Cloning, A Laboratory Manual. (Sambrook, J. and Russell, D., eds.), CSHL Press, New York (3rd Ed, 2001); and Current Protocols in Molecular Biology. (Ausubel et al., eds.), New Jersey (1994-1999).

In one aspect, the disclosure is based, in part, on the discovery of a new VDE enzyme in green algae.

CVDE nucleic acid and polypeptide sequences suitable for use in the invention include nucleic acid sequences that encode a CVDE polypeptide of SEQ ID NO:1 or a substantially identical variant of the CVDE polypeptide of SEQ ID NO:1. The term "CVDE polypeptide as used herein includes variants. Such a variant typically has at least 40%, at least 45%, at least 50%, at least 55%, at least 60%, at least 65%, at least 70%, or at least 75%, at least 80%, at least 85%, at least 90%, or at least 95% identity to SEQ ID NO:1, or to a homolog of SEQ ID NO:1 isolated from a green alga other than *Chlamydomonas*. As used herein, the term "variant" encompasses biologically active polypeptides having one or more substitutions, deletions, or insertions relative to a CVDE polypeptide reference sequence, such as SEQ ID NO:1. Thus, the term "variant" includes biologically active fragments as well as substitution variants.

In some embodiments, the CVDE polypeptide has a heterologous chloroplast transit peptide relative to the transit peptide sequence of SEQ ID NO:1, which corresponds to amino acids 1-56 of SEQ ID NO:1. In some embodiments, a CVDE polypeptide overexpressed in accordance with the disclosure has at least 40%, at least 45%, at least 50%, at least 55%, at least 60%, at least 65%, at least 70%, or at least 75%, at least 80%, at least 85%, at least 90%, or at least 95% identity to amino acids 57-876 of SEQ ID NO:1.

Figure 1C:
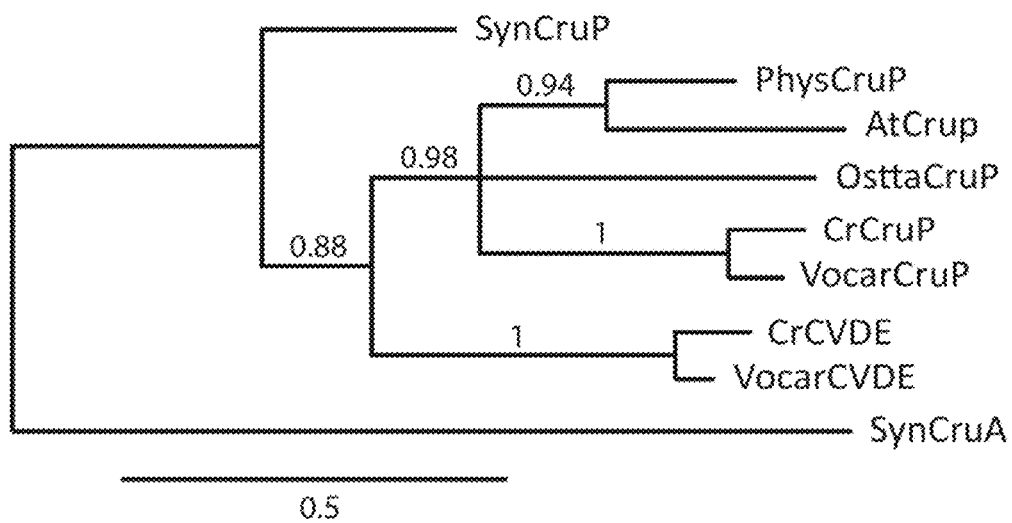
Figure 1D:
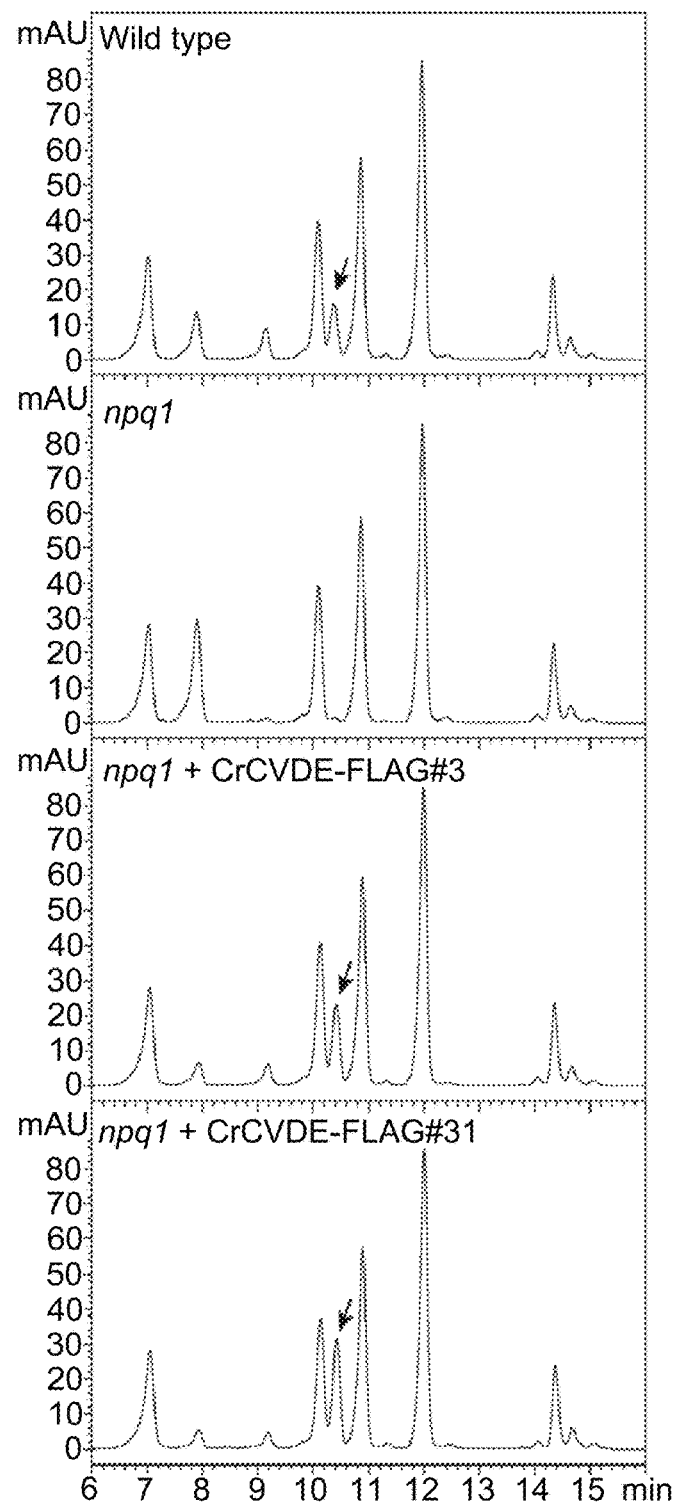
Figure 2A:
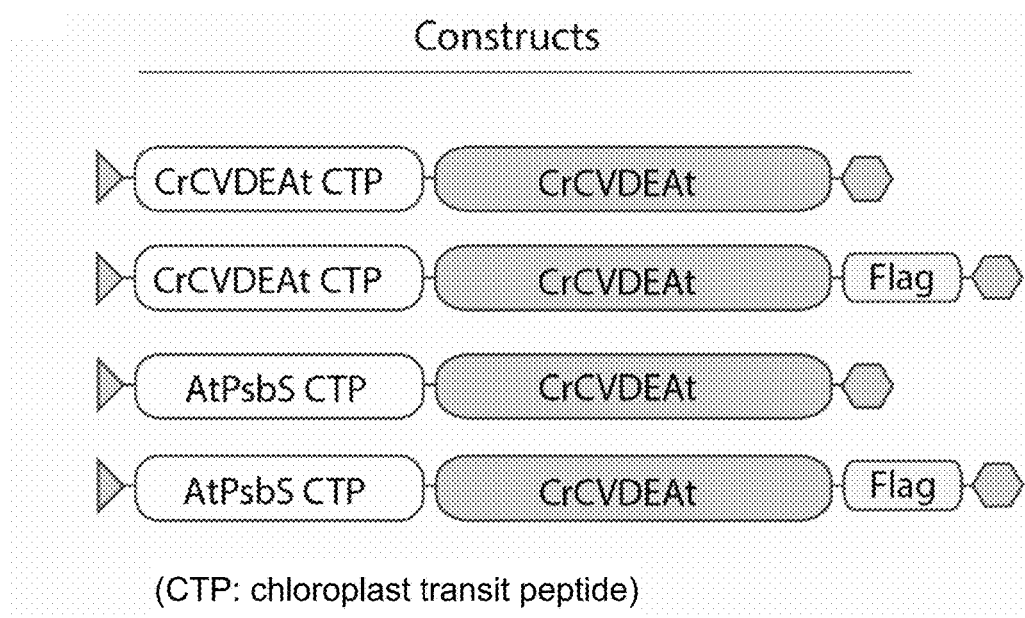
FIG. 2*a*-2*c*. Functional complementation of *Arabidopsis* vde1 mutant by expression of the *Chlamydomonas* CVDE protein.
Figure 2B:
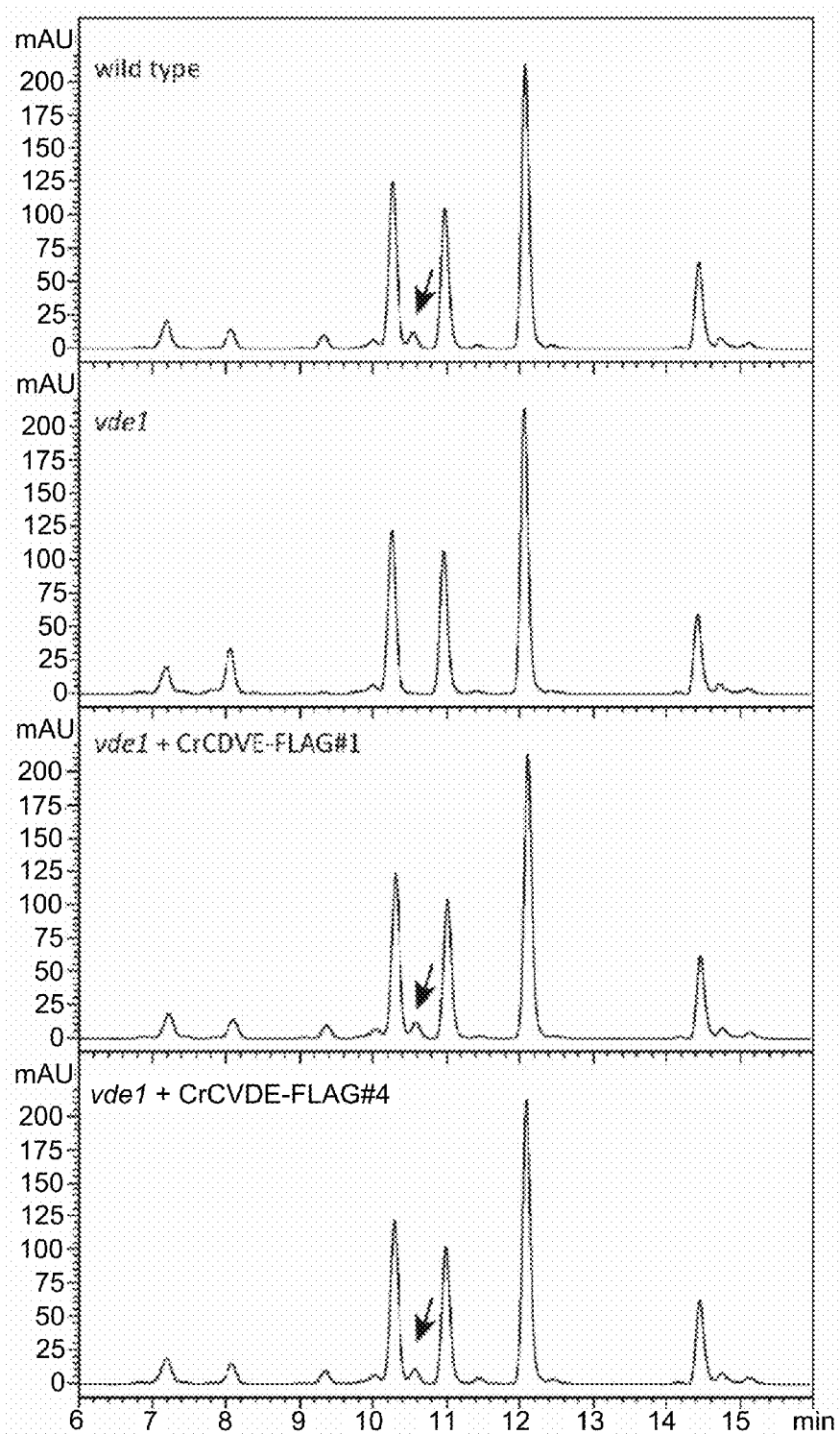
Figure 2C:
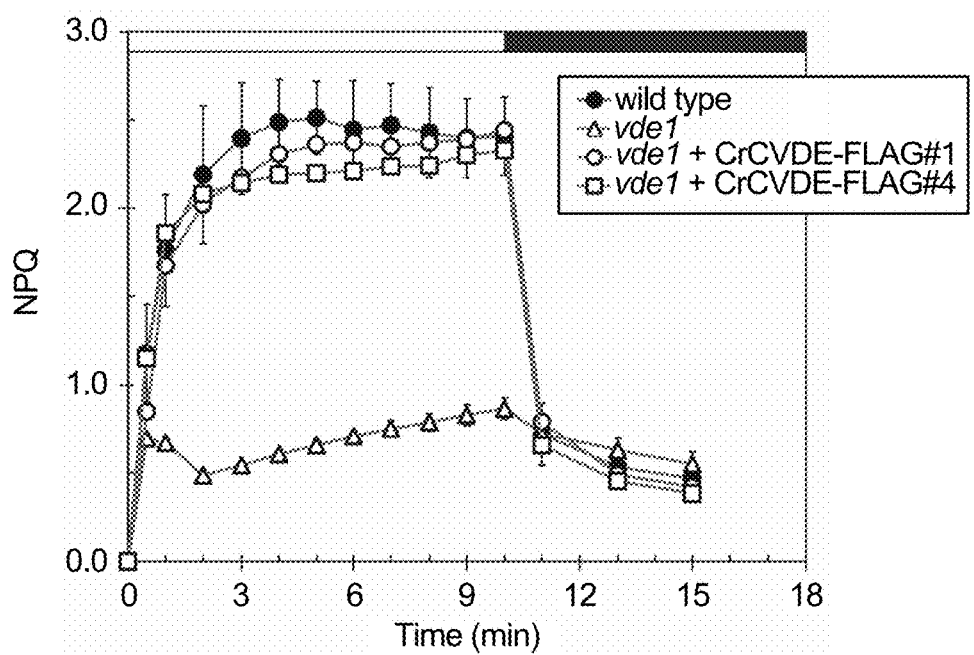
Figure 3A:
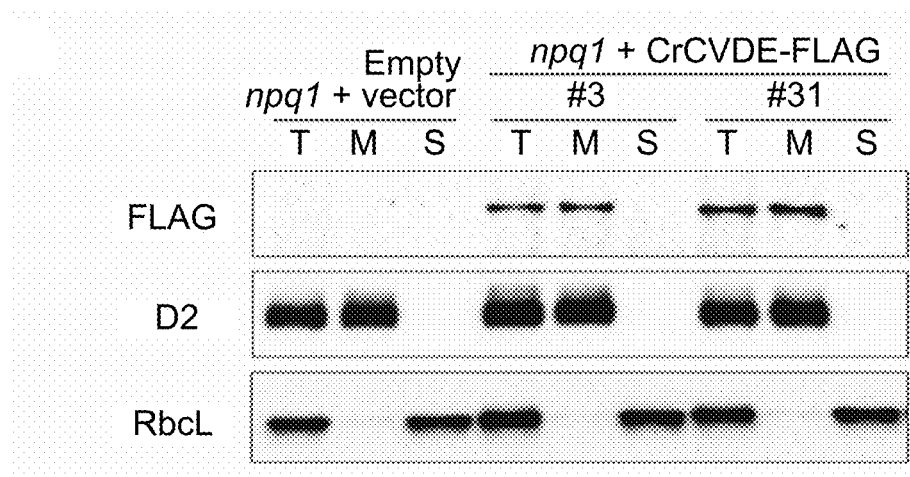
FIG. 3*a*-3*d*. Subcellular localization of CrCVDE proteins expressed in *Chlamydomonas* and *Arabidopsis*.
Figure 3B:
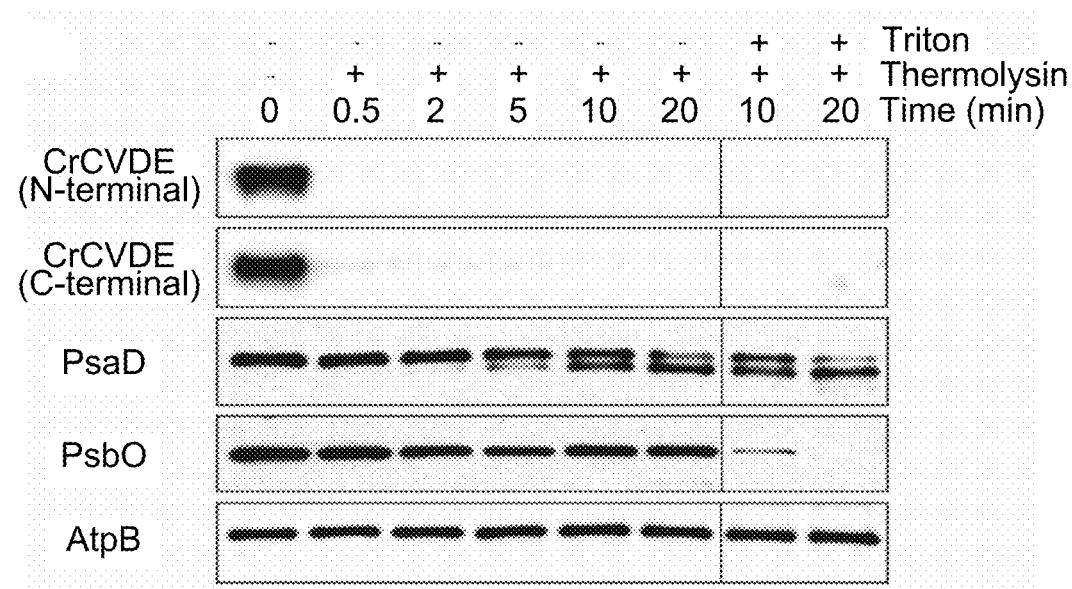
Figure 3C:
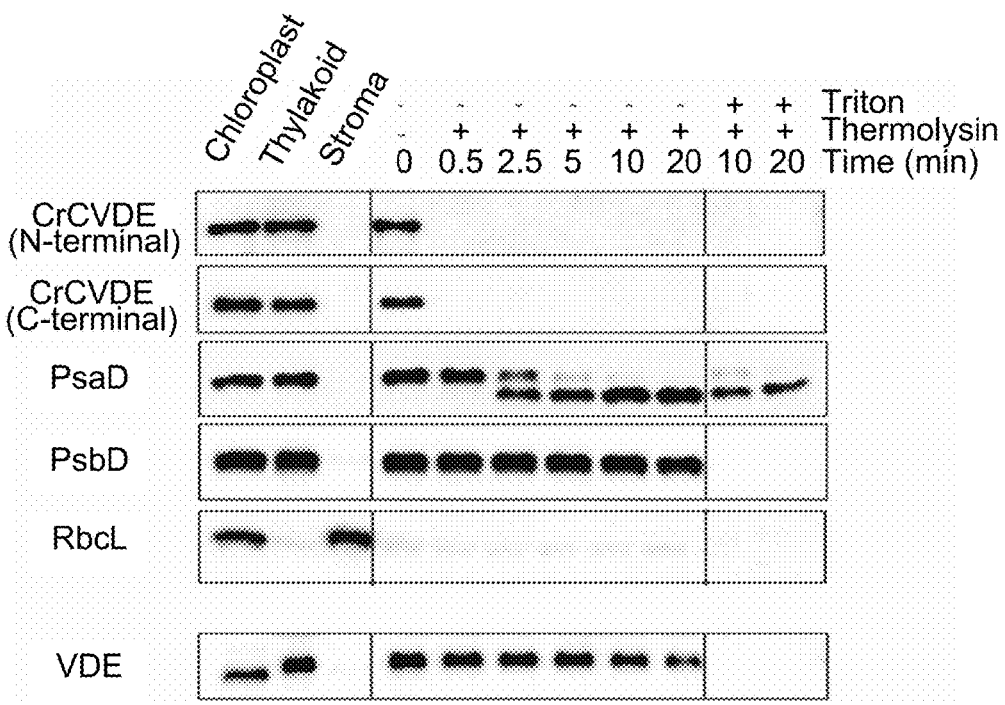
Figure 3D:
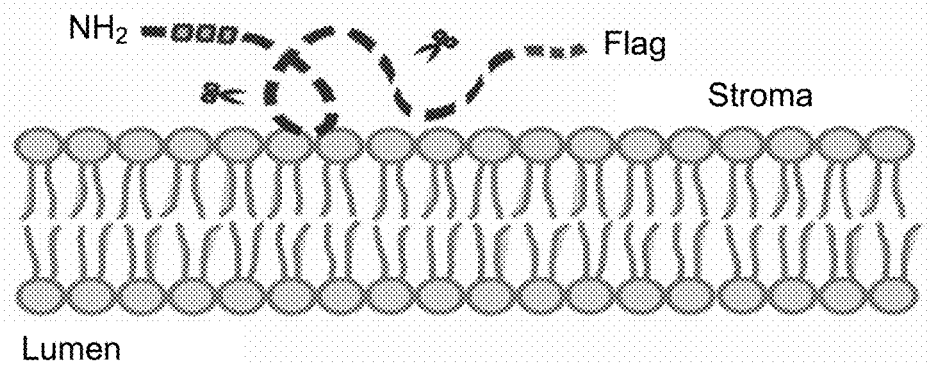

A comparison of CVDE polypeptide sequences to other VDE polypeptides in plants shows that the CVDE polypeptide shares very little identity with other VDE polypeptides, less than 20%. The evolutionary origins of plant-type VDE and CVDE are clearly distinct. CVDE is a homolog of CruP and CruA (FIG. 1c and Extended Data FIG. 2). CruA is known to be involved in bacterial carotenoid biosynthesis as a lycopene cyclase[3], whereas CruP is a paralog of CruA.

Various kinds of plants or other photosynthetic organisms can be engineered to express a CVDE polypeptide. In some embodiments, the photosynthetic organism is a plant. The plant may be a monocotyledonous plant or a dicotyledonous plant. In certain embodiments of the invention, the plant is corn, switchgrass, sorghum, miscanthus, sugarcane, poplar, alfalfa, pine, wheat, rice, soy, cotton, barley, turf grass, tobacco, potato, bamboo, rape, sugar beet, sunflower, willow, eucalyptus, millet, or any other plant or moss.

In some embodiments, the photosynthetic organism is a golden-brown algae (Chrysophyta), a fire algae (Pyrrophyta), a brown algae (Phaeophyta), a yellow-green algae (Xanthophyta), a eustigmatophyt (e.g., a Nannochloropsis sp), or a diatom (Bacillariophyta).

In some embodiments, the photosynthetic organism is a green alga, e.g., *Chlamydomonas reinhardtii; Dunaliella salina; Chlorella fusca; Chlorella vulgaris; Scenedesmus obliquus;* and *Botryococcus braunii*.

In typical embodiments, a polynucleotide encoding a CVDE polypeptide, such as a polypeptide of SEQ ID NO:1, is codon optimized for expression in a plant of interest, or another photosynthetic organism of interest.

Method for preparing vectors suitable for transformation of host cells are known, as are techniques for transformation of a host cell. For example, a DNA sequence encoding a CVDE protein, can be combined with transcriptional and other regulatory sequences which will direct the transcription of the sequence from the gene in the intended cells, e.g., plant cells. In some embodiments, an expression vector that comprises an expression cassette that comprises the CVDE gene further comprises a promoter operably linked to the CVDE gene. In other embodiments, a promoter and/or other regulatory elements that direct transcription of the CVDE gene are endogenous to the plant, or other photosynthetic organism, and an expression cassette comprising the CVDE gene is introduced, e.g., by homologous recombination, such that the CVDE gene is operably linked to an endogenous promoter and is expression driven by the endogenous promoter.

In some embodiments, the promoter may be from a gene associated with photosynthesis in the species to be transformed or another species. For example such a promoter from one species may be used to direct expression of a protein in transformed green algae cells. Suitable promoters may be isolated from or synthesized based on known sequences from other photosynthetic organisms.

In some embodiments a promoter may be a constitutive promoter. In some embodiments the promoter is an inducible promoter, or a tissue-specific promoter. In some embodiments, a promoter can be used to direct expression of CVDE nucleic acids under the influence of changing environmental conditions.

Examples of constitutive promoters include those from viruses which infect plants, such as the cauliflower mosaic virus (CaMV) 35S transcription initiation region (see, e.g., Dagless, Arch. Virol. 142:183-191, 1997); the 1'- or 2'-promoter derived from T-DNA of *Agrobacterium tumefaciens* (see, e.g., Mengiste supra (1997); O'Grady, Plant Mol. Biol. 29:99-108, 1995); the promoter of the tobacco mosaic virus; the promoter of Figwort mosaic virus (see, e.g., Maiti, Transgenic Res. 6:143-156, 1997); actin promoters, such as the *Arabidopsis* actin gene promoter (see, e.g., Huang, Plant Mol. Biol. 33:125-139, 1997); alcohol dehydrogenase (Adh) gene promoters (see, e.g., Millar, Plant Mol. Biol. 31:897-904, 1996); ACT11 from *Arabidopsis* (Huang et al., Plant Mol. Biol. 33:125-139, 1996), Cat3 from *Arabidopsis* (GenBank No. U43147, Zhong et al., Mol. Gen. Genet. 251:196-203, 1996), the gene encoding stearoyl-acyl carrier protein desaturase from Brassica napus (Genbank No. X74782, Solocombe et al., Plant Physiol. 104:1167-1176, 1994), GPc1 from maize (GenBank No. X15596, Martinez et al., J. Mol. Biol. 208:551-565, 1989), Gpc2 from maize (GenBank No. U45855, Manjunath et al., Plant Mol. Biol. 33:97-112, 1997), other transcription initiation regions from various plant genes known to those of skill. See also Holtorf, "Comparison of different constitutive and inducible promoters for the overexpression of transgenes in *Arabidopsis thaliana*," Plant Mol. Biol. 29:637-646, 1995).

Alternatively, a promoter may be an inducible promoter, such a promoter that is induced by environmental conditions or an inducing chemical agent. Examples of such promoters include the auxin-response elements E1 promoter fragment (AuxREs) in the soybean (*Glycine max* L.) (Liu, Plant Physiol. 115:397-407, 1997); the auxin-responsive *Arabidopsis* GST6 promoter (also responsive to salicylic acid and hydrogen peroxide) (Chen, Plant J. 10: 955-966, 1996); the auxin-inducible parC promoter from tobacco (Sakai, 37:906-913, 1996); a plant biotin response element (Streit, Mol. Plant Microbe Interact. 10:933-937, 1997); and, the promoter responsive to the stress hormone abscisic acid (Sheen, Science 274:1900-1902, 1996). Examples of plant promoters inducible upon exposure to chemicals reagents that may be applied to the plant, such as herbicides or antibiotics, are the maize In2-2 promoter, activated by benzenesulfonamide herbicide safeners, can be used (De Veylder, Plant Cell Physiol. 38:568-577, 19997); a tetracycline-inducible promoter, such as described with transgenic tobacco plants containing the *Avena sativa* L. (oat) arginine decarboxylase gene (Masgrau, Plant J. 11:465-473, 1997);

or, a salicylic acid-responsive element (Stange, Plant J. 11:1315-1324, 1997; Uknes et al., Plant Cell 5:159-169, 1993); Bi et al., Plant J. 8:235-245, 1995).

Examples of useful inducible regulatory elements include copper-inducible regulatory elements (Mett et al., Proc. Natl. Acad. Sci. USA 90:4567-4571, 1993); Furst et al., Cell 55:705-717, 1988); tetracycline and chlor-tetracycline-inducible regulatory elements (Gatz et al., Plant J. 2:397-404, 1992); Roder et al., Mol. Gen. Genet. 243:32-38, 1994); Gatz, Meth. Cell Biol. 50:411-424, 1995); ecdysone inducible regulatory elements (Christopherson et al., Proc. Natl. Acad. Sci. USA 89:6314-6318, 1992; Kreutzweiser et al., Ecotoxicol. Environ. Safety 28:14-24, 1994); heat shock inducible regulatory elements (Takahashi et al., Plant Physiol. 99:383-390, 1992; Yabe et al., Plant Cell Physiol. 35:1207-1219, 1994; Ueda et al., Mol. Gen. Genet. 250: 533-539, 1996); and lac operon elements, which are used in combination with a constitutively expressed lac repressor to confer, for example, IPTG-inducible expression (Wilde et al., EMBO J. 11:1251-1259, 1992). An inducible regulatory element useful in the transgenic plants of the invention also can be, for example, a nitrate-inducible promoter derived from the spinach nitrite reductase gene (Back et al., Plant Mol. Biol. 17:9 (1991)) or a light-inducible promoter, such as that associated with the small subunit of RuBP carboxylase or the LHCP gene families (Feinbaum et al., Mol. Gen. Genet. 226:449 (1991); Lam and Chua, Science 248:471 (1990)).

In some embodiments, the promoter may be a tissue-specific promoter such as a leaf promoter, e.g., as the ribulose bisphosphate carboxylase (RBCS) promoters can be used. For example, the tomato RBCS1, RBCS2 and RBCS3A genes are expressed in leaves and light-grown seedlings, only RBCS1 and RBCS2 are expressed in developing tomato fruits (Meier, FEBS Lett. 415:91-95, 1997). A ribulose bisphosphate carboxylase promoters expressed almost exclusively in mesophyll cells in leaf blades and leaf sheaths at high levels (e.g., Matsuoka, Plant J. 6:311-319, 1994), can be used. Another leaf-specific promoter is the light harvesting chlorophyll a/b binding protein gene promoter (see, e.g., Shiina, Plant Physiol. 115:477-483, 1997; Casal, Plant Physiol. 116:1533-1538, 1998). The *Arabidopsis thaliana* myb-related gene promoter (Atmyb5) (Li, et al., FEBS Lett. 379:117-121 1996), is leaf-specific. The Atmyb5 promoter is expressed in developing leaf trichomes, stipules, and epidermal cells on the margins of young rosette and cauline leaves, and in immature seeds. Atmyb5 mRNA appears between fertilization and the 16 cell stage of embryo development and persists beyond the heart stage. A leaf promoter identified in maize (e.g., Busk et al., Plant J. 11:1285-1295, 1997) can also be used.

One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

A vector comprising CVDE nucleic acid sequences will typically comprise a marker gene that confers a selectable phenotype on the cell to which it is introduced. Such markers are known. For example, the marker may encode antibiotic resistance, such as resistance to kanamycin, G418, bleomycin, hygromycin, and the like.

Additional sequence modifications may be made that are also known to enhance gene expression in a plant or other photosynthetic organism. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence may also be modified to avoid predicted hairpin secondary mRNA structures.

It should be recognized that in the context of the present invention, transgenic plants, or a transgenic photosynthetic organism, encompasses the plant or plant cell in which the expression cassette is introduced as well as progeny of such plants or plant cells that contain the expression cassette, including the progeny that have the expression cassette stably integrated in a chromosome.

EXAMPLES

The examples described herein are provided by way of illustration only and not by way of limitation. Those of skill in the art will readily recognize a variety of non-critical parameters that could be changed or modified to yield essentially similar results.

Mutants defective in the xanthophyll cycle and qE have been identified in the unicellular green alga *Chlamydomonas reinhardtii* and the model plant *Arabidopsis thaliana*[9,10]. The npq1 mutants are defective in VDE activity and are unable to convert Vio to Anthera and Zea in high light (panels a and d of FIG. 1). Although the *Arabidopsis* npq1 mutant was shown to affect the VDE gene[10], the molecular basis of the *Chlamydomonas* npq1 mutant has been mysterious, because the *Chlamydomonas* genome lacks an obvious ortholog of the VDE gene found in plants and other algae.

Figure 4:
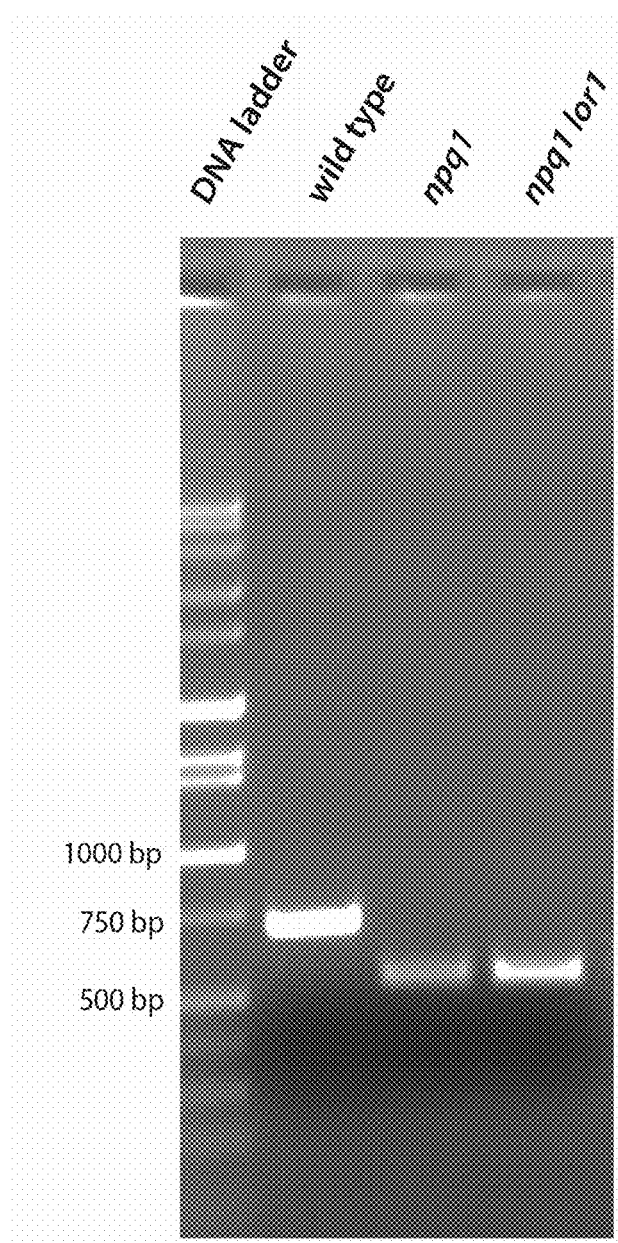
FIG. 4. PCR analysis of Cre04.g221550. Total genomic DNA from *Chlamydomonas* wild type, npq1 mutant, and npq1 lor1 double mutant was used as template, and a DNA segment containing exons 4 and 5 was amplified by PCR. The fragment amplified from wild type is ~690 bp, whereas the npq1 mutant yields a shorter fragment of ~520 bp.
Figure 5:
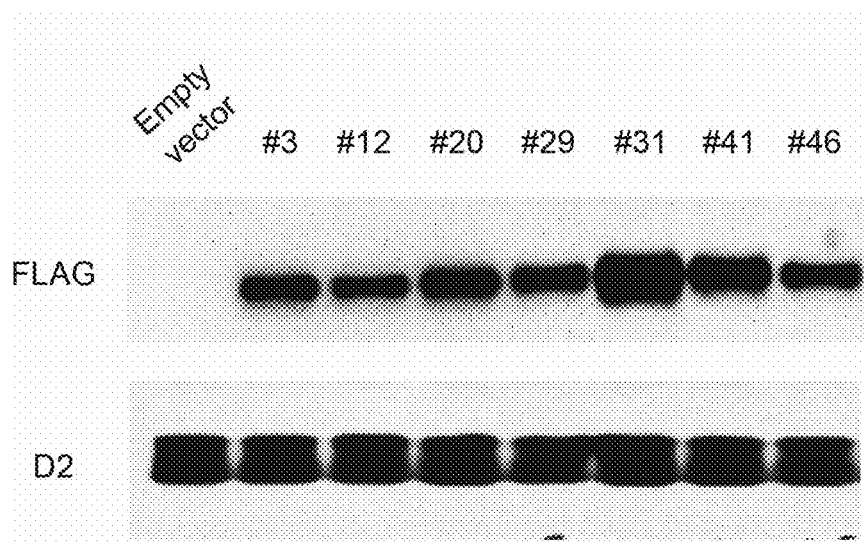
FIG. 5. CrCVDE protein levels in *Chlamydomonas* npq1 complemented lines. *Chlamydomonas* whole-cell protein samples were loaded on the basis of total cell number ($5 \times 10^5$ cells lane$^{-1}$), and immunoblot analysis was performed with polyclonal antibodies directed against the FLAG tag and D2 protein.

The *Chlamydomonas* npq1 mutation had been previously mapped to linkage group IV[11]. By fine mapping, we localized the npq1 mutation to a small region containing 13 gene models as candidate genes. One of these gene models (Cre04.g221550) encodes a putative FAD-dependent oxidoreductase with a predicted chloroplast transit peptide. Genomic polymerase chain reaction (PCR) analysis showed that there was a 164 bp deletion in the npq1 allele (panel b of FIG. 1, FIG. 4) of this gene. Introducing a Cre04.g221550 genomic clone into the npq1 mutant strain restored Zea synthesis in high light (panel d of FIG. 1). Interestingly, some rescued lines accumulated higher levels of Zea than the wild type (panel c of FIG. 1), which correlated with higher accumulation of the protein encoded by Cre04.g221550 (FIG. 5). From the results of these experiments, it is clear that the Zea deficiency of npq1 is caused by the loss of Cre04.g221550 function.

To determine if Cre04.g221550 actually encodes a protein with VDE activity, we tested if this gene could complement the *Arabidopsis* npq1 mutation (here called vde1), which is known to disrupt the endogenous plant-type VDE gene[10]. To ensure proper expression and chloroplast targeting of the Cre04.g221550 protein, we codon-optimized the Cre04.g221550 gene sequence for *Arabidopsis*, either with a sequence encoding its native, amino-terminal chloroplast transit peptide or the chloroplast transit peptide from the *Arabidopsis* PsbS protein, and with or without a carboxyl-terminal FLAG epitope tag (panel a of FIG. 2). *Arabidopsis* vde1 lines expressing each of the four versions of Cre04.g221550 displayed excess-light-induced Zea synthesis and NPQ phenotypes similar to wild-type plants (panels b and c of FIG. 2), showing that the Cre04.g221550 gene indeed encodes a functional, evolutionarily distinct VDE enzyme. Based on the presence of homologs of Cre04.g221550 in sequenced green algae of the class Chlorophyceae, we designate this gene as Chlorophycean VDE (CVDE) to distinguish it from the plant-type VDE gene.

Figure 6:
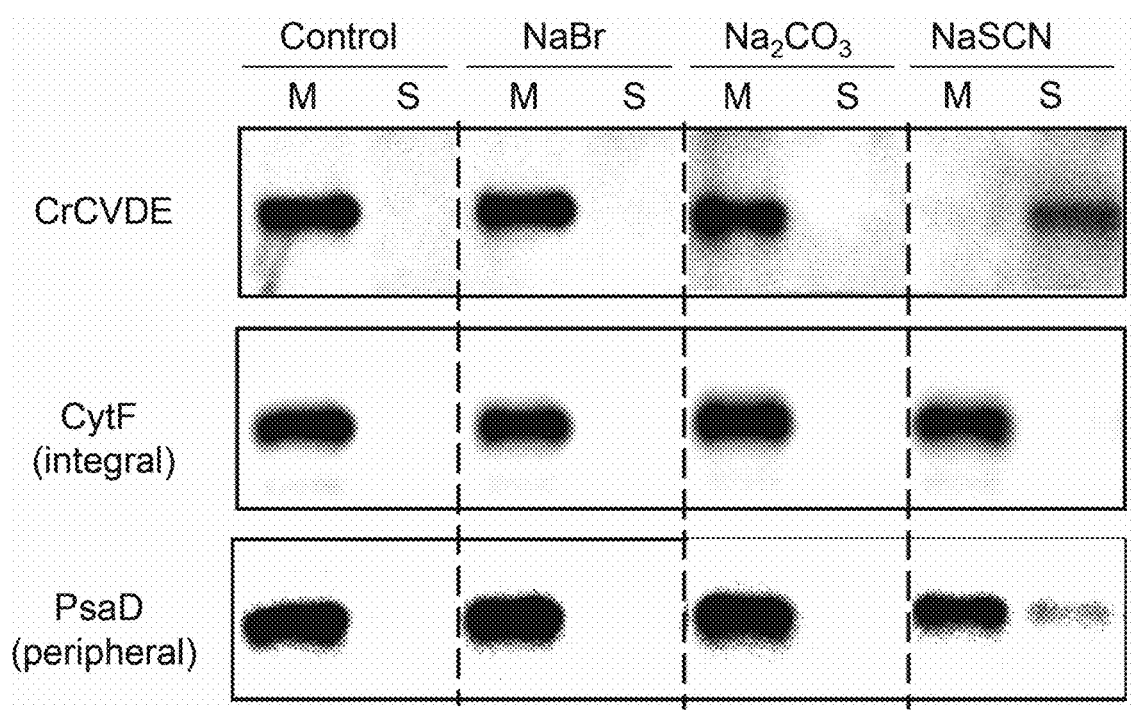
FIG. 6. Extraction of CrCVDE protein by chaotropic salts from *Arabidopsis* thylakoid membranes. Isolated thylakoids were incubated with 2 M NaBr, or 0.1 M $Na_2CO_3$, or 2 M NaSCN, or no additive on ice for 30 min. The samples were separated into membrane fraction (M) and supernatants (S) and analyzed by immunoblot analysis with specific antibodies. Transmembrane topology markers: CytF for integral membrane protein and PsaD for stroma-exposed and peripherally associated membrane protein.
Figure 7A:
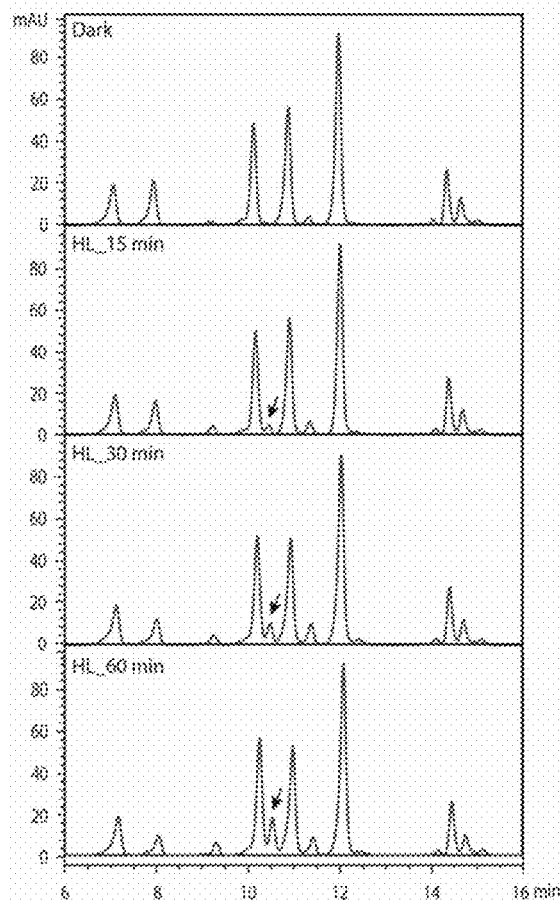
FIG. 7*a*-7*b*. Effect of the uncoupler nigericin on zeaxanthin formation in intact *Chlamydomonas* cells exposed to high light. The wild type *Chlamydomonas* cells were either mock-treated (FIG. 7*a*) or incubated with 10 µM nigericin (FIG. 7*b*) in the dark for 30 minutes before high light transfer. The accumulation of zeaxanthin was assayed by HPLC after 0, 15, 30, and 60 minutes of high light exposure. Arrows denote the Zea peak resulting from CVDE activity.
Figure 7B:
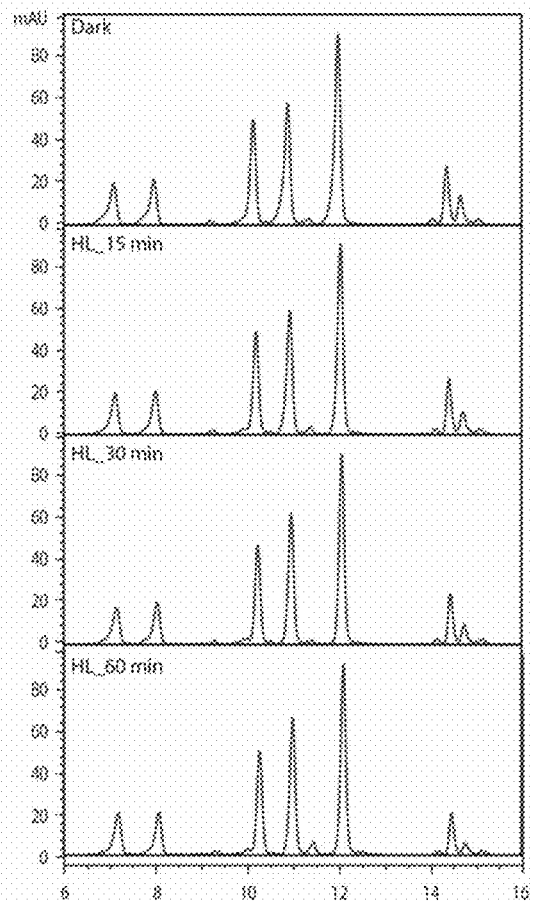

Plant-type VDE is localized in the thylakoid lumen and associates with the thylakoid membrane, where it catalyzes the de-epoxidation reaction on membrane-associated Vio. We used lines of both the *Chlamydomonas* npq1 mutant and the *Arabidopsis* vde1 mutant complemented with a carboxyl-terminal FLAG-tagged version of the *Chlamydomonas* CVDE (CrCVDE) protein to determine its localization. The functional carboxyl-terminal tagging demonstrated that this modification does not impair CrCVDE enzyme activity (panels b and c of FIG. 2). Using either a polyclonal antibody raised against an N-terminal 15 amino acid peptide of mature CrCVDE or a commercial antibody raised against the FLAG epitope, we detected the CrCVDE protein at a molecular mass of 90 kDa (FIG. 3), which is the predicted size of the mature protein after cleavage of the chloroplast transit peptide. As expected, the CrCVDE protein is associated with the thylakoid membrane in both *Chlamydomonas* and *Arabidopsis* (panels a, b, and c of FIG. 3). To determine the topology of CrCVDE, we performed a limited proteolysis experiment with isolated thylakoid membranes from both *Chlamydomonas* and *Arabidopsis* complemented lines. Thermolysin treatment resulted in complete cleavage of the CrCVDE protein, even more rapidly than the cleavage of the stroma-exposed PsaD subunit of photosystem I, which was quickly digested to a thermolysin-resistant fragment (panels b and c of FIG. 3). In contrast, the PsbO subunit of photosystem II, located in the thylakoid lumen, was completely resistant to thermolysin unless the membrane was solubilized with detergent (panels b and c of FIG. 3). In *Arabidopsis*, the lumen-localized plant-type VDE protein (in the vde1 mutant complemented with a FLAG-tagged version of the *Arabidopsis* VDE gene) was not affected unless the membrane was solubilized with detergent (panel c of FIG. 3). These results strongly suggest that the epitope-tagged CrCVDE protein is located on the stromal side of the thylakoid membrane when expressed in either *Chlamydomonas* or in *Arabidopsis* (panel d of FIG. 3), which differs from the plant-type VDE that is located in the thylakoid lumen (panel c of FIG. 3). The stroma-exposed location of CrCVDE was further supported by the presence of an FAD-binding domain in the mature CrCVDE protein (FAD is present in the stroma but not the thylakoid lumen). Salt wash assays indicated that CrCVDE is peripherally associated with the membrane and could be extracted by NaSCN (FIG. 6).

The in vivo substrate of VDE, Vio, is free in the membrane lipid phase rather than bound to pigment proteins[2,12]. Therefore, one possible explanation of functional replacement of plant-type VDE in *Arabidopsis* by CrCVDE is that substrate Vio molecules are accessible to enzymes on either side of the thylakoid membrane (i.e., in the thylakoid lumen or in the stroma of the chloroplast). This is likely, because addition of partially purified plant-type VDE from spinach to the stromal side of thylakoids isolated from the *Arabidopsis* vde1 mutant rescued the mutant phenotype in vitro[13]. Plant-type VDE requires ascorbate to catalyze the de-epoxidation reaction, but at this time it is not clear what other substrates are required for CVDE activity, nor is it clear how changes in the chloroplast stroma during excess light could induce the activity of this enzyme.

Figure 9:
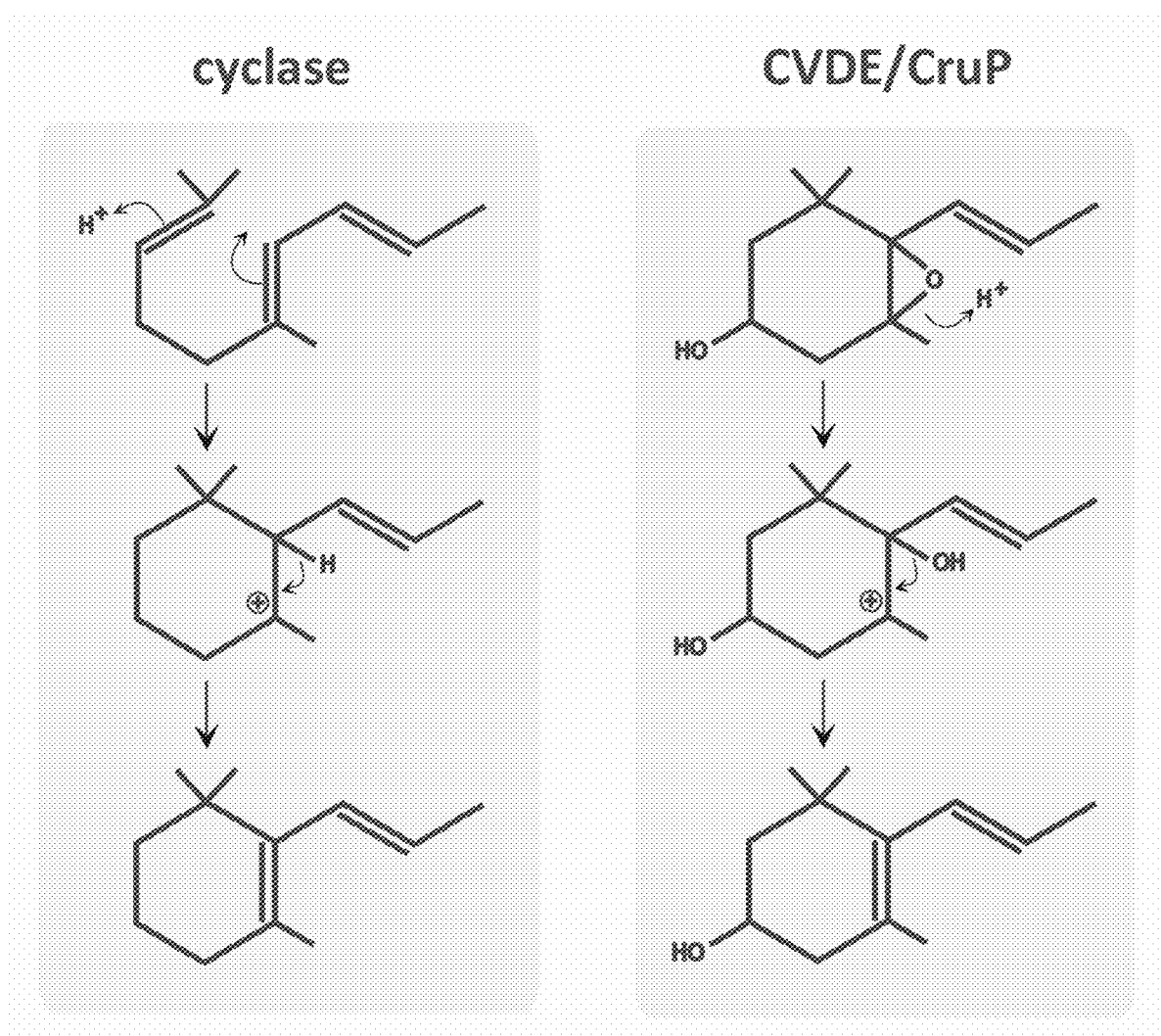
FIG. 9. Proposed de-epoxidase reaction mechanism and similarity to cyclase reaction involving a carbonium ion intermediate[25].

The evolutionary origins of plant-type VDE and CVDE are clearly distinct. CVDE is a homolog of CruP and CruA (panel c of FIG. 1 and FIG. 8a-8d). CruA is known to be involved in bacterial carotenoid biosynthesis as a lycopene cyclase[3], whereas CruP is a paralog of CruA. We note that the proposed carotenoid cyclase and de-epoxidase reaction mechanisms are similar (FIG. 9), suggesting that a de-epoxidase enzyme could evolve from a cyclase. Our demonstration that CrCVDE has VDE activity suggests that its paralog CruP, which is widely distributed in oxygenic photosynthetic organisms[14], might also be a de-epoxidase. Based on the observation that cruP mutants or overexpressors of *Arabidopsis* accumulate more or less β-carotene-5,6-epoxide (an oxidized derivative of β-carotene), respectively, when challenged by stress[14], we hypothesize that CruP is a β-carotene-5,6-epoxide de-epoxidase. CVDE and CruP homologs are present in *Chlamydomonas* and its multicellular relative *Volvox carteri*, but only CruP homologs can be found in *Ostreococcus tauri*, *Arabidopsis thaliana*, and *Physcomitrella patens*. Phylogenetic analysis strongly suggests that CVDE evolved by duplication of CruP in the ancestor of green algae and plants and that CVDE has been selectively lost in some clades of the Viridiplantae (panel c of FIG. 1), however the limited numbers of genomes sequenced within this clade prohibits any further speculation about the distribution or origin of CVDE-related xanthophyll cycling.

The evolutionary history of algae (and plants) is complicated by endosymbiosis and horizontal gene transfer events. We showed that a novel de-epoxidase from a green algal group is functional in a land plant, despite their evolutionary separation by over 700 million years[15]. Therefore it may be possible to mix and match the regulatory components of light harvesting from different clades of photosynthetic organisms to effectively tune photosynthetic efficiency and increase photosynthetic productivity.

Transient Expression of *Chlamydomonas* CVDE in *Nicotiana benthamiana* Speeds Up Induction of NPQ

Figure 10A:
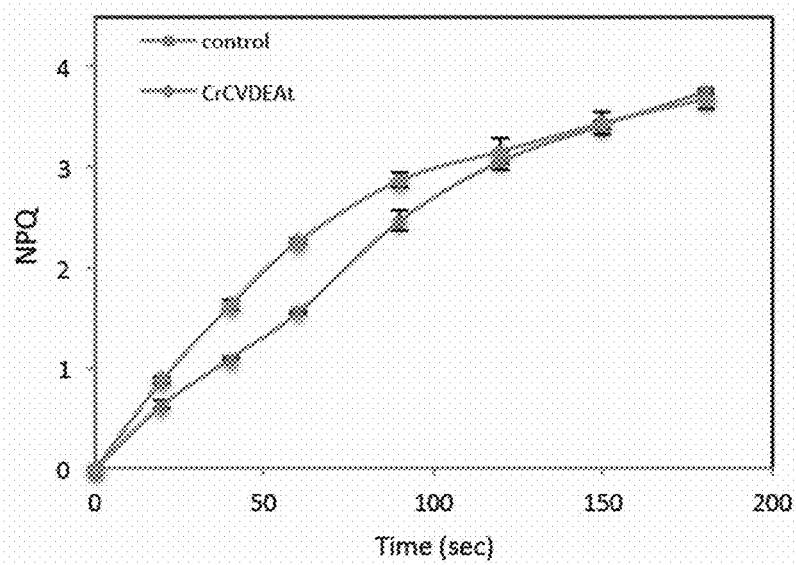
FIG. 10*a*-10*c*. Over-expression of *Chlamydomonas* CVDE in *Nicotiana benthamiana*.
Figure 10B:
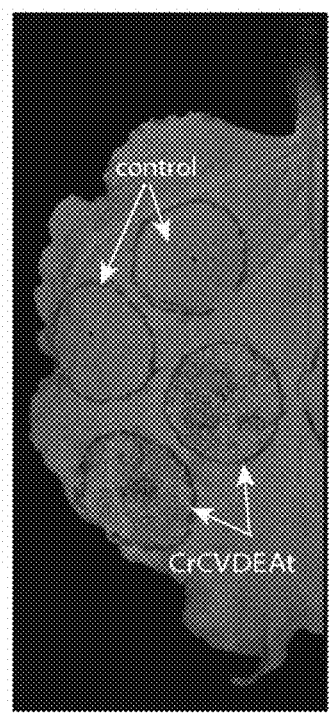
Figure 10C:
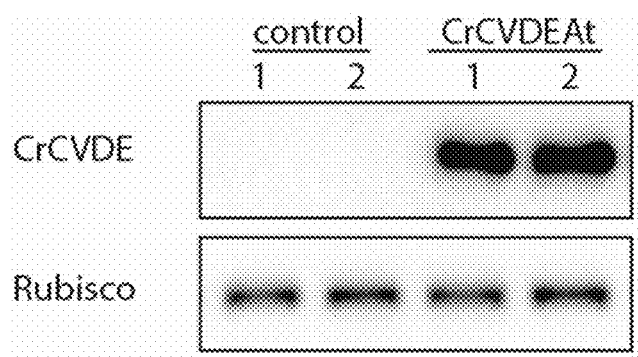

*Agrobacterium tumefaciens* strain GV3101 containing pERG100-CrCVDEAt, which was generated and used for the purpose of *Arabidopsis* stable transformation, was also employed for the transient expression in tobacco. The agrobacteria were resuspended in induction medium (0.1 mM MES pH 5.6, 0.1 mM $MgCl_2$, 0.1 mM acetosyringone) and incubated at 28° C. for 2 hours. The suspension was then diluted to an $A_{600}$ of 0.5 and 200 μl of dilutions were injected into *N. benthamiana* leaves using a blunt-end 1 ml syringe. Plants were grown under constant light (~70 μmol photons $m^{-2}$ $s^{-1}$) for 48-60 h before chlorophyll fluorescence measurement, and leaf spots were collected for immunoblot analysis. FIG. 10 shows that CVDE was expressed in tobacco.

Methods

Genetic Mapping and PCR Analysis

The fine mapping of the npq1 mutation was done by scoring PCR-based markers on selected tetrad mutant progeny derived from a cross between npq1 (137c strain background) and the polymorphic wild-type strain S1D2 (CC-2090). Markers were designed based on information in Kathir et al.[16] and the marker list from David Stern available at the www website chlamy.org. To identify the mutation in the CVDE gene, genomic DNA PCR was performed with a series of primer pairs that collectively span the entire gene, and the PCR products were sequenced for comparison between the wild type and the npq1 mutant. The primers that resulted in different length products between wild type and npq1 were RMD345 (5'-CTTGGCGGAAGCAGAG-TATGGC-3' (SEQ ID NO: 18)) and RMD346 (5'-CGGC-CTCCCTTCATCCCTCCCAC-3' (SEQ ID NO: 19)).

Phylogenetic Analysis

CVDE homologs and CruP homologs were identified by searching via BlastP and tBlastN against the sequenced proteome and genome database, respectively, with an e-value cutoff of $1e^{-90}$. The potential chloroplast transit peptides for CVDE homologs or CruP homologs were predicted by aligning respective homologs from organisms with or without chloroplasts using the Clustal Omega program (version1.2.1; http web address ebi.ac.uk/Tools/msa/clustalo/). The predicted mature proteins were aligned using Clustal Omega and BoxShade (version 3.21; available at the http web address ch.embnet.org/software/BOX_form.html). The phylogenetic tree was constructed at Phylogeny.fr (http web address phylogeny.lirmm.fr/phylo_cgi/advanced.cgi) with Gblocks for alignment curation, PhyML for construction of Phylogenetic tree, and Tree Dyn for visualization of phylogenetic tree.

Complementation of Chlamydomonas npq1 Mutant

For complementation of npq1, an 11.5-kb EcoRV/NotI fragment of BAC clone 33B9 containing the CVDE gene was subcloned into the pBC1 vector[17] to generate pCVDEg. For complementation of npq1 with a carboxyl-terminal FLAG-tagged version of the CVDE protein, the 1.4 kb SbfI/BglII fragment of pCVDEg containing the 3' terminus of the CVDE gene was subcloned into the pUC19-BglII vector to generate pUC19-BglII-pCVDE. The 0.4 kb NcoI/BglII fragment of pUC19-BglII-pCVDE was then replaced by a synthesized version (Integrated DNA Technologies, Inc.), which contains a carboxyl-terminal FLAG-tag linked with the CVDE protein through two glycines to generate plasmid pUC19-BglII-pCVDE-FLAG. The 1.4 kb SbfI/BglII fragment of pUC19-BglII-pCVDE-FLAG was then ligated into pCVDEg double-digested with same enzymes to generate pCVDEg-FLAG. Both pCVDEg and pCVDEg-FLAG were separately transformed into the npq1 mutant using the glass bead method as described previously[18]. The positive transformants were selected on paromomycin and then screened for zeaxanthin accumulation after high light exposure by HPLC as previously described[19].

Complementation of Arabidopsis vde1 Mutation by Chlamydomonas CVDE

The predicted protein sequences of Chlamydomonas CVDE were retrieved from both Phytozome at http www website phytozome.net (protein ID: Cre04.g221550.t1.2) and the Joint Genome Institute at http web address genome.jgi-psforg/Chlre4/Chlre4.home.html (protein ID: 522089). The predicted CVDE protein sequences were confirmed by comparing against each other and against the cDNA consensus obtained from UCSC/UCLA genome browser at hattp web address genomes.mcdb.ucla.edu. The CDS of the CrCVDEAt gene was then codon-optimized and synthesized for Arabidopsis nuclear/cytoplasmic expression (GenScript). The synthetic CrCVDEAt gene was subcloned into the Gateway vector pDONR221, and a FLAG-tag was added right before the stop codon by 'Round-the-horn' site-directed mutagenesis (http address openwetware.org/wiki/%27Round-the-horn_site-directed_mutagenesis). Sequence encoding the Arabidopsis PSBS transit peptide (first 54 amino acids) was amplified to replace the predicted native CrCVDE transit peptide (first 56 amino acids) in versions of each construct using gene SOEing[20]. The CrCVDEAt gene and the FLAG-tagged CrCVDEAt gene were subcloned into the pEarleyGate100 vector[21] and transformed into the Arabidopsis vde1 mutant[10] using the floral dip method[22]. As a positive control, a vector containing a FLAG-tagged version of the Arabidopsis VDE1 gene was also transformed. The transformants were selected on Murashige and Skoog plates containing 20 µg/mL glufosinate ammonium, screened for NPQ capacity with the IMAGING-PAM M-series (Heinz Walz), measured for NPQ induction with an FMS2 fluorometer (Hansatech Instruments) as previously described[23], and assayed for the accumulation of zeaxanthin after high light exposure by HPLC as described[19].

Chlamydomonas Cell Fractionation

Chlamydomonas cells were grown photoheterotrophically in TAP medium[24] to medium logarithmic phase (approximately $5 \times 10^6$ cells $mL^{-1}$) and harvested by centrifugation at 3,000 g for 5 min. Cells were resuspended in PBS buffer to a density of $2 \times 10^8$ cells $mL^{-1}$ and broken by FastPrep-24 (MP Biomedicals, Solon, Ohio) with lysing matrix J at a speed of 4.0 m/sec for 40 sec. Total membrane and total supernatant were separated by centrifugation at 20,000 g, 4° C. for 10 min. Total membranes were washed three times before being resuspended with 1×PBS buffer containing 100 µM phenylmethylsulfonyl fluoride (PMSF). Samples were then subjected to immunoblot analysis as described below.

Chlamydomonas and Arabidopsis Thylakoid Isolation

The Chlamydomonas thylakoid were isolated by a modification of the flotation procedure described previously[25]. The Chlamydomonas cells were grown in 400 mL TAP under low light and harvested at mid-logarithmic growth phase. The cell pellet was resuspended in 20 mL of 25 mM HEPES (pH 7.5), 0.3 M sucrose, 10 mM $CaCl_2$, 10 mM $MgCl_2$ with protease inhibitors. The cells were broken by passing the resuspended cells through a chilled French pressure cell, and the homogenate was centrifuged at 18,000 rpm for 10 min. The supernatant was discarded and the pellet was gently resuspended with a paintbrush in 5 mL of 5 mM HEPES (pH 7.5), 1.8 M sucrose, 10 mM $CaCl_2$, 10 mM $MgCl_2$. The resuspension was carefully transferred into a clear tube for SW41 rotor and topped with 6 mL of 5 mM HEPES (pH 7.5), 0.5 M sucrose, 10 mM $CaCl_2$, 10 mM $MgCl_2$. The tubes were centrifuged at 38,000 rpm (SW41, 4° C.) for 1 hour. The membrane layer at the interface of two solutions was carefully transferred to a 1.5 mL eppendorf tube containing 1 m: of 25 mM HEPES (pH 7.5), 0.3 M sucrose, 10 mM $CaCl_2$, 10 mM $MgCl_2$.

Fresh Arabidopsis rosette leaves were harvested from 4-week-old plants grown in controlled conditions of 14 h light, 22° C./10 h dark, 23° C., with a light intensity of 150 µmol photons $m^{-2}$ $s^{-1}$ and stored on ice. The Arabidopsis thylakoids were isolated from the leaves as previously described[26].

Protease Protection Assay

Thylakoids were resuspended in 0.3 M sorbitol, 2.5 mM EDTA 5 mM $MgCl_2$, 0.5% (w/v) BSA, 20 mM HEPES (pH 7.6) at 0.3 nmol chlorophyll a per mL. The reaction was started by the addition of thermolysin (EMD Millipore) at a final concentration of 20 µg $mL^{-1}$ to 400 µL thylakoids preparation. The reaction was stopped by transferring 60 µL to a tube containing 6 µL of 500 mM EDTA at six different time points: 0, 0.5, 2, 5, 10, 20 min. The tubes were votexed immediately, and 66 µL of 2× sample buffer was added.

CVDE Antibody Generation and Immunoblot Analysis

The polyclonal antibody recognizing CrCVDE was generated in rabbits against an epitope located near the N-terminus of the protein sequence of CrCVDE (CLRNQKHEPEKKGPK (SEQ ID NO:20)), and the resulting crude serum was affinity purified (ProSci Inc., Poway, Calif.). Polyclonal antibodies against D2, PsbO, PsaD, and RbcL were obtained from Agrisera (Sweden) and FLAG antibody was from Thermo Fisher Scientific. Protein samples were solubilized with 2× solubilization buffer (500 mM Tris-HCl (pH 6.8), 7% SDS, 20% glycerol (v/v), 2 M urea, 10% β-mercaptoethanol (v/v)) by pipetting up and down several times before incubation at room temperature for 30 min. For immunoblot analysis of CVDE, protein samples were separated with NuPAGE Novex 3-8% Tris-Acetate mini gels (Life Technologies, Carlsbad, Calif.). For immunoblot analysis of all other proteins, protein samples were separated with Novex 10-20% Tris-Glycine mini gels (Life Technologies, Carlsbad, Calif.). A total of $5 \times 10^5$ cells was loaded per lane for *Chlamydomonas* samples, and a total of 1.5 µg chlorophyll was loaded per lane for *Arabidopsis* samples. Proteins were then transferred to nitrocellulose membranes, blocked with 5% nonfat dry milk, and blotted with specific polyclonal antibodies. The signals were detected by Supersignal West Femto Chemiluminescent substrate detection system (Thermo Scientific).

Polypeptide Extraction from Thylakoid

Freshly isolated thylakoids were resuspended at 0.5 mg chlorophyll/ml in thylakoid resuspension buffer (0.3M sorbitol, 2.5 mM EDTA, 5 mM MgCl$_2$, 0.5% (wt/vol) BSA, 20 mM HEPES (pH 7.6)) containing 2 M NaBr, or 0.1 M Na2CO3, or 2 M NaSCN, or no additive. After incubation on ice for 30 min, the membrane and the supernatant fraction were separated by centrifugation at 20,000 g, 4° C. for 10 min. The membrane fractions were washed three times before being resuspended with 1×PBS buffer containing 1 mM PMSF. The supernatants were precipitated in 80% acetone and centrifuged at 20,000 g, 4° C. for 10 min to collect pellets. The pellets were then resuspended with 1×PBS buffer containing 1 mM PMSF. The membrane and supernatant fraction were subsequently subjected to immunoblot analysis.

All patents, patent applications, accession numbers, and other published reference materials cited in this specification are hereby incorporated herein by reference in their entirety for their disclosures of the subject matter in whose connection they are cited herein.

REFERENCES CITED BY NUMBER IN SPECIFICATION

1 Demmig-Adams, B. Carotenoids and photoprotection in plants: A role for the xanthophyll zeaxanthin. *Biochimica et Biophysica Acta (BBA)—Bioenergetics* 1020, 1-24 (1990).
2 Jahns, P., Latowski, D. & Strzalka, K. Mechanism and regulation of the violaxanthin cycle: The role of antenna proteins and membrane lipids. *Biochimica et Biophysica Acta (BBA)—Bioenergetics* 1787, 3-14 (2009).
3 Maresca, J. A., Graham, J. E., Wu, M., Eisen, J. A. & Bryant, D. A. Identification of a fourth family of lycopene cyclases in photosynthetic bacteria. *Proceedings of the National Academy of Sciences* 104, 11784-11789 (2007).
4 Niyogi, K. K. Photoprotection revisited: genetic and molecular approaches. *Annual Review of Plant Physiology and Plant Molecular Biology* 50, 333-359 (1999).
5 Muller, P., Li, X.-P. & Niyogi, K. K. Non-photochemical quenching. a response to excess light energy. *Plant Physiology* 125, 1558-1566 (2001).
6 Ruban, A. V., Johnson, M. P. & Duffy, C. D. P. The photoprotective molecular switch in the photosystem II antenna. *Biochimica et Biophysica Acta (BBA)—Bioenergetics* 1817, 167-181 (2012).
7 Niyogi, K. K. & Truong, T. B. Evolution of flexible non-photochemical quenching mechanisms that regulate light harvesting in oxygenic photosynthesis. *Current Opinion in Plant Biology* 16, 307-314 (2013).
8 Briantais, J. M., Vernotte, C., Picaud, M. & Krause, G. H. A quantitative study of the slow decline of chlorophyll a fluorescence in isolated chloroplasts. *Biochimica et Biophysica Acta* 548, 128-138 (1979).
9 Niyogi, K. K., Bjorkman, O. & Grossman, A. R. *Chlamydomonas* xanthophyll cycle mutants identified by video imaging of chlorophyll fluorescence quenching. *The Plant Cell* 9, 1369-1380 (1997).
10 Niyogi, K. K., Grossman, A. R. & Bjorkman, O. *Arabidopsis* mutants define a central role for the xanthophyll cycle in the regulation of photosynthetic energy conversion. *The Plant Cell* 10, 1121-1134 (1998).
11 Anwaruzzaman, M. et al. Genomic analysis of mutants affecting xanthophyll biosynthesis and regulation of photosynthetic light harvesting in *Chlamydomonas reinhardtii*. *Photosynth Res* 82, 265-276 (2004).
12 Yamamoto, H. Y. in *Photoprotection, Photoinhibition, Gene Regulation, and Environment* Vol. 21 *Advances in Photosynthesis and Respiration* (eds Barbara Demmig-Adams, William W. Adams, III, & Autar K. Mattoo) Ch. 1, 1-10 (Springer Netherlands, 2006).
13 Macko, S., Wehner, A. & Jahns, P. Comparison of violaxanthin de-epoxidation from the stroma and lumen sides of isolated thylakoid membranes from *Arabidopsis*: implications for the mechanism of de-epoxidation. *Planta* 216, 309-314 (2002).
14 Bradbury, L. M. T. et al. Lycopene cyclase paralog CruP protects against reactive oxygen species in oxygenic photosynthetic organisms. *Proceedings of the National Academy of Sciences* 109, E1888-E1897 (2012).
15 Leliaert, F. et al. Phylogeny and molecular evolution of the green algae. *Critical Reviews in Plant Sciences* 31, 1-46 (2012).
16 Kathir, P. et al. Molecular map of the *Chlamydomonas reinhardtii* nuclear genome. *Eukaryotic Cell* 2, 362-379 (2003).
17 Dent, R. M. et al. Large-scale insertional mutagenesis of *Chlamydomonas* supports phylogenomic functional prediction of photosynthetic genes and analysis of classical acetate-requiring mutants. *The Plant Journal* 82, 337-351 (2015).
18 Dent, R. M., Haglund, C. M., Chin, B. L., Kobayashi, M. C. & Niyogi, K. K. Functional genomics of eukaryotic photosynthesis using insertional mutagenesis of *Chlamydomonas reinhardtii*. *Plant Physiology* 137, 545-556 (2005).
19 Müller-Moulé, P., Conklin, P. L. & Niyogi, K. K. Ascorbate deficiency can limit violaxanthin de-epoxidase activity in vivo. *Plant Physiology* 128, 970-977 (2002).
20 Horton, R. M., Cai, Z. L., Ho, S. N. & Pease, L. R. Gene splicing by overlap extension: tailor-made genes using the polymerase chain reaction. *Biotechniques* 8, 528-535 (1990).
21 Earley, K. W. et al. Gateway-compatible vectors for plant functional genomics and proteomics. *The Plant Journal* 45, 616-629 (2006).
22 Zhang, X., Henriques, R., Lin, S.-S., Niu, Q.-W. & Chua, N.-H. *Agrobacterium*-mediated transformation of *Arabidopsis thaliana* using the floral dip method. *Nature Protocols* 1, 641-646 (2006).
23 Brooks, M. & Niyogi, K. in Chloroplast Research in *Arabidopsis* Vol. 775 *Methods in Molecular Biology* (ed R. Paul Jarvis) Ch. 16, 299-310 (Humana Press, 2011).
24 Harris, E. H. *The Chlamydomonas ourcebook. A Comprehensive Guide to Biology and Laboratory Use*. (Academic Press, 1989).
25 Chua, N. H. & Bennoun, P. Thylakoid membrane polypeptides of *Chlamydomonas reinhardtii*: wild-type and mutant strains deficient in photosystem II reaction center. *Proceedings of the National Academy of Sciences of the United States of America* 72, 2175-2179 (1975).

26 Brooks, M. D., Sylak-Glassman, E. J., Fleming, G. R. & Niyogi, K. K. A thioredoxin-like/β-propeller protein maintains the efficiency of light harvesting in *Arabidopsis*. *Proceedings of the National Academy of Sciences* 110, E2733-E2740 (2013).

27 Britton, G. Later reactions of carotenoid biosynthesis. *Pure Appl. Chem* 47, 223-236 (1976).

Illustrative sequences

SEQ ID NO: 1 CrCVDE protein sequence; chloroplast transit peptide underlined
MQQRLLKPHTAGRPSGAVPIAHGLVSGPRVQPAAPSARPASGNVTSHPVGARGPACDQ
ASSAGKRFDSLAAYGLARDVLTKQASNIEGNPIEFLDVTEKEWRALRNQKHEPEKKGPK
VVTYADELLFPDSASSSSASTSSSPHPHDYDVVICGGTLGLFLATALQLQGWRVAIVEKR
LVQGRNQEWNISWGELEVLVELGLLSEEELKGCVISEFNPIRVGFKGGEDIWTQDVLNL
GVHPRTLLDSLKRRFHAAGGIIFENTAFKHADVHPDGIKLSLAPGGAAAPVAVGDTNRP
NGLTTGGAAPAPSGPVAPRSMTTRLLLDCMGHYSDIVKQIRGRVKPDGMVLVVGGCAE
GFPAEANISADLLYSLSHARDDVQLFWEAFPAEGGQARTTYMFAYSDAHPDRPSFEALL
DTYFQMLPEYQGIPLDQLKFKRVLFGGFPCYSNGPLAPAFDRVMQIGDASAAQSPLSFG
GFGSMMRHLPRLARGLDQALQEDRLARPDLNWLHPYQPSLSASWLFQRSMSLAVGQV
AYPPDCPHAPAYYAAAKEAKAAAAAAAVDRAEGFDGLVSTAGERALSLQEAAMEAVE
AVAARFAAGSADPADYFHVEQEVPGAGSDRRTPQLASGKAQPAPPKLKKKLFERDFRT
APEWQRLPYTHVNEILGTNFGVMGVLGDRVLKPFLQDTIQLVPLSLSMTGMMLSNPVT
VSRVLMQVGPKTLVSWFAHYFALVAYSLGHVLLSPLRGVVPSYSFQRMLDALEYGSGS
DYRYHAPAGPAAGAAVSAGRGAPVAAALSAAARSIDGGAATESMDGGDGGDAAGEA
GAAGKSEGGSVKGRKAPKQQQPAAEPMPIPVPVAAATAAAAAMAAATMVVGLPGIGP
VTLG SEQ ID NO: 2 CrCVDE coding sequence
ATGCAGCAACGCCTTCTGAAGCCTCATACGGCCGGTCGCCCTAGCGGCGCTGTGCCT
ATCGCTCATGGTCTTGTCTCAGGGCCTCGCGTGCAGCCGGCTGCGCCCTCCGCTCGC
CCAGCGTCTGGTAATGTGACCTCACATCCAGTGGGCGCGCGCGGGCCCGCCTGCGA
CCAGGCCAGCAGTGCTGGCAAGCGTTTCGATAGCCTAGCAGCCTACGGGCTAGCTC
GGGACGTGCTTACGGAGCAGGCCTCGAACATTGAGGGCAACCCCATTGAGTTCCTTG
ACGTGACGGAAAAGTTCTGGAGAGCGCTTCGTAACCAGAAGCATGAGCCCGAGAAG
AAGGGCCCCAAGGTGGTCACATACGCGGACGAGCTCCTCTTCCCAGACTCCGCCTCC
TCCTCCTCCGCCTCCACCTCCTCCTCCCCCCACCCCCACGACTACGACGTGGTCATCT
GCGGCGGCACGTTGGGGCTGTTCCTGGCCACCGCGCTGCAGCTGCAGGGCTGGCGC
GTGGCCATTGTGGAGAAGCGCCTGGTGCAGGGCCGCAACCAGGAGTGGAACATCAG
CTGGGGCGAGCTGGAGGTGCTGGTGGAGCTGGGGCTGTTGAGTGAGGAGGAGCTGA
AGGGCTGCGTCATCAGCGAGTTCAACCCCATCCGCGTGGGGTTCAAGGGCGGGGAG
GACATTTGGACTCAGGATGTGCTGAACCTGGGTGTGCACCCGCGCACGCTGCTGGAC
TCGCTCAAGCGGCGCTTCCACGCCGCCGGTGGCATCATCTTTGAGAACACGGCCTTC
AAGCACGCCGACGTGCACCCGGACGGCATCAAGCTGAGCCTGGCGCCCGGCGGTGC
CGCCGCGCCCGTGGCGGTTGGCGACACCAACCGCCCCAACGGCCTAACCACCGGCG
GCGCCGCGCCCGCCCCTTCGGGCCCCGTGGCCCCTCGCTCCATGACCACACGCCTGC
TGCTGGACTGCATGGGTCACTACAGTGACATCGTCAAGCAGATCCGCGGCCGTGTGA
AGCCTGACGGCATGGTGCTGGTGGTGGGCGGCTGCGCGGAGGGCTTCCCGGCGGAG
GCCAACATCAGCGCCGACCTGCTGTACAGCCTGAGCCACGCCCGCGACGACGTGCA
GCTGTTCTGGGAGGCGTTCCCCGCGGAGGGCGGCCAGGCGCGGACCACCTACATGT
TCGCGTACAGTGACGCGCACCCGGACCGGCCCTCCTTCGAGGCGCTGCTAGACACGT
ACTTCCAGATGCTGCCCGAGTACCAGGGCATCCCGCTGGACCAGCTCAAGTTCAAGC
GTGTGCTGTTCGGCGGCTTCCCCTGCTACAGCAACGGCCCGCTGGCGCCCGCCTTTG
ACCGCGTGATGCAGATCGGCGACGCCAGCGCGGCCCAGTCGCCTCTGTCGTTCGGC
GGCTTTGGCTCCATGATGCGACACCTGCCGCGCCTGGCGCGCGGTCTGGACCAGGCG
CTGCAGGAGGACCGCCTGGCGCGACCCGACCTCAACTGGCTGCACCCCTACCAGCC
GTCCCTGTCTGCCTCGTGGCTGTTCCAGCGCTCCATGTCGTTGGCGGTTGGGCAGGT
GGCCTACCCGCCCGACTGCCCGCACGCGCCCGCCTACTACGCCGCCGCCAAGGAGG
CCAAGGCCGCCGCAGCCGCCGCGGCCGTGGACCGCGCCGAGGGCTTTGACGGCCTG
GTCTCCACCGCCGGCGAGCGCGCGCTGTCGCTTCAGGAGGCGGCGATGGAGGCGGT
GGAGGCGGTGGCGGCCCGCTTCGCCGCCGGCAGTGCCGACCCCGCCGACTACTTCC
ATGTGGAGCAGGAGGTGCCGGGAGCGGGCAGCGACCGCCGCACGCCGCAGCTGGC
CAGCGGCAAGGCGCAGCCCGCGCCGCCCAAGCTGAAGAAGAAGCTGTTTGAGCGCG
ACTTCCGTACGGCGCCGGAGTGGCAGCGCCTGCCGTACACGCACGTGAACGAGATC
CTGGGGACCAACTTCGGCGTGATGGGGGTGCTGGGCGACCGCGTGCTCAAACCCTT
CCTGCAGGACACGATCCAGCTGGTGCCGCTGTCGCTGTCCATGACCGGCATGATGCT
GTCCAACCCCGTCACCGTCAGCCGCGTGCTCATGCAGGTCGGCCCCAAGACGCTGGT
GTCCTGGTTCGCGCACTACTTTGCGCTGGTGGCCTACAGCCTGGGGCACGTGCTGCT
CAGCCCTCTGCGCGGCGTGGTGCCCTCCTACTCCTTCCAGCGCATGCTGGACGCCCT
AGAGTACGGCAGCGGCTCTGACTACCGCTACCACGCCCCGCCGGCCCGGCGGCGG
GCGCCGCCGTCTCGGCGGGCCGCGGCGCGCCCGTGGCGGCGGCGCTGAGCGCCGCT
GCACGGTCCATTGACGGCGGCGCGCAACGGAGAGCATGGATGGCGGCGATGGTGG
GGATGCGGCGGGCGAGGCCGGCGCGGCCGGGAAGAGCGAGGGCGGGTCGGTGAAG
GGGCGCAAGGCGCCCAAGCAGCAGCAGCCGGCGGCGGAGCCGATGCCCATTCCGGT
GCCGGTGGCGGCGGCGACGGCCGCGGCGGCGGCTATGGCGGCGGCGACCATGGTGG
TTGGCCTCCCAGGCATCGGCCCCGTCACCCTCGGGTGA Cre04.g221550 genomic sequence (SEQ ID NO: 3)
ATGCAGCAACGCCTTCTGAAGCCTCATACGGCCGGTCGCCCTAGCGGCGCTGTGCCT
ATCGCTCATGGTCTTGTCTCAGGGCCTCGCGTGCAGCCGGCTGCGCCCTCCGCTCGC
CCAGCGTCTGGTAATGTGACCTCACATCCAGTGGGCGCGCGCGGGCCCGCCTGCGA

| Illustrative sequences |
| --- |
| CCAGGCCAGCAGTGCTGGCAAGCGTTTCGATAGCCTAGCAGCCTACGGGCTAGCTC |
| GGGACGTGCTTACGAAGCAGGCCTCGAACATTGAGGGCAACCCCATTGAGTTCCTTG |
| ACGTGACGGAAAAGTTCTGGAGAGCGCTTCGTAACCAGAAGCATGAGCCCGAGAAG |
| AAGGGCCCCAAGGTGAGAGATGTTGCGCCAGTCTTGGAGCCGACCGTGCTGCTGAC |
| AGGCCAGTGTTTCCGGCCCTCCGCCGCGCCAAATGGCTTTAAACTTGCACATCGTAG |
| CTGCTTTTACGCCGGGCGTTTCGGCGGCTGTGTTGACGTCACGAGCGCGCGCGCGCG |
| CTCTCGGCCTCACGGCTCTCTAACTGCTCCGACCCCTCTTTACCGTTGGCCCTGCGGC |
| TCTCGCGACCTGCTGGCACGCCAGCTGTCAGCTGCCAGCTGTCCCCTGTCCCAATCC |
| CCTTGCATCCTTTTTGCTGAACCCCTCCTTCCCTTCCCCTCTCCTTCCCGCTCCTCCCT |
| CCCCTCCCGCTCCTCCCTCCCCTCCCCTCTCCTCTCCTGCCTCTCCCTCAGGTGGTCAC |
| ATACGCGGACGAGCTCCTCTTCCCAGACTCCGCCTCCTCCTCCTCCGCCTCCACCTCC |
| TCCTCCCCCCACCCCCACGACTACGACGTGGTCATCTGCGGCGGCACGTTGGGGCTG |
| TTCCTGGCCACCGCGCTGCAGCTGCAGGGCTGGCGCGTGGCCATTGTGGAGAAGCG |
| CCTGGTGCAGGTGAGGCGGCGGGGTGGGCAAGAGCGGGGGCCCAAGGAGCGGGCG |
| GGGGCGTCGGGGTGCGCGTGACGTGCCACGGACCCCCTAAAGGCACGTCTTCGTAG |
| CAGCAGCTAGCAGTAGCAGTAAACACCTGACGGTAAATCGCCTGCGGCCTGAAGTG |
| CCGGCCATTCGCTCTTGAAACTAGCCTGCGGGATGCTACAGCTGCCCTGTATCAGTC |
| CTCCATGCGGCTGCTGCTGCTGCTGCTGCTGCCTGTAACTGTTGCTGTCGCTGCTG |
| CTTCTGTCCAACAGGGCCGCAACCAGGAGTGGAACATCAGCTGGGGCGAGCTGGAG |
| GTGCTGGTGGAGCTGGGGCTGTTGAGTGAGGAGGAGCTGAAGGGCTGCGTCATCAG |
| CGAGTTCAACCCCATCCGCGTGGGGTTCAAGGGCGGGGAGGTGAGCGAGCGAGGGC |
| TTGTTACAAGGATAGGGGGAGAGAGAGGAAAGGGGGAGAAAGGTGAGAGGGGG |
| AAAGTGGGGAGGGGGTTGGGAGAGGTAAGCGGCGTGTGAGTCACGACAGGTGGGG |
| TCGGCGCAGCTATGGGGGATGGACGGAGCGCGGAGCAGCCGTGTGGCGAGGGGCC |
| GGAGAGGAGACCGGGTTACAGCGCGGAGGCCATAACATGGTAACATGGCTTGGCGG |
| AAGCAGAGTATGGCAGAAGCGGTTCCTGGCGGCTTCCAAGAAGGAGACGAAATCTA |
| GAAATCAGTCTCGCAGCATGCAGGAGTGGCTTCCTAACGCCGCATCTGTATCCTTCC |
| CGCTCCCTCTCCTCTCCTCTCCTCCTCAGGACATTTGGACTCAGGATGTGCTGAAC |
| CTGGGTGTGCACCCGCGCACGCTGCTGGACTCGCTCAAGCGGCGCTTCCACGCCGCC |
| GGTGGCATCATCTTTGAGAACACGGCCTTCAAGCACGCCGACGTGCACCCGGTGAG |
| GACAAACACTAAATGGGCTTCTTCTCTTGGGAGGGAGAGAGGGGGCGGAGGAGGCA |
| ATAGGAAAGGGCTTGGAAGGTCTGTGAGGAGGGCGCGGATGCAAACAAACACGTA |
| CCGTATGAGCATCAGAACCCATTTTGAAGGAAAGTTGAAAACTCTTCCCACCTGGAA |
| ATGATCTGTTCGTGCAGGACGGCATCAAGCTGAGCCTGGCGCCCGGCGGTGCCGCC |
| GCGCCCGTGGCGGTTGGCGACACCAACCGCCCCAACGGCCTAACCACCGGCGGCGC |
| CGCGCCCGCCCCTTCGGGCCCCGTGGCCCCTCGCTCCATGACCACACGCCTGCTGCT |
| GGACTGCATGGGTCACTACAGGTGGGGGAAGGGAGGCCGTGGAGGGATGAAGGG |
| AGGCCGTGGAGGGAGGCAGGGAAGGAGGGGCACTAAAACGCTTACACAGCAGGGT |
| TGTGGTGTTGGCGGGTTCCGAGTGTCCCAACGCACCGCGTTGCAGACTGCGATGGCG |
| TAGAATGGTTGAAGGCGCGCAGGAACGCTATCAGGCCTGTTGCGGCCAATGCACCC |
| ACAACACTTGCTCCGCTGTCCCTCCTCTCCCCCCCACGGTTTAGTTTGGGCTGGTTTT |
| AACAACCCTCCCACCGCACACACACACGTTACACACCCGCGCCCGTAGTGACATCGT |
| CAAGCAGATCCGCGGCCGTGTGAAGCCTGACGGCATGGTGCTGGTGGTGGGCGGCT |
| GCGCGGAGGGCTTCCCGGCGGAGGCCAACATCAGCGCCGACCTGCTGTACAGGTGT |
| GTGTGTGTGGGGGGGGGGGGGGGGGCTGTGTGTATGTGGGGGGGGGGGGGGTGCG |
| GATGGAGGGAGGGCGTGGGGGGGTGGGAGGGGGGGCTTGGAGAGGGGGAGGCGAC |
| TTGTAGAAACTGAAGTTGTAGGCGTGAGAGGCGTGAGTCGAGCACGAGGCGACGAA |
| AGTAACGCCGGTTGGTCTGGAGCCGACTCAGATCGGGCTTGAGCGCTTAGGCCTTCT |
| CCTCCGTGCTCAAAATCAACAGTAAGTATTATCACAATGCAATCATCATCGCAACGC |
| AACATAACCTGCTTCTCCATTATGCCTCTGCCGCCTTCACGGTCGCAGCCTGAGCCA |
| CGCCCGCGACGACGTGCAGCTGTTCTGGGAGGCGTTCCCCGCGGAGGGCGGCCAGG |
| CGCGGACCACCTACATGTTCGCGTACAGGTGAGAGAGTGAGAGAGGGGCAGAGA |
| GGAGGGGAGGAGGCAGGGGTGGGAGGGGAGGAGGCAGGGGCGGGAGGGGCGT |
| AGGTCCGCACCCACACCTGCGTGGCAGTGCACTGAACGCGCAGCGAGCAGGCCCGG |
| GCGGCGGAAGGCTTGGTCCAGGGGCAGGGACAGTGACAGGGGCAGGGGCCTTGCG |
| AGCAACACACACGCATGCACACATGCGCACACGCACCGATTCTTGGGTTTCTGAAA |
| CACACACACACACCTTTCGTTTCGTTTTTTAACACACCTCCTTCCCTCCCCTCGCAGT |
| GACGCGCACCCGGACCGGCCCTCCTTCGAGGCGCTGCTAGACACGTACTTCCAGATG |
| CTGCCCGAGTACCAGGTGGGTGGCTGGGGGGGGAGAGATCGTGTATGCGGAAGGA |
| GGACGGGGGGGGAGCGGGTTGGATGTGACTGATGTTGATGACGAGTGTTTGATGA |
| AAACACACGCGATGCGCGGGGGACACATCTTTGTATGTAACACTACCGTGTGTGTAA |
| CAAACGCGAACCCTCGTGTCGAACACCCACAGGGCATCCCGCTGGACCAGCTCAAG |
| TTCAAGCGTGTGCTGTTCGGCGGCTTCCCCTGCTACAGCAACGGCCCGCTGGCGCCC |
| GCCTTTGACCGCGTGATGCAGGTGGGCGGTGGGAATAGAGGGGATGTGGGGAGGC |
| GGGTGCGCGTGATTGTGGGTTGTGGGGAATTGGGGGGTGGAGGGGCGGGTATGC |
| GTGTAGCGTGGCATGTGGGGTGGCGTGGCAGGAGTTGTAGCGCTGGGGCTGGGGCT |
| TGGAAATACATGCCCGAGTCCAACATAATCTGAGGTCGCAGTTCTCAAGGAGGGAG |
| GGGGGCGCGGCGGGCACGCTCTGCTATCAAGCCCACCAATCCTCAATGTACAAG |
| CTTTGACACCACCAAAACAACCCAGGCTAAGCATTCCCAAAAATAATCGATTATCCC |
| GGTACCCACAACCCAAAACGCAGATCGGCGACGCCAGCGCGGCCCAGTCGCCTCTG |
| TCGTTCGGCGGCTTTGGCTCCATGATGCGACACCTGCCGCGCTGGCGCGCGCTTCTG |
| GACCAGGCGCTGCAGGAGGACCGCCTGGCGCGACCCGACCTCAACTGGCTGCACCC |
| CTACCAGGTGAGGGACGAATTGAGGGGGGGTTTGAGGAGTTGTGGGACCGGTTGC |
| ATTCATGATTGGCAACGGGAATGGGGGATTGGGGGGGGGTAGAGTTGGTGAGGG |
| AAGTTGGGTTGGAAGCGGGAGCAATTCGATGGGGGGGTTAACTCGTGGGGTTAAC |
| TTGGTTGGGGGAGATTTGGGAGTGGGACGGGGAAGGAACGAAGCGTGGGCACGT |
| ACGCACACCATCTGTCTGGCACCCGACAACGCCCTGCAATTCCGCCACTCAACTCCA |

| Illustrative sequences |
|---|
| GCACACCCACATTCCAATAAAGATCCTCACACGCGCCTCCTCCTCCCTCTCCTGTCG<br>CCGCCGCAGCCGTCCCTGTCTGCCTCGTGGCTGTTCCAGCGCTCCATGTCGTTGGCG<br>GTTGGGCAGGTGGCCTACCCGCCCGACTGCCCGCACGCGCCCGCCTACTACGCCGCC<br>GCCAAGGTGAGGAGGAGGGAGAGGGCGAGGGGCAGGGGGCGAGAGGGTGAGGGG<br>CAGGGGGGGAGAGGAGGCCGTGGGAAAGGAGAGGGCTTGGGAAGGGAGAGGGCAT<br>GGGAAGGATGAGTGTCGTGGGGGCGCGTGGGCGTGTGCGTTGAGGCTGATGCATGG<br>GTGGTAGCAGTGTGGCGTGCGGGCTTGGAATTCGCACAGGTACCGCCACTAGCGCG<br>CCCACACTGCCGCCGCCGCCTCCACCGCCTCCATCCCGCCTCCGCCCCACAACCCAC<br>CACCTCCCCGCGCCCATGGCCCGCTTGCTTATGATCTGCCACCTAGCCCCAGGCAA<br>GCCGCGCAAACGTGTGTGAAAACGGCGTTGACCTAATACGTGCGATGTGCTGTAGC<br>AACCACGCTGTCACGGCGCTTCCCACTGCACACCAAACATGCACGCCCTCCCTTCCA<br>AAACCGCCGCAATCCCTTTCCTCAACCTCACCACCCACCCTCCTCGCTCCCATCCCTC<br>CTCGCTCCCACCACAGGAGGCCAAGGCCGCCGCAGCCGCCGGGCCGTGGACCGCG<br>CCGAGGGCTTTGACGGCCTGGTCTCCACCGCCGGCGAGCGCGCGCTGTCGCTTCAGG<br>AGGCGGCGATGGAGGCGGTGGAGGCGGTGGCGGCCCGCTTCGCCGCCGGCAGTGCC<br>GACCCCGCCGACTACTTCCATGTGGAGCAGGAGGTGCCGGGAGCGGGCAGCGACCG<br>CCGCACGCCGCAGCTGGCCAGCGGCAAGGCGCAGGTGGGGCGTGTGTGTGTGTGTG<br>GGGGGGGGGGGTGGCGGGGGAGGGGGCCGGGGGAGCGGGGTGCAAAGATGGTTG<br>GAGAAGCTGTACACGAAAGGGGGGCTGGGGCAGCGGCGGCGGCAAGCCCCGAGA<br>TGGGAGAAATTGGAGGGGCCGCGGCGTAGAGACGAAGGCAAGGTGGTGGGCGGTC<br>CACATTGGCGATGCGCTGTGTGTACCTTGTGCCTTCCTAACGATCCGCACACGCACA<br>CACACCCAATACACACACGAGTGCAGCCCGCGCCGCCCAAGCTGAAGAAGAAGCTG<br>TTTGAGCGCGACTTCCGTACGGCGCCGGAGTGGCAGCGCCTGCCGTACACGCACGT<br>GAACGAGATCCTGGGGACCAACTTCGGCGTGATGGGGGTGCTGGGCGACCGCGTGC<br>TCAAACCCTTCCTGCAGGTGCGTGTGGGCGTGTGTGTGTGTGTGTGTGGGTTGGG<br>GTATGGGGGAAGTATGTGCATGTGCTTGTGAGGGTTCTGGGTTTTCCGGTTGGGAGG<br>GAAAGGGGACAGGAAAGGGATCAACCGCAACCCCTCTCACTCGCACACAAATACAC<br>GCACACACACATTCTTGTTCACTCACTCCCACTCCTTCACTCACTCTCACACACTCTC<br>TCTCTCTCTCGCTCACTCCACAGGACACGATCCAGCTGGTGCCGCTGTCGCTGTCCAT<br>GACCGGCATGATGCTGTCCAACCCCGTCACCGTCAGCCGCGTGCTCATGCAGGTGTG<br>TGTGCGCGGGTGTATGTGTGTGTGTAAGTGTATGTTGGGTCGGTGGGTGGGTGGG<br>TGGGTGGGTGGGGAAAGTAGAGAGGAGCGAGGAGGGAGGCAGGCAGGGAGGGG<br>GCGCAGCATGGAGTGGGGGAGTAAGGGAGGGATGGAAACACAAGCGAAGAGTGGC<br>CCGGGCCTGTGTCTTGTGCCCAACCTCTTCCATCCGATGATGCCTCCCATGCTCATCC<br>ATTTCCCAATTCAGCACTTACCCCAACCCACCAACCAACATCATCGCGCACCTGCTT<br>ACACACAGGTCGGCCCCAAGACGCTGGTGTCCTGGTTCGCGCACTACTTTGCGCTGG<br>TGGCCTACAGCCTGGGGCACGTGCTGCTCAGCCCTCTGCGCGGCGTGGTGCCCTCCT<br>ACTCCTTCCAGCGCATGCTGGACGCCCTAGAGTACGGCAGCGGCTCTGACTACGCT<br>ACCACGCCCCGCCGGCCCGGCGGCGGGCGCCGCCGTCTCGGCGGGCCGCGGCGCG<br>CCCGTGGCGGCGGCGCTGAGCGCCGCTGCACGGTCCATTGACGGCGGCGCGGCAAC<br>GGAGAGCATGGATGGCGGCGATGGTGGGGATGCGGCGGGCGAGGCCGGCGCGGCC<br>GGGAAGAGCGAGGGCGGGTCGGTGAAGGGGCGCAAGGCGCCCAAGCAGCAGCAGC<br>CGGCGGCGGAGCCGATGCCCATTCCGGTGCCGGTGGCGGCGGCGACGGCCGCGGCG<br>GCGGCTATGGCGGCGGCGACCATGGTGGTTGGCCTCCCAGGCATCGGCCCCGTCAC<br>CCTCGGGTGA |

Cre04.g221550 genomic sequence, with FLAG tag (SEQ ID NO: 4)
ATGCAGCAACGCCTTCTGAAGCCTCATACGGCCGGTCGCCCTAGCGGCGCTGTGCCT
ATCGCTCATGGTCTTGTCTCAGGGCCTCGCGTGCAGCCGGCTGCGCCCTCCGCTCGC
CCAGCGTCTGGTAATGTGACCTCACATCCAGTGGGCGCGCGGGCCCGCCTGCGA
CCAGGCCAGCAGTGCTGGCAAGCGTTTCGATAGCCTAGCAGCCTACGGGCTAGCTC
GGGACGTGCTTACGAAGCAGGCCTCGAACATTGAGGGCAACCCCATTGAGTTCCTTG
ACGTGACGGAAAAGTTCTGGAGAGCGCTTCGTAACCAGAAGCATGAGCCCCGAGAAG
AAGGGCCCCAAGGTGAGAGATGTTGCGCCAGTCTTGGAGCCGACCGTGCTGCTGAC
AGGCCAGTGTTTCCGGCCCTCCGCCGCGCCAAATGGCTTTAAACTTGCACATCGTAG
CTGCTTTTACGCCGGGCGTTTCGGCGGCTGTGTTGACGTCACGAGCGCGCGCGCGCG
CTCTCGGCCTCACGGCTCTCTAACTGCTCCGACCCCTCTTTACCGTTGGCCCTGCGGC
TCTCGCGACCTGCTGGCACGCCAGCTGTCAGCTGCCAGCTGTCCCCTGTCCCAATCC
CCTTGCATCCTTTTTGCTGAACCCCTCCTTCCCTTCCCCTCTCCTTCCCGCTCCTCCCT
CCCCTCCCGCTCCTCCCTCCCCTCCCCTCTCCTCCTGCCTCTCCCTCAGGTGGTCAC
ATACGCGGACGAGCTCCTCTTCCCAGACTCCGCCTCCTCCTCCTCCGCCTCCACCTCC
TCCTCCCCCCACCCCCACGACTACGACGTGGTCATCTGCGGCGGCACGTTGGGGCTG
TTCCTGGCCACCGCGCTGCAGCTGCAGGGCTGGCGCGTGGCCATTGTGGAGAAGCG
CCTGGTGCAGGTGAGGCGGCGGGGTGGGCAAGAGCGGGGCCCAAGGAGCGGGCG
GGGGCGTCGGGGTGCGCGTGACGTGCCACGGACCCCCTAAAGGCACGTCTTCGTAG
CAGCAGCTAGCAGTAGCAGTAAACACCTGACGGTAAATCGCCTGCGGCCTGAAGTG
CCGGCCATTCGCTCTTGAAACTAGCCTGCGGGATGCTACAGCTGCCCTGTATCAGTC
CTCCATGCGGCTGCTGCTGCTGCTGCTGCTCCTGTAACTGTTGCTGTCGCTGCTG
CTTCTGTCCAACAGGGCCGCAACCAGGAGTGGAACATCAGCTGGGGCGAGCTGGAG
GTGCTGGTGGAGCTGGGGCTGTTGAGTGAGGAGGAGCTGAAGGGCTGCGTCATCAG
CGAGTTCAACCCCATCCGCGTGGGGTTCAAGGGCGGGAGGTGAGCGAGCGAGGGC
TTGTTACAAGGATAGGGGGAGAGAGAGGAAAGGGGGAGAAAGGTGAGAGGGGG
AAAGTGGGAGGGGTTGGGAGAGGTAAGCGGCGTGTGAGTCACGACAGGTGGGG
TCGGCGCAGCTATGGGGATGGACGGAGCGCGGAGCAGCCGTGTGGCGAGGGGCC
GGAGAGGAGACCGGGTTACAGCGCGGAGGCCATAACATGGTAACATGGCTTGGCGG
AAGCAGAGTATGGCAGAAGCGGTTCCTGGCGGCTTCCAAGAAGGAGACGAAATCTA
GAAATCAGTCTCGCAGCATGCAGGAGTGGCTTCCTAACGCCGCATCTGTATCCTTCC -continued

| Illustrative sequences |
|---|
| CGCTCCCTCTCCTCTCCTCTCCTCTCCTCAGGACATTTGGACTCAGGATGTGCTGAAC |
| CTGGGTGTGCACCCGCGCACGCTGCTGGACTCGCTCAAGCGGCGCTTCCACGCCGCC |
| GGTGGCATCATCTTTGAGAACACGGCCTTCAAGCACGCCGACGTGCACCCGGTGAG |
| GACAAACACTAAATGGGCTTCTTCTCTTGGGAGGGAGAGAGGGGGCGGAGGAGGCA |
| ATAGGAAAGGGCTTGGAAGGTCTGTGAGGAGGGCGCGGATGCAAACAAACACGTA |
| CCGTATGAGCATCAGAACCCATTTTGAAGGAAAGTTGAAAACTCTTCCCACCTGGAA |
| ATGATCTGTTCGTGCAGGACGGCATCAAGCTGAGCCTGGCGCCCGGCGGTGCCGCC |
| GCGCCCGTGGCGGTTGGCGACACCAACCGCCCCAACGGCCTAACCACCGGCGGCGC |
| CGCGCCCGCCCCTTCGGGCCCCGTGGCCCCTCGCTCCATGACCACACGCCTGCTGCT |
| GGACTGCATGGGTCACTACAGGTGGGGGGAAGGGAGGCCGTGGAGGGATGAAGGG |
| AGGCCGTGGAGGGAGGCAGGGAAGGAGGGGCACTAAAACGCTTACACAGCAGGGT |
| TGTGGTGTTGGCGGGTTCCGAGTGTCCCAACGCACCGCGTTGCAGACTGCGATGGCG |
| TAGAATGGTTGAAGGCGCGCAGGAACGCTATCAGGCCTGTTGCGGCCAATGCACCC |
| ACAACACTTGCTCCGCTGTCCCTCCTCTCCCCCCCACGGTTTAGTTTGGGCTGGTTTT |
| AACAACCCTCCCACCGCACACACACACGTTACACACCCGCGCCCGTAGTGACATCGT |
| CAAGCAGATCCGCGGCCGTGTGAAGCCTGACGGCATGGTGCTGGTGGTGGGCGGCT |
| GCGCGGAGGGCTTCCCGGCGGAGGCCAACATCAGCGCCGACCTGCTGTACAGGTGT |
| GTGTGTGTGGGGGGGGGGGGGGGGGCTGTGTGTATGTGGGGGGGGGGGTGCG |
| GATGGAGGGAGGGCGTGGGGGGGTGGGAGGGGGGGCTTGGAGAGGGGGAGGCGAC |
| TTGTAGAAACTGAAGTTGTAGGCGTGAGAGGCGTGAGTCGAGCACGAGGCGACGAA |
| AGTAACGCCGGTTGGTCTGGAGCCGACTCAGATCGGGCTTGAGCGCTTAGGCCTTCT |
| CCTCCGTGCTCAAAATCAACAGTAAGTATTATCACAATGCAATCATCATCGCAACGC |
| AACATAACCTGCTTCTCCATTATGCCTCTGCCGCCTTCACGGTCGCAGCCTGAGCCA |
| CGCCCGCGACGACGTGCAGCTGTTCTGGGAGGCGTTCCCCGCGGAGGGCGGCCAGG |
| CGCGGACCACCTACATGTTCGCGTACAGGTGAGAGAGTGAGAGAGGGGGCAGAGA |
| GGAGGGGAGGAGCAGGGGTGGGGAGGGGAGGAGGCAGGGGCGGGGAGGGCCGT |
| AGGTCCGCACCCACACCTGCGTGGCAGTGCACTGAACGCGCAGCGAGCAGGCCCGG |
| GCGGCGGAAGGCTTGGTCCAGGGGCAGGGACAGTGACAGGGGCAGGGGCCTTGCG |
| AGCAACACACACGCATGCACACATGCGCACACGCACCGATTCTTGGGTTTCTGAAA |
| CACACACACACACCTTTCGTTTCGTTTTTTAACACACCTCCTTCCCTCCCCTCGCAGT |
| GACGCGCACCCGGACCGGCCCTCCTTCGAGGCGCTGCTAGACACGTACTTCCAGATG |
| CTGCCCGAGTACCAGGTGGGTGGCTGGGGGGGGAGAGATCGTGTATGCGGAAGGA |
| GGACGGGGGGGGAGCGGGTTGGATGTGACTGATGTTGATGACGAGTGTTTGATGA |
| AAACACACGCGATGCGCGGGGGACACATCTTTGTATGTAACACTACCGTGTGTGTAA |
| CAAACGCGAACCCTCGTGTCGAACACCCACAGGGCATCCCGCTGGACCAGCTCAAG |
| TTCAAGCGTGTGCTGTTCGGCGGCTTCCCCTGCTACAGCAACGGCCGCTGGCGCCC |
| GCCTTTGACCGCGTGATGCAGGTGGGCGGTGGGAATAGAGGGGATGTGGGGGAGGC |
| GGGTGCGCGTGATTGTGGGTTGTGGGGAATTGGGGGGGTGGAGGGGCGGGGTATGC |
| GTGTAGCGTGGCATGTGGGGTGGCGTGGCAGGAGTTGTAGCGCTGGGGCTGGGGCT |
| TGGAAATACATGCCCGAGTCCAACATAATCTGAGGTCGCAGTTCTCAAGGAGGGAG |
| GGGGGGCGCGGCGGGCCACGCTCTGCTATCAAGCCCACCAATCCTCAATGTACAAG |
| CTTTGACACCACCAAAACAACCCAGGCTAAGCATTCCCAAAAATAATCGATTATCCC |
| GGTACCCACAACCCAAAACGCAGATCGGCGACGCCAGCGCGGCCCAGTCGCCTCTG |
| TCGTTCGGCGGCTTTGGCTCCATGATGCGACACCTGCCGCGCCTGGCGCGCGGTCTG |
| GACCAGGCGCTGCAGGAGGACCGCCTGGCGCGACCCGACCTCAACTGGCTGCACCC |
| CTACCAGGTGAGGGACGAATTGAGGGGGGGTTTGAGGAGTTGTGGGGACCGGTTGC |
| ATTCATGATTGGCAACGGGAATGGGGGATTGGGGGGGGGGTAGAGTTGGTGAGGG |
| AAGTTGGGTTGGAAGCGGGAGCAATTCGATGGGGGGGGTTAACTCGTGGGGTTAAC |
| TTGGTTGGGGGAGATTTGGGAGTGGGGACGGGGAAGGAACGAAGCGTGGGCACGT |
| ACGCACACCATCTGTCTGGCACCCGACAACGCCCTGCAATTCCGCCACTCAACTCCA |
| GCACACCCACATTCCAATAAAGATCCTCACACGCGCCTCCTCCTCCCTCTCCTGTCG |
| CCGCCGCAGCCGTCCCTGTCTGCCTCGTGGCTGTTCCAGCGCTCCATGTCGTTGGCG |
| GTTGGGCAGGTGGCCTACCCGCCCGACTGCCCGCACGCGCCCGCCTACTACGCCGCC |
| GCCAAGGTGAGGAGGAGGGAGAGGGCGAGGGGCAGGGGCGAGAGGGTGAGGGG |
| CAGGGGGGAGAGGAGGCCGTGGGAAAGGAGAGGGCTTGGGAAGGGAGAGGGCAT |
| GGGAAGGATGAGTGTCGTGGGGCGCGTGGGCGTGTGCGTTGAGGCTGATGCATGG |
| GTGGTAGCAGTGTGGCGTGCGGGCTTGGAATTCGCACAGGTACCGCCACTAGCGCG |
| CCCACACTGCCGCCGCCGCCTCCACCGCCTCCATCCCGCCTCCGCCCCACAACCCAC |
| CACCTCCCCGCGCCCCATGGCCCGCTTGCTTATGATCTGCCACCTAGCCCCAGGCAA |
| GCCGCGCAAACGTGTGTGAAAACGGCGTTGACCTAATACGTGCGATGTGCTGTAGC |
| AACCACGCTGTCACGGCGCTTCCCACTGCACACCAAACATGCACGCCTCCCTTCCA |
| AAACCGCCGCAATCCCTTTCCTCAACCTCACCACCCACCCTCCTCGCTCCCATCCCTC |
| CTCGCTCCCACCACAGGAGGCCAAGGCCGCCGCAGCCGCCGGCCGTGGACCGCG |
| CCGAGGGCTTTGACGGCCTGGTCTCCACCGCCGGCGAGCGCGCGTGTCGCTTCAGG |
| AGGCGGCGATGGAGGCGGTGGAGGCGGTGGCGGCCCGCTTCGCCGCCGGCAGTGCC |
| GACCCCGCCGACTACTTCCATGTGGAGCAGGAGGTGCCGGGAGCGGGCAGCGACCG |
| CCGCACGCCGCAGCTGGCCAGCGGCAAGGCGCAGGTGGGGCGTGTGTGTGTGTGTG |
| GGGGGGGGGGGTGGCGGGGAGGGGGCCGGGGAGCGGGGTGCAAAGATGGTTG |
| GAGAAGCTGTACACGAAGGGGGGCTGGGCAGCGGCGGCGGCAAGCCCCGAGA |
| TGGGAGAAATTGGAGGGGCCGCGGCGTAGAGACGAAGGCAAGGTGGTGGGCGGTC |
| CACATTGGCGATGGCGTGTGTGTACCTTGTGCCTTCCTAACGATCCGCACACGCACA |
| CACACCCAATACACACACGAGTGCAGCCCGCGCCGCCCAAGCTGAAGAAGAAGCTG |
| TTTGAGCGCGACTTCCGTACGGCGCCGGAGTGGCAGCGCCTGCCGTACACGCACGT |
| GAACGAGATCCTGGGGACCAACTTCGCGTGATGGGGTGCTGGGCGACCGCGTGC |
| TCAAACCCTTCCTGCAGGTGCGTGGGCGTGTGTGTGTGTGTGTGGGTTGGG |
| GTATGGGGAAGTATGTGCATGTGCTTGTGAGGGTTCTGGGTTTTCCGGTTGGGAGG |
| GAAAGGGGACAGGAAAGGGATCAACCGCAACCCCTCTCACTCGCACACAAATACAC |

-continued

Illustrative sequences

GCACACACACATTCTTGTTCACTCACTCCCACTCCTTCACTCACTCTCACACACTCTC
TCTCTCTCTCGCTCACTCCACAGGACACGATCCAGCTGGTGCCGCTGTCGCTGTCCAT
GACCGGCATGATGCTGTCCAACCCCGTCACCGTCAGCCGCGTGCTCATGCAGGTGTG
TGTGCGCGGGTGTATGTGTGTGTGTAAGTGTATGTTGGGTCGGTGGGTGGGTGGG
TGGGTGGGTGGGGGAAAGTAGAGAGGAGCGAGGAGGGAGGCAGGCAGGGAGGGG
GCGCAGCATGGAGTGGGGGAGTAAGGGAGGGATGGAAACACAAGCGAAGAGTGGC
CCGGGCCTGTGTCTTGTGCCCAACCTCTTCCATCCGATGATGCCTCCCATGCTCATCC
ATTTCCCAATTCAGCACTTACCCCAACCCACCAACCAACATCATCGCGCACCTGCTT
ACACACAGGTCGGCCCCAAGACGCTGGTGTCCTGGTTCGCGCACTACTTTGCGCTGG
TGGCCTACAGCCTGGGGCACGTGCTGCTCAGCCCTCTGCGCGGCGTGGTGCCCTCCT
ACTCCTTCCAGCGCATGCTGGACGCCCTAGAGTACGGCAGCGGCTCTGACTACCGCT
ACCACGCCCCGCCGGCCCGGCGGCGGGCGCCGCCGTCTCGGCGGGCCGCGGCGCG
CCCGTGGCGGCGGCGCTGAGCGCCGCTGCACGGTCCATTGACGGCGGCGCGGCAAC
GGAGAGCATGGATGGCGGCGATGGTGGGGATGCGGCGGGCGAGGCCGGCGCGGCC
GGGAAGAGCGAGGGCGGGTCGGTGAAGGGGCGCAAGGCGCCCAAGCAGCAGCAGC
CGGCGGCGGAGCCGATGCCCATTCCGGTGCCGGTGGCGGCGGCGACGGCCGCGGCG
GCGGCTATGGCGGCGGCGACCATGGTGGTTGGCCTCCCAGGCATCGGCCCCGTCAC
CCTCGGCggcGACTACAAGGACGATGACGACAAGTGATGA Codon-optimized Cre04.g221550 for expression in Arabidopsis,
without tag (SEQ ID NO: 5)
ATGCAGCAAAGATTACTCAAGCCTCACACAGCAGGTAGACCAAGTGGAGCAGTTCC
TATCGCACACGGACTCGTTAGTGGACCAAGAGTTCAACCTGCTGCACCAAGTGCAA
GACCTGCTTCTGGAAATGTTACTTCACATCCTGTGGGAGCAAGGGGGCCCGCATGCG
ATCAAGCATCTTCAGCTGGAAAGAGATTTGATTCATTGGCTGCTTATGGACTCGCTA
GGGATGTTTTAACCAAGCAGGCTTCTAATATCGAGGGTAACCCAATAGAATTTTTGG
ATGTGACTGAGAAGTTCTGGAGAGCTCTCAGGAACCAGAAACACGAGCCTGAAAAG
AAAGGACCAAAGGTTGTGACTTATGCTGATGAACTTTTGTTTCCTGATTCTGCAAGT
TCTTCAAGTGCTTCAACCTCTTCAAGTCCTCATCCACACGATTACGATGTTGTGATTT
GTGGAGGTACTTTAGGTCTTTTCTTGGCAACAGCTCTCCAGTTACAAGGATGGAGAG
TTGCTATAGTGGAGAAAAGACTTGTTCAGGGTAGGAATCAAGAGTGGAATATTTCTT
GGGGAGAGCTTGAAGTTTTGGTGGAGCTCGGTCTCTTATCAGAAGAGGAATTGAAA
GGATGCGTTATTTCTGAGTTTAATCCAATCAGAGTGGGTTTCAAGGGAGGTGAAGAT
ATATGGACTCAAGATGTTCTTAACTTGGGAGTGCATCCTAGGACACTTTTGGATTCA
CTTAAGAGAAGGTTCCACGCTGCAGGAGGTATTATCTTCGAAAACACCGCATTCAAA
CATGCTGATGTTCACCCAGATGGAATCAAGCTCTCTTTAGCTCCTGAGGTGCTGCA
GCTCCAGTTGCTGTGGGAGATACAAATAGACCTAACGGTCTTACTACAGGAGGTGC
AGCTCCTGCACCAAGTGGTCCTGTTGCTCCAAGATCAATGACCACTAGGCTCTTACT
TGATTGTATGGGACATTACTCTGATATAGTTAAGCAAATAAGAGGAAGGGTTAAAC
CAGATGGTATGGTGTTGGTTGTGGGAGGTTGCGCTGAGGGTTTTCCTGCAGAAGCTA
ACATCTCTGCTGATTTGCTCTACTCTCTCACATGCTAGAGATGATGTTCAATTATT
TTGGGAGGCATTCCCAGCTGAAGGTGGTCAGGCTAGAACAACCTATATGTTCGCATA
CTCTGATGCTCACCCTGATAGGCCATCATTTGAGGCTTTACTTGATACTTACTTCCAG
ATGCTTCCTGAATACCAAGGTATTCCTCTTGATCAGCTTAAGTTTAAGAGAGTTCTTT
TTGGAGGTTTCCCTTGTTACTCTAATGGTCCTTTGGCACCAGCTTTCGATAGGGTTAT
GCAAATCGGAGATGCTTCAGCAGCTCAGTCACCATTGAGTTTTGGAGGTTTCGGTTC
TATGATGAGACATTTGCCTAGACTCGCTAGGGGATTAGATCAGGCTCTTCAAGAGGA
TAGATTGGCTAGGCCTGATCTTAACTGGCTTCACCCTTATCAACCAAGTCTTTCTGCT
TCATGGTTGTTTCAAAGAAGTATGTCTCTCGCAGTTGGTCAGGTGGCTTACCCTCCA
GATTGCCCTCATGCACCAGCTTATTACGCAGCTGCAAAAGAGGCTAAGGCTGCAGCT
GCAGCTGCAGCTGTTGATAGAGCTGAAGGATTCGATGGTTTGGTGAGTACAGCAGG
AGAGAGGGCTCTTTCTTTGCAAGAAGCAGCTATGGAGGCAGTTGAAGCTGTGGCAG
CTAGATTTGCAGCTGGATCTGCAGATCCTGCTGATTATTTCCATGTTGAGCAGGAAG
TGCCTGGAGCTGGTTCAGATAGAAGGACTCCACAACTTGCTAGTGGAAAGGCACAG
CCTGCTCCTCCAAAATTGAAGAAAAAGCTCTTTGAGAGAGATTTCAGGACAGCTCCT
GAATGGCAAAGACTCCCATACACCCACGTTAATGAGATCCTTGGAACTAACTTTGGA
GTTATGGGTGTGTTGGGAGATAGAGTTTTAAAACCATTCTTTCAGGATACTATACAA
CTCGTGCCTCTCTCATTAAGTATGACTGGTATGATGCTTTCAAATCCAGTTACCGTGA
GTAGAGTTCTTATGCAAGTGGGACCTAAGACATTGGTTTCTTGGTTTGCTCATTATTT
CGCACTCGTTGCTTACTCATTAGGTCACGTGTTGCTCAGTCCTCTTAGAGGAGTTGTG
CCATCTTATTCATTTCAGAGGATGTTGGATGCTCTCGAATACGGAAGTGGTTCTGATT
ATAGATACCATGCACCTGCTGGACCAGCAGCTGGTGCAGCTGTTTCAGCAGGAAGA
GGTGCTCCTGTGGCAGCTGCATTGAGTGCTGCAGCTAGGTCTATTGATGGAGGTGCA
GCTACTGAGTCTATGGATGGAGGAGATGGAGGAGATGCAGCTGGAGAGGCTGGAGC
AGCTGGTAAATCTGAAGGAGGTTCAGTTAAAGGAAGAAAGGCTCCTAAACAACAGC
AACCAGCAGCTGAACCTATGCCAATCCCTGTTCCAGTGGCAGCTGCAACTGCTGCAG
CTGCAGCTATGGCTGCTGCTACTATGGTTGTGGGATTGCCTGGTATCGGACCTGTTA
CTCTCGGATGA Codon-optimized Cre04.g221550 for expression in Arabidopsis,
with FLAG tag (SEQ ID NO: 6)
ATGCAGCAAAGATTACTCAAGCCTCACACAGCAGGTAGACCAAGTGGAGCAGTTCC
TATCGCACACGGACTCGTTAGTGGACCAAGAGTTCAACCTGCTGCACCAAGTGCAA
GACCTGCTTCTGGAAATGTTACTTCACATCCTGTGGGAGCAAGGGGGCCCGCATGCG
ATCAAGCATCTTCAGCTGGAAAGAGATTTGATTCATTGGCTGCTTATGGACTCGCTA
GGGATGTTTTAACCAAGCAGGCTTCTAATATCGAGGGTAACCCAATAGAATTTTTGG
ATGTGACTGAGAAGTTCTGGAGAGCTCTCAGGAACCAGAAACACGAGCCTGAAAAG

Illustrative sequences

```
AAAGGACCAAAGGTTGTGACTTATGCTGATGAACTTTTGTTTCCTGATTCTGCAAGT
TCTTCAAGTGCTTCAACCTCTTCAAGTCCTCATCCACACGATTACGATGTTGTGATTT
GTGGAGGTACTTTAGGTCTTTTCTTGGCAACAGCTCTCCAGTTACAAGGATGGAGAG
TTGCTATAGTGGAGAAAAGACTTGTTCAGGGTAGGAATCAAGAGTGGAATATTTCTT
GGGGAGAGCTTGAAGTTTTGGTGGAGCTCGGTCTCTTATCAGAAGAGGAATTGAAA
GGATGCGTTATTTCTGAGTTTAATCCAATCAGAGTGGGTTTCAAGGGAGGTGAAGAT
ATATGGACTCAAGATGTTCTTAACTTGGGAGTGCATCCTAGGACACTTTTGGATTCA
CTTAAGAGAAGGTTCCACGCTGCAGGAGGTATTATCTTCGAAAACACCGCATTCAAA
CATGCTGATGTTCACCCAGATGGAATCAAGCTCTCTTTAGCTCCTGGAGGTGCTGCA
GCTCCAGTTGCTGTGGGAGATACAAATAGACCTAACGGTCTTACTACAGGAGGTGC
AGCTCCTGCACCAAGTGGTCCTGTTGCTCCAAGATCAATGACCACTAGGCTCTTACT
TGATTGTATGGGACATTACTCTGATATAGTTAAGCAAATAAGAGGAAGGGTTAAAC
CAGATGGTATGGTGTTGGTTGTGGGAGGTTGCGCTGAGGGTTTTCCTGCAGAAGCTA
ACATCTCTGCTGATTTGCTCTACTCTCTCACATGCTAGAGATGATGTTCAATTATT
TTGGGAGGCATTCCCAGCTGAAGGTGGTCAGGCTAGAACAACCTATATGTTCGCATA
CTCTGATGCTCACCCTGATAGGCCATCATTTGAGGCTTTACTTGATACTTACTTCCAG
ATGCTTCCTGAATACCAAGGTATTCCTCTTGATCAGCTTAAGTTTAAGAGAGTTCTTT
TTGGAGGTTTCCCTTGTTACTCTAATGGTCCTTTGGCACCAGCTTTCGATAGGGTTAT
GCAAATCGGAGATGCTTCAGCAGCTCAGTCACCATTGAGTTTTGGAGGTTTCGGTTC
TATGATGAGACATTTGCCTAGACTCGCTAGGGGATTAGATCAGGCTCTTCAAGAGGA
TAGATTGGCTAGGCCTGATCTTAACTGGCTTCACCCTTATCAACCAAGTCTTTCTGCT
TCATGGTTGTTTCAAAGAAGTATGTCTCTCGCAGTTGGTCAGGTGGCTTACCCTCCA
GATTGCCCTCATGCACCAGCTTATTACGCAGCTGCAAAAGAGGCTAAGGCTGCAGCT
GCAGCTGCAGCTGTTGATAGAGCTGAAGGATTCGATGGTTTGGTGAGTACAGCAGG
AGAGAGGGCTCTTTCTTTGCAAGAAGCAGCTATGGAGGCAGTTGAAGCTGTGGCAG
CTAGATTTGCAGCTGGATCTGCAGATCCTGCTGATTATTTCCATGTTGAGCAGGAAG
TGCCTGGAGCTGGTTCAGATAGAAGGACTCCACAACTTGCTAGTGGAAAGGCACAG
CCTGCTCCTCCAAAATTGAAGAAAAAGCTCTTTGAGAGAGATTTCAGGACAGCTCCT
GAATGGCAAAGACTCCCATACACCCACGTTAATGAGATCCTTGGAACTAACTTTGGA
GTTATGGGTGTGTTGGGAGATAGAGTTTTAAAACCATTCCTTCAGGATACTATACAA
CTCGTGCCTCTCTCATTAAGTATGACTGGTATGATGCTTTCAAATCCAGTTACCGTGA
GTAGAGTTCTTATGCAAGTGGGACCTAAGACATTGGTTTCTTGGTTTGCTCATTATTT
CGCACTCGTTGCTTACTCATTAGGTCACGTGTTGCTCAGTCCTCTTAGAGGAGTTGTG
CCATCTTATTCATTTCAGAGGATGTTGGATGCTCTCGAATACGGAAGTGGTTCTGATT
ATAGATACCATGCACCTGCTGGACCAGCAGCTGGTGCAGCTGTTTCAGCAGGAAGA
GGTGCTCCTGTGGCAGCTGCATTGAGTGCTGCAGCTAGGTCTATTGATGGAGGTGCA
GCTACTGAGTCTATGGATGGAGGAGATGGAGGAGATGCAGCTGGAGAGGCTGGAGC
AGCTGGTAAATCTGAAGGAGGTTCAGTTAAAGGAAGAAAGGCTCCTAAACAACAGC
AACCAGCAGCTGAACCTATGCCAATCCCTGTTCCAGTGGCAGCTGCAACTGCTGCAG
CTGCAGCTATGGCTGCTGCTACTATGGTTGTGGGATTGCCTGGTATCGGACCTGTTA
CTCTCGGAggcGATTATAAGGATGATGATGATAAGTGA Codon-optimized Cre04.g221550 for expression in Arabidopsis,
with Arabidopsis PsbS CTP but without FLAG tag (SEQ ID NO: 7)
ATGGCTCAAACCATGCTGCTTACTTCAGGCGTCACCGCCGGCCATTTTTTGAGGAAC
AAGAGCCCTTTGGCTCAGCCCAAAGTTCACCATCTCTTCCTCTCTGGAAACTCTCCG
GTTGCACTACCATCTAGGAGACAATCATTCGTTCCTCTCGCTCTCTTCGATCAAGCAT
CTTCAGCTGGAAAGAGATTTGATTCATTGGCTGCTTATGGACTCGCTAGGGATGTTT
TAACCAAGCAGGCTTCTAATATCGAGGGTAACCCAATAGAATTTTTGGATGTGACTG
AGAAGTTCTGGAGAGCTCTCAGGAACCAGAAACACGAGCCTGAAAAGAAAGGACC
AAAGGTTGTGACTTATGCTGATGAACTTTTGTTTCCTGATTCTGCAAGTTCTTCAAGT
GCTTCAACCTCTTCAAGTCCTCATCCACACGATTACGATGTTGTGATTTGTGGAGGTA
CTTTAGGTCTTTTCTTGGCAACAGCTCTCCAGTTACAAGGATGGAGAGTTGCTATAG
TGGAGAAAAGACTTGTTCAGGGTAGGAATCAAGAGTGGAATATTTCTTGGGGAGAG
CTTGAAGTTTTGGTGGAGCTCGGTCTCTTATCAGAAGAGGAATTGAAAGGATGCGTT
ATTTCTGAGTTTAATCCAATCAGAGTGGGTTTCAAGGGAGGTGAAGATATATGGACT
CAAGATGTTCTTAACTTGGGAGTGCATCCTAGGACACTTTTGGATTCACTTAAGAGA
AGGTTCCACGCTGCAGGAGGTATTATCTTCGAAAACACCGCATTCAAACATGCTGAT
GTTCACCCAGATGGAATCAAGCTCTCTTTAGCTCCTGGAGGTGCTGCAGCTCCAGTT
GCTGTGGGAGATACAAATAGACCTAACGGTCTTACTACAGGAGGTGCAGCTCCTGC
ACCAAGTGGTCCTGTTGCTCCAAGATCAATGACCACTAGGCTCTTACTTGATTGTAT
GGGACATTACTCTGATATAGTTAAGCAAATAAGAGGAAGGGTTAAACCAGATGGTA
TGGTGTTGGTTGTGGGAGGTTGCGCTGAGGGTTTTCCTGCAGAAGCTAACATCTCTG
CTGATTTGCTCTACTCTCTCACATGCTAGAGATGATGTTCAATTATTTTGGGAGGC
ATTCCCAGCTGAAGGTGGTCAGGCTAGAACAACCTATATGTTCGCATACTCTGATGC
TCACCCTGATAGGCCATCATTTGAGGCTTTACTTGATACTTACTTCCAGATGCTTCCT
GAATACCAAGGTATTCCTCTTGATCAGCTTAAGTTTAAGAGAGTTCTTTTTGGAGGTT
TCCCTTGTTACTCTAATGGTCCTTTGGCACCAGCTTTCGATAGGGTTATGCAAATCGG
AGATGCTTCAGCAGCTCAGTCACCATTGAGTTTTGGAGGTTTCGGTTCTATGATGAG
ACATTTGCCTAGACTCGCTAGGGGATTAGATCAGGCTCTTCAAGAGGATAGATTGGC
TAGGCCTGATCTTAACTGGCTTCACCCTTATCAACCAAGTCTTTCTGCTTCATGGTTG
TTTCAAAGAAGTATGTCTCTCGCAGTTGGTCAGGTGGCTTACCCTCCAGATTGCCCTC
ATGCACCAGCTTATTACGCAGCTGCAAAAGAGGCTAAGGCTGCAGCTGCAGCTGCA
GCTGTTGATAGAGCTGAAGGATTCGATGGTTTGGTGAGTACAGCAGGAGAGAGGGC
TCTTTCTTTGCAAGAAGCAGCTATGGAGGCAGTTGAAGCTGTGGCAGCTAGATTTGC
AGCTGGATCTGCAGATCCTGCTGATTATTTCCATGTTGAGCAGGAAGTGCCTGGAGC
TGGTTCAGATAGAAGGACTCCACAACTTGCTAGTGGAAAGGCACAGCCTGCTCCTCC
```

| Illustrative sequences |
|---|
| AAAATTGAAGAAAAAGCTCTTTGAGAGAGATTTCAGGACAGCTCCTGAATGGCAAA
GACTCCCATACACCCACGTTAATGAGATCCTTGGAACTAACTTTGGAGTTATGGGTG
TGTTGGGAGATAGAGTTTTAAAACCATTCCTTCAGGATACTATACAACTCGTGCCTC
TCTCATTAAGTATGACTGGTATGATGCTTTCAAATCCAGTTACCGTGAGTAGAGTTCT
TATGCAAGTGGGACCTAAGACATTGGTTTCTTGGTTTGCTCATTATTTCGCACTCGTT
GCTTACTCATTAGGTCACGTGTTGCTCAGTCCTCTTAGAGGAGTTGTGCCATCTTATT
CATTTCAGAGGATGTTGGATGCTCTCGAATACGAAGTGGTTCTGATTATAGATACC
ATGCACCTGCTGGACCAGCAGCTGGTGCAGCTGTTTCAGCAGGAAGAGGTGCTCCTG
TGGCAGCTGCATTGAGTGCTGCAGCTAGGTCTATTGATGGAGGTGCAGCTACTGAGT
CTATGGATGGAGGAGATGGAGGAGATGCAGCTGGAGAGGCTGGAGCAGCTGGTAA
ATCTGAAGGAGGTTCAGTTAAAGGAAGAAAGGCTCCTAAACAACAGCAACCAGCAG
CTGAACCTATGCCAATCCCTGTTCCAGTGGCAGCTGCAACTGCTGCAGCTGCAGCTA
TGGCTGCTGCTACTATGGTTGTGGGATTGCCTGGTATCGGACCTGTTACTCTCGGATG
A Codon-optimized Cre04.g221550 for expression in *Arabidopsis*,
with both *Arabidopsis* PsbS CTP and FLAG tag (SEQ ID NO: 8)
ATGGCTCAAACCATGCTGCTTACTTCAGGCGTCACCGCCGGCCATTTTTTGAGGAAC
AAGAGCCCTTTGGCTCAGCCCAAAGTTCACCATCTCTTCCTCTCTGGAAACTCTCCG
GTTGCACTACCATCTAGGAGACAATCATTCGTTCCTCTCGCTCTCTTCGATCAAGCAT
CTTCAGCTGGAAAGAGATTTGATTCATTGGCTGCTTATGGACTCGCTAGGGATGTTT
TAACCAAGCAGGCTTCTAATATCGAGGGTAACCCAATAGAATTTTTGGATGTGACTG
AGAAGTTCTGGAGAGCTCTCAGGAACCAGAAACACGAGCCTGAAAAGAAAGGACC
AAAGGTTGTGACTTATGCTGATGAACTTTTGTTTCCTGATTCTGCAAGTTCTTCAAGT
GCTTCAACCTCTTCAAGTCCTCATCCACACGATTACGATGTTGTGATTTGTGGAGGTA
CTTTAGGTCTTTTCTTGGCAACAGCTCTCCAGTTACAAGGATGGAGAGTTGCTATAG
TGGAGAAAAGACTTGTTCAGGGTAGGAATCAAGAGTGGAATATTTCTTGGGGAGAG
CTTGAAGTTTTGGTGGAGCTCGGTCTCTTATCAGAAGAGGAATTGAAAGGATGCGTT
ATTTCTGAGTTTAATCCAATCAGAGTGGGTTTCAAGGGAGGTGAAGATATATGGACT
CAAGATGTTCTTAACTTGGGAGTGCATCCTAGGACACTTTTGGATTCACTTAAGAGA
AGGTTCCACGCTGCAGGAGGTATTATCTTCGAAAACACCGCATTCAAACATGCTGAT
GTTCACCCAGATGGAATCAAGCTCTCTTTAGCTCCTGGAGGTGCTGCAGCTCCAGTT
GCTGTGGGAGATACAAATAGACCTAACGGTCTTACTACAGGAGGTGCAGCTCCTGC
ACCAAGTGGTCCTGTTGCTCCAAGATCAATGACCACTAGGCTCTTACTTGATTGTAT
GGGACATTACTCTGATATAGTTAAGCAAATAAGAGGAAGGGTTAAACCAGATGGTA
TGGTGTTGGTTGTGGGAGGTTGCGCTGAGGGTTTTCCTGCAGAAGCTAACATCTCTG
CTGATTTGCTCTACTCTCTCTCACATGCTAGAGATGATGTTCAATTATTTTGGGAGGC
ATTCCCAGCTGAAGGTGGTCAGGCTAGAACAACCTATATGTTCGCATACTCTGATGC
TCACCCTGATAGGCCATCATTTGAGGCTTTACTTGATACTTACTTCCAGATGCTTCCT
GAATACCAAGGTATTCCTCTTGATCAGCTTAAGTTTAAGAGAGTTCTTTTTGGAGGTT
TCCCTTGTTACTCTAATGGTCCTTTGGCACCAGCTTTCGATAGGGTTATGCAAATCGG
AGATGCTTCAGCAGCTCAGTCACCATTGAGTTTTGGAGGTTTCGGTTCTATGATGAG
ACATTTGCCTAGACTCGCTAGGGGATTAGATCAGGCTCTTCAAGAGGATAGATTGGC
TAGGCCTGATCTTAACTGGCTTCACCCTTATCAACCAAGTCTTTCTGCTTCATGGTTG
TTTCAAAGAAGTATGTCTCTCGCAGTTGGTCAGGTGGCTTACCCTCCAGATTGCCCTC
ATGCACCAGCTTATTACGCAGCTGCAAAAGAGGCTAAGGCTGCAGCTGCAGCTGCA
GCTGTTGATAGAGCTGAAGGATTCGATGGTTTGGTGAGTACAGCAGGAGAGAGGGC
TCTTTCTTTGCAAGAAGCAGCTATGGAGGCAGTTGAAGCTGTGGCAGCTAGATTTGC
AGCTGGATCTGCAGATCCTGCTGATTATTTCCATGTTGAGCAGGAAGTGCCTGGAGC
TGGTTCAGATAGAAGGACTCCACAACTTGCTAGTGGAAAGGCACAGCCTGCTCCTCC
AAAATTGAAGAAAAAGCTCTTTGAGAGAGATTTCAGGACAGCTCCTGAATGGCAAA
GACTCCCATACACCCACGTTAATGAGATCCTTGGAACTAACTTTGGAGTTATGGGTG
TGTTGGGAGATAGAGTTTTAAAACCATTCCTTCAGGATACTATACAACTCGTGCCTC
TCTCATTAAGTATGACTGGTATGATGCTTTCAAATCCAGTTACCGTGAGTAGAGTTCT
TATGCAAGTGGGACCTAAGACATTGGTTTCTTGGTTTGCTCATTATTTCGCACTCGTT
GCTTACTCATTAGGTCACGTGTTGCTCAGTCCTCTTAGAGGAGTTGTGCCATCTTATT
CATTTCAGAGGATGTTGGATGCTCTCGAATACGGAAGTGGTTCTGATTATAGATACC
ATGCACCTGCTGGACCAGCAGCTGGTGCAGCTGTTTCAGCAGGAAGAGGTGCTCCTG
TGGCAGCTGCATTGAGTGCTGCAGCTAGGTCTATTGATGGAGGTGCAGCTACTGAGT
CTATGGATGGAGGAGATGGAGGAGATGCAGCTGGAGAGGCTGGAGCAGCTGGTAA
ATCTGAAGGAGGTTCAGTTAAAGGAAGAAAGGCTCCTAAACAACAGCAACCAGCAG
CTGAACCTATGCCAATCCCTGTTCCAGTGGCAGCTGCAACTGCTGCAGCTGCAGCTA
TGGCTGCTGCTACTATGGTTGTGGGATTGCCTGGTATCGGACCTGTTACTCTCGGAgg
cGATTATAAGGATGATGATGATAAGTGA |

What is claimed is:

1. An expression vector comprising a polynucleotide that comprises a nucleic acid sequence encoding a polypeptide having at least 95% identity to amino acids 57-876 of SEQ ID NO:1.

2. The expression vector of claim 1, wherein the polynucleotide comprises a nucleic acid sequence encoding a heterologous chloroplast transit peptide joined to the polypeptide.

3. The expression vector of claim 1, wherein the nucleic acid sequence encoding the polypeptide is operably linked to a heterologous promoter.

4. The expression vector of claim 1, wherein the polypeptide comprises the amino acids 57-876 of SEQ ID NO:1.

5. A host cell comprising the expression vector of claim 1.

6. The host cell of claim 5, wherein the host cell is a plant.

7. The host cell of claim 5, wherein the host cell is a eukaryotic alga.

8. A host cell comprising a polynucleotide comprising a nucleic acid sequence encoding a polypeptide having at least 95% identity to amino acids 57-876 of SEQ ID NO:1, wherein the host cell is from a photosynthetic organism and the nucleic acid sequence encoding the polypeptide is operably linked to a heterologous promoter.

9. The host cell of claim 8, wherein the nucleic acid sequence encoding the polypeptide is codon optimized for expression in the host cell.

10. The host cell of claim 8, wherein the polynucleotide comprises a nucleic acid sequence encoding a heterologous chloroplast transit peptide joined to the polypeptide.

11. The host cell of claim 8, wherein the polypeptide comprises amino acids 57-876 of SEQ ID NO:1.

12. The host cell of claim 8, wherein the photosynthetic organism is a plant.

13. The host cell of claim 8, wherein the photosynthetic organism is a eukaryotic alga.

14. A method of increasing the kinetics of non-photochemical quenching or increasing zeaxanthin production in a photosynthetic organism, the method comprising genetically modifying the photosynthetic organism to overexpress a polypeptide having at least 95% identity to amino acids 57-876 of SEQ ID NO:1 in the plant; thereby increasing the kinetics of non-photochemical quenching or increasing zeaxanthin production relative to a counterpart plant of the same strain that is not genetically modified to overexpress the polypeptide.

15. The method of claim 14, wherein the photosynthetic organism is a plant.

16. The method of claim 14, wherein the photosynthetic organism is a eukaryotic alga.

17. A photosynthetic organism obtained by the method of claim 14.

18. The photosynthetic organism of claim 17, wherein the photosynthetic organism is a plant.

19. The photosynthetic organism of claim 17, wherein the photosynthetic organism is a eukaryotic alga.

20. The host cell of claim 8, wherein the polypeptide has at least 99% identity to amino acids 57-876 of SEQ ID NO:1.

* * * * *

SEQUENCE LISTING

<160> NUMBER OF SEQ ID NOS: 20

<210> SEQ ID NO 1
<211> LENGTH: 876
<212> TYPE: PRT
<213> ORGANISM: Chlamydomonas reinhardtii

<400> SEQUENCE: 1

```
Met Gln Gln Arg Leu Leu Lys Pro His Thr Ala Gly Arg Pro Ser Gly
1               5                   10                  15

Ala Val Pro Ile Ala His Gly Leu Val Ser Gly Pro Arg Val Gln Pro
            20                  25                  30

Ala Ala Pro Ser Ala Arg Pro Ala Ser Gly Asn Val Thr Ser His Pro
        35                  40                  45

Val Gly Ala Arg Gly Pro Ala Cys Asp Gln Ala Ser Ser Ala Gly Lys
50                  55                  60

Arg Phe Asp Ser Leu Ala Ala Tyr Gly Leu Ala Arg Asp Val Leu Thr
65                  70                  75                  80

Lys Gln Ala Ser Asn Ile Glu Gly Asn Pro Ile Glu Phe Leu Asp Val
                85                  90                  95

Thr Glu Lys Phe Trp Arg Ala Leu Arg Asn Gln Lys His Glu Pro Glu
            100                 105                 110

Lys Lys Gly Pro Lys Val Val Thr Tyr Ala Asp Glu Leu Leu Phe Pro
        115                 120                 125

Asp Ser Ala Ser Ser Ser Ala Ser Thr Ser Ser Ser Pro His Pro
130                 135                 140

His Asp Tyr Asp Val Val Ile Cys Gly Gly Thr Leu Gly Leu Phe Leu
145                 150                 155                 160

Ala Thr Ala Leu Gln Leu Gln Gly Trp Arg Val Ala Ile Val Glu Lys
                165                 170                 175

Arg Leu Val Gln Gly Arg Asn Gln Glu Trp Asn Ile Ser Trp Gly Glu
            180                 185                 190

Leu Glu Val Leu Val Glu Leu Gly Leu Leu Ser Glu Glu Leu Lys
        195                 200                 205

Gly Cys Val Ile Ser Glu Phe Asn Pro Ile Arg Val Gly Phe Lys Gly
210                 215                 220

Gly Glu Asp Ile Trp Thr Gln Asp Val Leu Asn Leu Gly Val His Pro
225                 230                 235                 240

Arg Thr Leu Leu Asp Ser Leu Lys Arg Arg Phe His Ala Ala Gly Gly
                245                 250                 255

Ile Ile Phe Glu Asn Thr Ala Phe Lys His Ala Asp Val His Pro Asp
            260                 265                 270

Gly Ile Lys Leu Ser Leu Ala Pro Gly Ala Ala Ala Pro Val Ala
        275                 280                 285

Val Gly Asp Thr Asn Arg Pro Asn Gly Leu Thr Thr Gly Gly Ala Ala
    290                 295                 300

Pro Ala Pro Ser Gly Pro Val Ala Pro Arg Ser Met Thr Thr Arg Leu
305                 310                 315                 320

Leu Leu Asp Cys Met Gly His Tyr Ser Asp Ile Val Lys Gln Ile Arg
                325                 330                 335

Gly Arg Val Lys Pro Asp Gly Met Val Leu Val Val Gly Cys Ala
            340                 345                 350

Glu Gly Phe Pro Ala Glu Ala Asn Ile Ser Ala Asp Leu Leu Tyr Ser
        355                 360                 365

Leu Ser His Ala Arg Asp Asp Val Gln Leu Phe Trp Glu Ala Phe Pro
370                 375                 380

Ala Glu Gly Gly Gln Ala Arg Thr Thr Tyr Met Phe Ala Tyr Ser Asp
385                 390                 395                 400

Ala His Pro Asp Arg Pro Ser Phe Glu Ala Leu Leu Asp Thr Tyr Phe
```

```
                    405                 410                 415
Gln Met Leu Pro Glu Tyr Gln Gly Ile Pro Leu Asp Gln Leu Lys Phe
            420                 425                 430

Lys Arg Val Leu Phe Gly Gly Phe Pro Cys Tyr Ser Asn Gly Pro Leu
            435                 440                 445

Ala Pro Ala Phe Asp Arg Val Met Gln Ile Gly Asp Ala Ser Ala Ala
            450                 455                 460

Gln Ser Pro Leu Ser Phe Gly Phe Gly Ser Met Met Arg His Leu
465                 470                 475                 480

Pro Arg Leu Ala Arg Gly Leu Asp Gln Ala Leu Gln Glu Asp Arg Leu
                485                 490                 495

Ala Arg Pro Asp Leu Asn Trp Leu His Pro Tyr Gln Pro Ser Leu Ser
            500                 505                 510

Ala Ser Trp Leu Phe Gln Arg Ser Met Ser Leu Ala Val Gly Gln Val
            515                 520                 525

Ala Tyr Pro Pro Asp Cys Pro His Ala Pro Ala Tyr Tyr Ala Ala Ala
            530                 535                 540

Lys Glu Ala Lys Ala Ala Ala Ala Ala Val Asp Arg Ala Glu
545                 550                 555                 560

Gly Phe Asp Gly Leu Val Ser Thr Ala Gly Glu Arg Ala Leu Ser Leu
                565                 570                 575

Gln Glu Ala Ala Met Glu Ala Val Glu Ala Val Ala Arg Phe Ala
            580                 585                 590

Ala Gly Ser Ala Asp Pro Ala Asp Tyr Phe His Val Glu Gln Glu Val
            595                 600                 605

Pro Gly Ala Gly Ser Asp Arg Arg Thr Pro Gln Leu Ala Ser Gly Lys
            610                 615                 620

Ala Gln Pro Ala Pro Pro Lys Leu Lys Lys Leu Phe Glu Arg Asp
625                 630                 635                 640

Phe Arg Thr Ala Pro Glu Trp Gln Arg Leu Pro Tyr Thr His Val Asn
                645                 650                 655

Glu Ile Leu Gly Thr Asn Phe Gly Val Met Gly Val Leu Gly Asp Arg
                660                 665                 670

Val Leu Lys Pro Phe Leu Gln Asp Thr Ile Gln Leu Val Pro Leu Ser
            675                 680                 685

Leu Ser Met Thr Gly Met Met Leu Ser Asn Pro Val Thr Val Ser Arg
            690                 695                 700

Val Leu Met Gln Val Gly Pro Lys Thr Leu Val Ser Trp Phe Ala His
705                 710                 715                 720

Tyr Phe Ala Leu Val Ala Tyr Ser Leu Gly His Val Leu Leu Ser Pro
                725                 730                 735

Leu Arg Gly Val Val Pro Ser Tyr Ser Phe Gln Arg Met Leu Asp Ala
                740                 745                 750

Leu Glu Tyr Gly Ser Gly Ser Asp Tyr Arg Tyr His Ala Pro Ala Gly
            755                 760                 765

Pro Ala Ala Gly Ala Ala Val Ser Ala Gly Arg Gly Ala Pro Val Ala
            770                 775                 780

Ala Ala Leu Ser Ala Ala Arg Ser Ile Asp Gly Gly Ala Ala Thr
785                 790                 795                 800

Glu Ser Met Asp Gly Gly Asp Gly Gly Asp Ala Ala Gly Glu Ala Gly
                805                 810                 815

Ala Ala Gly Lys Ser Glu Gly Gly Ser Val Lys Gly Arg Lys Ala Pro
            820                 825                 830
```

Lys Gln Gln Gln Pro Ala Ala Glu Pro Met Pro Ile Pro Val Pro Val
    835                 840                 845

Ala Ala Ala Thr Ala Ala Ala Ala Ala Met Ala Ala Ala Thr Met Val
    850                 855                 860

Val Gly Leu Pro Gly Ile Gly Pro Val Thr Leu Gly
865                 870                 875

<210> SEQ ID NO 2
<211> LENGTH: 2631
<212> TYPE: DNA
<213> ORGANISM: Chlamydomonas reinhardtii

<400> SEQUENCE: 2

| | | | | | |
|---|---|---|---|---|---|
| atgcagcaac | gccttctgaa | gcctcatacg | gccggtcgcc | ctagcggcgc | tgtgcctatc | 60 |
| gctcatggtc | ttgtctcagg | gcctcgcgtg | cagccggctg | cgccctccgc | tcgcccagcg | 120 |
| tctggtaatg | tgacctcaca | tccagtgggc | gcgcgcgggc | cgcctgcga | ccaggccagc | 180 |
| agtgctggca | agcgtttcga | tagcctagca | gcctacgggc | tagctcggga | cgtgcttacg | 240 |
| aagcaggcct | cgaacattga | gggcaacccc | attgagttcc | ttgacgtgac | ggaaaagttc | 300 |
| tggagagcgc | ttcgtaacca | gaagcatgag | cccgagaaga | agggcccaa | ggtggtcaca | 360 |
| tacgcggacg | agctcctctt | cccagactcc | gcctcctcct | cctccgcctc | cacctcctcc | 420 |
| tcccccacc | cccacgacta | cgacgtggtc | atctgcggcg | gcacgttggg | gctgttcctg | 480 |
| gccaccgcgc | tgcagctgca | gggctggcgc | gtggccattg | tggagaagcg | cctggtgcag | 540 |
| ggccgcaacc | aggagtggaa | catcagctgg | ggcgagctgg | aggtgctggt | ggagctgggg | 600 |
| ctgttgagtg | aggaggagct | gaagggctgc | gtcatcagcg | agttcaaccc | catccgcgtg | 660 |
| gggttcaagg | gcggggagga | catttggact | caggatgtgc | tgaacctggg | tgtgcacccg | 720 |
| cgcacgctgc | tggactcgct | caagcggcgc | ttccacgccg | ccggtggcat | catctttgag | 780 |
| aacacggcct | tcaagcacgc | cgacgtgcac | ccggacggca | tcaagctgag | cctggcgccc | 840 |
| ggcggtgccg | ccgcgcccgt | ggcggttggc | gacaccaacc | gccccaacgg | cctaaccacc | 900 |
| ggcggcgccg | cgcccgcccc | ttcgggcccc | gtggcccctc | gctccatgac | cacacgcctg | 960 |
| ctgctggact | gcatgggtca | ctacagtgac | atcgtcaagc | agatccgcgg | ccgtgtgaag | 1020 |
| cctgacggca | tggtgctggt | ggtgggcggc | tgcgcggagg | gcttcccggc | ggaggccaac | 1080 |
| atcagcgccg | acctgctgta | cagcctgagc | cacgcccgcg | acgacgtgca | gctgttctgg | 1140 |
| gaggcgttcc | ccgcggaggg | cggccaggcg | cggaccacct | acatgttcgc | gtacagtgac | 1200 |
| gcgcacccgg | accggccctc | cttcgaggcg | ctgctagaca | cgtacttcca | gatgctgccc | 1260 |
| gagtaccagg | gcatcccgct | ggaccagctc | aagttcaagc | gtgtgctgtt | cggcggcttc | 1320 |
| ccctgctaca | gcaacggccc | gctggcgccc | gcctttgacc | gcgtgatgca | gatcggcgac | 1380 |
| gccagcgcgg | cccagtcgcc | tctgtcgttc | ggcggctttg | gctccatgat | gcgacacctg | 1440 |
| ccgcgcctgg | cgcgcggtct | ggaccaggcg | ctgcaggagg | accgcctggc | gcgacccgac | 1500 |
| ctcaactggc | tgcacccctà | ccagccgtcc | ctgtctgcct | cgtggctgtt | ccagcgctcc | 1560 |
| atgtcgttgg | cggttgggca | ggtggcctac | ccgcccgact | gccgcacgc | gcccgcctac | 1620 |
| tacgccgccg | ccaaggaggc | caaggccgcc | gcagccgccg | cggccgtgga | ccgcgccgag | 1680 |
| ggctttgacg | gcctggtctc | caccgccggc | gagcgcgcgc | tgtcgcttca | ggaggcggcg | 1740 |
| atggaggcgg | tggaggcggt | ggcggcccgc | ttcgccgccg | gcagtgccga | ccccgccgac | 1800 |
| tacttccatg | tggagcagga | ggtgccggga | gcgggcagcg | accgccgcac | gccgcagctg | 1860 |

```
gccagcggca aggcgcagcc cgcgccgccc aagctgaaga agaagctgtt tgagcgcgac      1920
ttccgtacgg cgccggagtg gcagcgcctg ccgtacacgc acgtgaacga gatcctgggg      1980
accaacttcg gcgtgatggg ggtgctgggc gaccgcgtgc tcaaaccctt cctgcaggac      2040
acgatccagc tggtgccgct gtcgctgtcc atgaccggca tgatgctgtc caaccccgtc      2100
accgtcagcc gcgtgctcat gcaggtcggc cccaagacgc tggtgtcctg gttcgcgcac      2160
tactttgcgc tggtggccta cagcctgggg cacgtgctgc tcagccctct gcgcggcgtg      2220
gtgccctcct actccttcca gcgcatgctg gacgccctag agtacggcag cggctctgac      2280
taccgctacc acgcccccgc cggcccggcg gcgggcgccg ccgtctcggc gggccgcggc      2340
gcgcccgtgg cggcggcgct gagcgccgct gcacggtcca ttgacggcgg cgcggcaacg      2400
gagagcatgg atggcggcga tggtgggggat gcggcgggcg aggccggcgc ggccgggaag      2460
```

-continued

```
atccgcgtgg ggttcaaggg cggggaggtg agcgagcgag ggcttgttac aaggataggg    1380
gggagagaga ggaaaggggg gagaaaggtg agaggggaa agtggggagg gggttgggag     1440
aggtaagcgg cgtgtgagtc acgacaggtg gggtcggcgc agctatgggg gatggacgga    1500
gcgcggagca gccgtgtggc gaggggccgg agaggagacc gggttacagc gcggaggcca    1560
taacatggta acatggcttg gcggaagcag agtatggcag aagcggttcc tggcggcttc    1620
caagaaggag acgaaatcta gaaatcagtc tcgcagcatg caggagtggc ttcctaacgc    1680
cgcatctgta tccttcccgc tccctctcct ctcctctcct ctcctcagga catttggact    1740
caggatgtgc tgaacctggg tgtgcacccg cgcacgctgc tggactcgct caagcggcgc    1800
ttccacgccg ccggtggcat catctttgag aacacggcct tcaagcacgc cgacgtgcac    1860
ccggtgagga caaacactaa atgggcttct tctcttggga gggagagagg gggcggagga    1920
ggcaatagga aagggcttgg aaggtctgtg aggagggcgc ggatgcaaac aaacacgtac    1980
cgtatgagca tcagaaccca ttttgaagga aagttgaaaa ctcttcccac ctggaaatga    2040
tctgttcgtg caggacggca tcaagctgag cctggcgccc ggcggtgccg ccgcgcccgt    2100
ggcggttggc gacaccaacc gccccaacgg cctaaccacc ggcggcgccg cgcccgcccc    2160
ttcgggcccc gtggcccctc gctccatgac acacgcctg ctgctggact gcatgggtca     2220
ctacaggtgg ggggaaggga ggccgtggag ggatgaaggg aggccgtgga gggaggcagg    2280
gaaggagggg cactaaaacg cttacacagc agggttgtgg tgttggcggg ttccgagtgt    2340
cccaacgcac cgcgttgcag actgcgatgg cgtagaatgg ttgaaggcgc gcaggaacgc    2400
tatcaggcct gttgcggcca atgcacccac aacacttgct ccgctgtccc tcctctcccc    2460
cccacggttt agtttgggct ggttttaaca accctcccac cgcacacaca cacgttacac    2520
acccgcgccc gtagtgacat cgtcaagcag atccgcggcc gtgtgaagcc tgacggcatg    2580
gtgctggtgg tgggcggctg cgcggagggc ttcccggcgg aggccaacat cagcgccgac    2640
ctgctgtaca ggtgtgtgtg tgtggggggg gggggggggg gctgtgtgtg tatgtggggg    2700
gggggggtgc ggatggaggg agggcgtggg ggggtgggag gggggggcttg gagagggga    2760 ggcgacttgt agaaactgaa gttgtaggcg tgagaggcgt gagtcgagca cgaggcgacg    2820
aaagtaacgc cggttggtct ggagccgact cagatcgggc ttgagcgctt aggccttctc    2880
ctccgtgctc aaaatcaaca gtaagtatta tcacaatgca atcatcatcg caacgcaaca    2940
taacctgctt ctccattatg cctctgccgc cttcacggtc gcagcctgag ccacgcccgc    3000
gacgacgtgc agctgttctg ggaggcgttc cccgcggagg gcggccaggc gcggaccacc    3060
tacatgttcg cgtacaggtg agagagtgag agaggggca gagaggaggg gaggaggcag     3120
gggtggggag gggaggaggc aggggcgggg agggccgtag gtccgcaccc acacctgcgt    3180
ggcagtgcac tgaacgcgca gcgagcaggc ccgggcggcg gaaggcttgg tccaggggca    3240
gggacagtga caggggcagg ggccttgcga gcaacacaca cgcatgcaca catgcgcaca    3300
cgcaccgatt cttgggtttc tgaaacacac acacacacct ttcgtttcgt tttttaacac    3360
acctccttcc ctcccctcgc agtgacgcgc acccggaccg gccctccttc gaggcgctgc    3420
tagacacgta cttccagatg ctgcccgagt accaggtggg tggctggggg gggagagat    3480 cgtgtatgcg gaaggaggac gggggggga gcgggttgga tgtgactgat gttgatgacg     3540
agtgtttgat gaaacacac gcgatgcgcg gggacacat cttgtatgt aacactaccg       3600 tgtgtgtaac aaacgcgaac cctcgtgtcg aacacccaca gggcatcccg ctggaccagc    3660
tcaagttcaa gcgtgtgctg ttcggcggct tccctgcta cagcaacggc ccgctggcgc     3720
```

```
ccgcctttga ccgcgtgatg caggtgggcg gtgggaatag aggggatgtg ggggaggcgg    3780
gtgcgcgtga ttgtgggttg tggggaattg ggggggtgga ggggcggggt atgcgtgtag    3840
cgtggcatgt ggggtggcgt ggcaggagtt gtagcgctgg ggctggggct tggaaataca    3900
tgcccgagtc caacataatc tgaggtcgca gttctcaagg agggaggggg ggcgcggcgg    3960
gccacgctct gctatcaagc ccaccaatcc tcaatgtaca agctttgaca ccaccaaaac    4020
aacccaggct aagcattccc aaaaataatc gattatcccg gtacccacaa cccaaaacgc    4080
agatcggcga cgccagcgcg gcccagtcgc ctctgtcgtt cggcggcttt ggctccatga    4140
tgcgacacct gccgcgcctg gcgcgcggtc tggaccaggc gctgcaggag gaccgcctgg    4200
cgcgacccga cctcaactgg ctgcacccct accaggtgag ggacgaattg aggggggggtt    4260 tgaggagttg tggggaccgg ttgcattcat gattggcaac gggaatgggg gattgggggg    4320
gggggtagag ttggtgaggg aagttgggtt ggaagcggga gcaattcgat gggggggtt    4380 aactcgtggg gttaacttgg ttgggggaga tttgggagtg gggacgggga aggaacgaag    4440
cgtgggcacg tacgcacacc atctgtctgg cacccgacaa cgccctgcaa ttccgccact    4500
caactccagc acaccacat tccaataaag atcctcacac gcgcctcctc ctccctctcc    4560
tgtcgccgcc gcagccgtcc ctgtctgcct cgtggctgtt ccagcgctcc atgtcgttgg    4620
cggttgggca ggtggcctac ccgcccgact gcccgcacgc gcccgcctac tacgccgccg    4680
ccaaggtgag gaggagggag agggcgaggg gcaggggggcg agagggtgag gggcagggggg   4740 ggagaggagg ccgtgggaaa ggagagggct tgggaaggga gagggcatgg gaaggatgag    4800
tgtcgtgggg gcgcgtgggc gtgtgcgttg aggctgatgc atgggtggta gcagtgtggc    4860
gtgcgggctt ggaattcgca caggtaccgc cactagcgcg cccacactgc cgccgccgcc    4920
tccaccgcct ccatcccgcc tccgccccac aacccaccac ctccccgcgc cccatggccc    4980
gcttgcttat gatctgccac ctagcccag gcaagccgcg caaacgtgtg tgaaaacggc    5040
gttgacctaa tacgtgcgat gtgctgtagc aaccacgctg tcacggcgct tcccactgca    5100
caccaaacat gcacgccctc ccttccaaaa ccgccgcaat cccttttcctc aacctcacca    5160 cccaccctcc tcgctcccat ccctcctcgc tcccaccaca ggaggccaag gccgccgcag    5220
ccgccgcggc cgtggaccgc gccgagggct ttgacggcct ggtctccacc gccggcgagc    5280
gcgcgctgtc gcttcaggag gcggcgatgg aaggcggtgga ggcggtggcg gcccgcttcg    5340
ccgccggcag tgccgacccc gccgactact tccatgtgga gcaggaggtg ccgggagcgg    5400
gcagcgaccc ccgcacgccg cagctggcca gcggcaaggc gcaggtgggg cgtgtgtgtg    5460
tgtgtggggg gggggggtg gcgggggagg gggccggggg agcggggtgc aaagatggtt    5520
ggagaagctg tacacgaaag ggggggctgg ggcagcggcg gcggcaagcc ccgagatggg    5580
agaaattgga ggggccgcgg cgtagagacg aaggcaaggt ggtgggcggt ccacattggc    5640
gatggcgtgt gtgtaccttg tgccttccta acgatccgca cacgcacaca cacccaatac    5700
acacacgagt gcagcccgcg ccgcccaagc tgaagaagaa gctgtttgag cgcgacttcc    5760
gtacggcgcc ggagtggcag cgcctgccgt acacgcacgt gaacgagatc ctggggacca    5820
acttcggcgt gatgggggtg ctgggcgacc gcgtgctcaa acccttcctg caggtgcgtg    5880
tgggcgtgtg tgtgtgtgtg tgtgtgggtt ggggtatggg ggaagtatgt gcatgtgctt    5940
gtgagggttc tgggttttcc ggttgggagg gaaaggggac aggaagggga tcaaccgcaa    6000 ccctctcac tcgcacacaa atacacgcac acacacattc ttgttcactc actcccactc    6060
```

| | |
|---|---|
| cttcactcac tctcacacac tctctctctc tctcgctcac tccacaggac acgatccagc | 6120 |
| tggtgccgct gtcgctgtcc atgaccggca tgatgctgtc caaccccgtc accgtcagcc | 6180 |
| gcgtgctcat gcaggtgtgt gtgcgcgggt gtatgtgtgt gtgtgtaagt gtatgttggg | 6240 |
| tcggtgggtg ggtgggtggg tgggtgggggg aaagtagaga ggagcgagga gggaggcagg | 6300 |
| cagggagggg gcgcagcatg gagtgggggga gtaagggagg gatggaaaca caagcgaaga | 6360 |
| gtggcccggg cctgtgtctt gtgcccaacc tcttccatcc gatgatgcct cccatgctca | 6420 |
| tccatttccc aattcagcac ttaccccaac ccaccaacca acatcatcgc gcacctgctt | 6480 |
| acacacaggt cggccccaag acgctggtgt cctggttcgc gcactacttt gcgctggtgg | 6540 |
| cctacagcct ggggcacgtg ctgctcagcc ctctgcgcgg cgtggtgccc tcctactcct | 6600 |
| tccagcgcat gctggacgcc ctagagtacg cagcggctc tgactaccgc taccacgccc | 6660 |
| ccgccggccc ggcggcgggc gccgccgtct cggcgggcc cggcgcgccc gtggcggcgg | 6720 |
| cgctgagcgc cgctgcacgg tccattgacg gcggcgcggc aacgagagc atggatggcg | 6780 |
| gcgatggtgg ggatgcggcg ggcgaggccg gcgcggccgg gaagagcgag ggcgggtcgg | 6840 |
| tgaaggggcg caaggcgccc aagcagcagc agccggcggc ggagccgatg cccattccgg | 6900 |
| tgccggtggc ggcggcgacg gccgcggcgg cggctatggc ggcggcgacc atggtggttg | 6960 |
| gcctcccagg catcggcccc gtcaccctcg ggtga | 6995 |

<210> SEQ ID NO 4
<211> LENGTH: 7025
<212> TYPE: DNA
<213> ORGANISM: Artificial Sequence
<220> FEATURE:
<223> OTHER INFORMATION: Synthetic construct

<400> SEQUENCE: 4

| | |
|---|---|
| atgcagcaac gccttctgaa gcctcatacg gccggtcgcc ctagcggcgc tgtgcctatc | 60 |
| gctcatggtc ttgtctcagg gcctcgcgtg cagccggctg cgcccctccgc tcgcccagcg | 120 |
| tctggtaatg tgacctcaca tccagtgggc gcgcgcgggc ccgcctgcga ccaggccagc | 180 |
| agtgctggca agcgtttcga tagcctagca gcctacgggc tagctcggga cgtgcttacg | 240 |
| aagcaggcct cgaacattga gggcaacccc attgagttcc ttgacgtgac ggaaaagttc | 300 |
| tggagagcgc ttcgtaacca gaagcatgag cccgagaaga agggcccaa ggtgagagat | 360 |
| gttgcgccag tcttggagcc gaccgtgctg ctgacaggcc agtgtttccg gccctccgcc | 420 |
| gcgccaaatg gctttaaact tgcacatcgt agctgctttt acgccgggcg tttcggcggc | 480 |
| tgtgttgacg tcacgagcgc gcgcgcgcgc tctcggcctc acggctctct aactgctccg | 540 |
| accccctcttt accgttggcc ctgcggctct cgcgacctgc tggcacgcca gctgtcagct | 600 |
| gccagctgtc ccctgtccca atcccttgc atccttttg ctgaacccct ccttccttc | 660 |
| ccctctcctt cccgctcctc cctccctcc cgctcctccc tcccctcccc tctcctctcc | 720 |
| tgcctctccc tcaggtggtc acatacgcgg acagctcct cttcccagac tccgcctcct | 780 |
| cctcctccgc ctccacctcc tcctcccccc accccacga ctacgacgtg gtcatctgcg | 840 |
| gcggcacgtt ggggctgttc ctggccaccg cgctgcagct gcagggctgg cgcgtggcca | 900 |
| ttgtggagaa cgcctggtg caggtgaggc ggcggggtgg gcaagagcgg gggcccaagg | 960 |
| agcgggcggg ggcgtcgggg tgcgcgtgac gtgccacgga cccctaaag gcacgtcttc | 1020 |
| gtagcagcag ctagcagtag cagtaaacac ctgacggtaa atcgcctgcg gcctgaagtg | 1080 |
| ccggccattc gctcttgaaa ctagcctgcg ggatgctaca gctgccctgt atcagtcctc | 1140 |

-continued

```
catgcggctg ctgctgctgc tgctgctgct cctgtaactg ttgctgtcgc tgctgcttct      1200
gtccaacagg gccgcaacca ggagtggaac atcagctggg gcgagctgga ggtgctggtg      1260
gagctggggc tgttgagtga ggaggagctg aagggctgcg tcatcagcga gttcaacccc      1320
atccgcgtgg ggttcaaggg cggggaggtg agcgagcgag ggcttgttac aaggataggg      1380
gggagagaga ggaaagggg gagaaggtg agagggggaa agtggggagg gggttgggag        1440
aggtaagcgg cgtgtgagtc acgacaggtg gggtcggcgc agctatgggg gatggacgga      1500
gcgcggagca gccgtgtggc gaggggccgg agaggagacc gggttacagc gcggaggcca      1560
taacatggta acatggcttg gcggaagcag agtatggcag aagcggttcc tggcggcttc      1620
caagaaggag acgaaatcta gaaatcagtc tcgcagcatg caggagtggc ttcctaacgc      1680
cgcatctgta tccttcccgc tccctctcct ctcctctcct ctcctcagga catttggact      1740
caggatgtgc tgaacctggg tgtgcacccg cgcacgctgc tggactcgct caagcggcgc      1800
ttccacgccg ccggtggcat catctttgag aacacggcct tcaagcacgc cgacgtgcac      1860
ccggtgagga caaacactaa atgggcttct tctcttggga gggagagagg gggcggagga      1920
ggcaatagga aagggcttgg aaggtctgtg aggagggcgc ggatgcaaac aaacacgtac      1980
cgtatgagca tcagaaccca tttgaagga aagttgaaaa ctcttcccac ctggaaatga      2040
tctgttcgtg caggacggca tcaagctgag cctggcgccc ggcggtgccg ccgcgcccgt      2100
ggcggttggc gacaccaacc gccccaacgg cctaaccacc ggcggcgccg cgcccgcccc      2160
ttcgggcccc gtggcccctc gctccatgac cacacgcctg ctgctggact gcatgggtca      2220
ctacaggtgg ggggaaggga ggccgtggag ggatgaaggg aggccgtgga gggaggcagg      2280
gaaggagggg cactaaaacg cttacacagc agggttgtgg tgttggcggg ttccgagtgt      2340
cccaacgcac cgcgttgcag actgcgatgg cgtagaatgg ttgaaggcgc gcaggaacgc      2400
tatcaggcct gttgcggcca atgcacccac aacacttgct ccgctgtccc tcctctcccc      2460
cccacggttt agtttgggct ggttttaaca accctcccac cgcacacaca cacgttacac      2520
acccgcgccc gtagtgacat cgtcaagcag atccgcggcc gtgtgaagcc tgacggcatg      2580
gtgctggtgg tgggcggctg cgcggagggc ttcccggcgg aggccaacat cagcgccgac      2640
ctgctgtaca ggtgtgtgtg tgtggggggg ggggggggg gctgtgtgtg tatgtggggg       2700
gggggggtgc ggatggaggg agggcgtggg ggggtggag ggggggcttg gagagggga       2760 ggcgacttgt agaaactgaa gttgtaggcg tgagaggcgt gagtcgagca cgaggcgacg      2820
aaagtaacgc cggttggtct ggagccgact cagatcgggc ttgagcgctt aggccttctc      2880
ctccgtgctc aaaatcaaca gtaagtatta tcacaatgca atcatcatcg caacgcaaca      2940
taacctgctt ctccattatg cctctgccgc cttcacggtc gcagcctgag ccacgcccgc      3000
gacgacgtgc agctgttctg ggaggcgttc cccgcggagg gcggccaggc gcggaccacc      3060
tacatgttcg cgtacaggtg agagagtgag agaggggca gagaggaggg gagggggcag       3120
gggtggggag gggaggaggc aggggcgggg agggccgtag gtccgcaccc acacctgcgt      3180
ggcagtgcac tgaacgcgca gcgagcaggc ccgggcggcg gaaggcttgg tccaggggca      3240
gggacagtga caggggcagg ggccttgcga gcaacacaca cgcatgcaca catgcgcaca      3300
cgcaccgatt cttgggtttc tgaaacacac acacacacct ttcgtttcgt ttttaacac       3360 acctccttcc ctcccctcgc agtgacgcgc accggaccg gccctccttc gaggcgctgc      3420
tagacacgta cttccagatg ctgcccgagt accaggtggg tggctggggg ggggagagat      3480
```

```
cgtgtatgcg gaaggaggac gggggggggga gcgggttgga tgtgactgat gttgatgacg    3540
agtgtttgat gaaaacacac gcgatgcgcg ggggacacat ctttgtatgt aacactaccg    3600
tgtgtgtaac aaacgcgaac cctcgtgtcg aacacccaca gggcatcccg ctggaccagc    3660
tcaagttcaa gcgtgtgctg ttcggcggct tcccctgcta cagcaacggc ccgctggcgc    3720
ccgcctttga ccgcgtgatg caggtgggcg gtgggaatag aggggatgtg ggggaggcgg    3780
gtgcgcgtga ttgtgggttg tggggaattg ggggggtgga ggggcggggt atgcgtgtag    3840
cgtggcatgt ggggtggcgt ggcaggagtt gtagcgctgg ggctgggggct tggaaataca    3900 tgcccgagtc caacataatc tgaggtcgca gttctcaagg agggaggggg ggcgcggcgg    3960
gccacgctct gctatcaagc ccaccaatcc tcaatgtaca agctttgaca ccaccaaaac    4020
aacccaggct aagcattccc aaaaataatc gattatcccg gtacccacaa cccaaaacgc    4080
agatcggcga cgccagcgcg gcccagtcgc ctctgtcgtt cggcggcttt ggctccatga    4140
tgcgacacct gccgcgcctg gcgcgcggtc tggaccaggc gctgcaggag gaccgcctgg    4200
cgcgacccga cctcaactgg ctgcacccct accaggtgag ggacgaattg agggggggtt    4260
tgaggagttg tggggaccgg ttgcattcat gattggcaac gggaatgggg gattgggggg    4320
gggggtagag ttggtgaggg aagttgggtt ggaagcggga gcaattcgat ggggggggtt    4380
aactcgtggg gttaacttgg ttgggggaga tttgggagtg gggacgggga aggaacgaag    4440
cgtgggcacg tacgcacacc atctgtctgg cacccgacaa cgccctgcaa ttccgccact    4500
caactccagc acacccacat tccaataaag atcctcacac gcgcctcctc ctccctctcc    4560
tgtcgccgcc gcagccgtcc ctgtctgcct cgtggctgtt ccagcgctcc atgtcgttgg    4620
cggttgggca ggtggcctac ccgcccgact gcccgcacgc gcccgcctac tacgccgccg    4680
ccaaggtgag gaggagggag agggcgaggg gcaggggggcg agagggtgag gggcaggggg    4740
ggagaggagg ccgtgggaaa ggagagggct tgggaaggga gagggcatgg gaaggatgag    4800
tgtcgtgggg gcgcgtgggc gtgtgcgttg aggctgatgc atgggtggta gcagtgtggc    4860
gtgcgggctt ggaattcgca caggtaccgc cactagcgcg cccacactgc cgccgccgcc    4920
tccaccgcct ccatcccgcc tccgccccac aacccaccac ctccccgcgc ccatggcccc    4980
gcttgcttat gatctgccac ctagccccag gcaagccgcg caaacgtgtg tgaaaacggc    5040
gttgacctaa tacgtgcgat gtgctgtagc aaccacgctg tcacggcgct tcccactgca    5100
caccaaacat gcacgccctc ccttccaaaa ccgccgcaat ccctttcctc aacctcacca    5160
cccaccctcc tcgctcccat ccctcctcgc tcccaccaca ggaggccaag gccgccgcag    5220
ccgccgcggc cgtggaccgc gccgagggct ttgacggcct ggtctccacc gccggcgagc    5280
gcgcgctgtc gcttcaggag gcggcgatgg aggcggtgga ggcggtggcg gcccgcttcg    5340
ccgccggcag tgccgacccc gccgactact tccatgtgga gcaggaggtg ccgggagcgg    5400
gcagcgaccg ccgcacgccg cagctggcca gcggcaaggc gcaggtgggg cgtgtgtgtg    5460
tgtgtggggg ggggggggtg gcgggggagg gggccggggg agcggggtgc aaagatggtt    5520
ggagaagctg tacacgaaag gggggggctgg ggcagcggcg gcggcaagcc ccgagatggg    5580
agaaattgga ggggccgcgg cgtagagacg aaggcaaggt ggtgggcggt ccacattggc    5640
gatggcgtgt gtgtaccttg tgccttccta acgatccgca cacgcacaca cacccaatac    5700
acacacgagt gcagcccgcg ccgcccaagc tgaagaagaa gctgtttgag cgcgacttcc    5760
gtacggcgcc ggagtggcag cgcctgccgt acacgcacgt gaacgagatc ctggggacca    5820
acttcggcgt gatgggggtg ctgggcgacc gcgtgctcaa acccttcctg caggtgcgtg    5880
```

```
tgggcgtgtg tgtgtgtgtg tgtgtgggtt ggggtatggg ggaagtatgt gcatgtgctt    5940
gtgagggttc tgggttttcc ggttgggagg gaaagggggac aggaaaggga tcaaccgcaa    6000
cccctctcac tcgcacacaa atacacgcac acacacattc ttgttcactc actcccactc    6060
cttcactcac tctcacacac tctctctctc tctcgctcac tccacaggac acgatccagc    6120
tggtgccgct gtcgctgtcc atgaccggca tgatgctgtc caaccccgtc accgtcagcc    6180
gcgtgctcat gcaggtgtgt gtgcgcgggt gtatgtgtgt gtgtgtaagt gtatgttggg    6240
tcggtgggtg ggtgggtggg tgggtggggg aaagtagaga ggagcgagga gggaggcagg    6300
cagggagggg gcgcagcatg gagtgggggga gtaagggagg gatggaaaca caagcgaaga    6360
gtggcccggg cctgtgtctt gtgcccaacc tcttccatcc gatgatgcct cccatgctca    6420
tccatttccc aattcagcac ttaccccaac ccaccaacca acatcatcgc gcacctgctt    6480
acacacaggt cggccccaag acgctggtgt cctggttcgc gcactacttt gcgctggtgg    6540
cctacagcct ggggcacgtg ctgctcagcc ctctgcgcgg cgtggtgccc tcctactcct    6600
tccagcgcat gctggacgcc ctagagtacg gcagcggctc tgactaccgc taccacgccc    6660
ccgccggccc ggcggcgggc gccgccgtct cggcgggccg cggcgcgccc gtggcggcg    6720 cgctgagcgc cgctgcacgg tccattgacg gcggcgcggc aacggagagc atggatggcg    6780
gcgatggtgg ggatgcggcg ggcgaggccg gcgcggccgg gaagagcgag ggcgggtcgg    6840
tgaaggggcg caaggcgccc aagcagcagc agccggcggc ggagccgatg cccattccgg    6900
tgccggtggc ggcggcgacg gccgcggcgg cggctatggc ggcggcgacc atggtggttg    6960
gcctcccagg catcggcccc gtcaccctcg gcggcgacta caaggacgat gacgacaagt    7020
gatga                                                              7025
```

<210> SEQ ID NO 5
<211> LENGTH: 2631
<212> TYPE: DNA
<213> ORGANISM: Artificial Sequence
<220> FEATURE:
<223> OTHER INFORMATION: Synthetic construct

<400> SEQUENCE: 5

```
atgcagcaaa gattactcaa gcctcacaca gcaggtagac caagtggagc agttcctatc     60
gcacacggac tcgttagtgg accaagagtt caacctgctg caccaagtgc aagacctgct    120
tctggaaatg ttacttcaca tcctgtggga gcaaggggggc ccgcatgcga tcaagcatct    180
tcagctggaa agagatttga ttcattggct gcttatggac tcgctaggga tgttttaacc    240
aagcaggctt ctaatatcga gggtaaccca atagaatttt tggatgtgac tgagaagttc    300
tggagagctc tcaggaacca gaaacacgag cctgaaaaga aaggaccaaa ggttgtgact    360
tatgctgatg aacttttgtt tcctgattct gcaagttctt caagtgcttc aacctcttca    420
agtcctcatc cacacgatta cgatgttgtg atttgtggag gtactttagg tcttttcttg    480
gcaacagctc tccagttaca aggatggaga gttgctatag tggagaaaag acttgttcag    540
ggtaggaatc aagagtggaa tatttcttgg ggagagcttg aagttttggt ggagctcggt    600
ctcttatcag aagaggaatt gaaaggatgc gttatttctg agtttaatcc aatcagagtg    660
ggtttcaagg gaggtgaaga tatatggact caagatgttc ttaacttggg agtgcatcct    720
aggacacttt tggattcact taagagaagg ttccacgctg caggaggtat tatcttcgaa    780
aacaccgcat tcaaacatgc tgatgttcac ccagatggaa tcaagctctc tttagctcct    840
```

| | |
|---|---|
| ggaggtgctg cagctccagt tgctgtggga gatacaaata gacctaacgg tcttactaca | 900 |
| ggaggtgcag ctcctgcacc aagtggtcct gttgctccaa gatcaatgac cactaggctc | 960 |
| ttacttgatt gtatgggaca ttactctgat atagttaagc aaataagagg aagggttaaa | 1020 |
| ccagatggta tggtgttggt tgtgggaggt tgcgctgagg gttttcctgc agaagctaac | 1080 |
| atctctgctg atttgctcta ctctctctca catgctagag atgatgttca attattttgg | 1140 |
| gaggcattcc cagctgaagg tggtcaggct agaacaacct atatgttcgc atactctgat | 1200 |
| gctcaccctg ataggccatc atttgaggct ttacttgata cttacttcca gatgcttcct | 1260 |
| gaataccaag gtattcctct tgatcagctt aagtttaaga gagttctttt tggaggtttc | 1320 |
| ccttgttact ctaatggtcc tttggcacca gctttcgata gggttatgca aatcggagat | 1380 |
| gcttcagcag ctcagtcacc attgagtttt ggaggtttcg ttctatgat gagacatttg | 1440 |
| cctagactcg ctaggggatt agatcaggct cttcaagagg atagattggc taggcctgat | 1500 |
| cttaactggc ttcaccctta tcaaccaagt ctttctgctt catggttgtt tcaaagaagt | 1560 |
| atgtctctcg cagttggtca ggtggcttac cctccagatt gccctcatgc accagcttat | 1620 |
| tacgcagctg caaaagaggc taaggctgca gctgcagctg cagctgttga tagagctgaa | 1680 |
| ggattcgatg gtttggtgag tacagcagga gagagggctc tttctttgca agaagcagct | 1740 |
| atggaggcag ttgaagctgt ggcagctaga tttgcagctg gatctgcaga tcctgctgat | 1800 |
| tatttccatg ttgagcagga agtgcctgga gctggttcag atagaaggac tccacaactt | 1860 |
| gctagtggaa aggcacagcc tgctcctcca aaattgaaga aaaagctctt tgagagagat | 1920 |
| ttcaggacag ctcctgaatg gcaaagactc ccatacaccc acgttaatga gatccttgga | 1980 |
| actaactttg gagttatggg tgtgttggga gatagagttt taaaaccatt ccttcaggat | 2040 |
| actatacaac tcgtgcctct ctcattaagt atgactggta tgatgctttc aaatccagtt | 2100 |
| accgtgagta gagttcttat gcaagtggga cctaagacat tggtttcttg gtttgctcat | 2160 |
| tatttcgcac tcgttgctta ctcattaggt cacgtgttgc tcagtcctct tagaggagtt | 2220 |
| gtgccatctt attcatttca gaggatgttg gatgctctcg aatacggaag tggttctgat | 2280 |
| tatagatacc atgcacctgc tggaccagca gctggtgcag ctgtttcagc aggaagaggt | 2340 |
| gctcctgtgg cagctgcatt gagtgctgca gctaggtcta ttgatggagg tgcagctact | 2400 |
| gagtctatgg atgaggagga tggaggagat gcagctggag aggctggagc agctggtaaa | 2460 |
| tctgaaggag gttcagttaa aggaagaaag gctcctaaac aacagcaacc agcagctgaa | 2520 |
| cctatgccaa tccctgttcc agtggcagct gcaactgctg cagctgcagc tatggctgct | 2580 |
| gctactatgg ttgtgggatt gcctggtatc ggacctgtta ctctcggatg a | 2631 |

<210> SEQ ID NO 6
<211> LENGTH: 2658
<212> TYPE: DNA
<213> ORGANISM: Artificial Sequence
<220> FEATURE:
<223> OTHER INFORMATION: Synthetic construct

<400> SEQUENCE: 6

| | |
|---|---|
| atgcagcaaa gattactcaa gcctcacaca gcaggtagac caagtggagc agttcctatc | 60 |
| gcacacggac tcgttagtgg accaagagtt caacctgctg caccaagtgc aagacctgct | 120 |
| tctggaaatg ttacttcaca tcctgtggga gcaggggggc ccgcatgcga tcaagcatct | 180 |
| tcagctggaa agagatttga ttcattggct gcttatggac tcgctaggga tgttttaacc | 240 |
| aagcaggctt ctaatatcga gggtaaccca atagaatttt tggatgtgac tgagaagttc | 300 |

```
tggagagctc tcaggaacca gaaacacgag cctgaaaaga aaggaccaaa ggttgtgact    360
tatgctgatg aacttttgtt tcctgattct gcaagttctt caagtgcttc aacctcttca    420
agtcctcatc cacacgatta cgatgttgtg atttgtggag gtactttagg tcttttcttg    480
gcaacagctc tccagttaca aggatggaga gttgctatag tggagaaaag acttgttcag    540
ggtaggaatc aagagtggaa tatttcttgg ggagagcttg aagttttggt ggagctcggt    600
ctcttatcag aagaggaatt gaaggatgc gttatttctg agtttaatcc aatcagagtg     660
ggtttcaagg gaggtgaaga tatatggact caagatgttc ttaacttggg agtgcatcct    720
aggacacttt tggattcact taagagaagg ttccacgctg caggaggtat tatcttcgaa    780
aacaccgcat tcaaacatgc tgatgttcac ccagatggaa tcaagctctc tttagctcct    840
ggaggtgctg cagctccagt tgctgtggga gatacaaata gacctaacgg tcttactaca    900
ggaggtgcag ctcctgcacc aagtggtcct gttgctccaa gatcaatgac cactaggctc    960
ttacttgatt gtatgggaca ttactctgat atagttaagc aaataagagg aagggttaaa   1020
ccagatggta tggtgttggt tgtgggaggt tgcgctgagg gttttcctgc agaagctaac   1080
atctctgctg atttgctcta ctctctctca catgctagag atgatgttca attattttgg   1140
gaggcattcc cagctgaagg tggtcaggct agaacaacct atatgttcgc atactctgat   1200
gctcaccctg ataggccatc atttgaggct ttacttgata cttacttcca gatgcttcct   1260
gaataccaag gtattcctct tgatcagctt aagtttaaga gagttctttt tggaggtttc   1320
ccttgttact ctaatggtcc tttggcacca gctttcgata gggttatgca aatcggagat   1380
gcttcagcag ctcagtcacc attgagtttt ggaggtttcg gttctatgat gagacatttg   1440
cctagactcg ctaggggatt agatcaggct cttcaagagg atagattggc taggcctgat   1500
cttaactggc ttcacccctta tcaaccaagt cttttctgctt catggttgtt tcaaagaagt   1560
atgtctctcg cagttggtca ggtggcttac cctccagatt gccctcatgc accagcttat   1620
tacgcagctg caaaagaggc taaggctgca gctgcagctg cagctgttga tagagctgaa   1680
ggattcgatg gtttggtgag tacagcagga gagagggctc tttctttgca agaagcagct   1740
atggaggcag ttgaagctgt ggcagctaga tttgcagctg gatctgcaga tcctgctgat   1800
tatttccatg ttgagcagga agtgcctgga gctggttcag atagaaggac tccacaactt   1860
gctagtggaa aggcacagcc tgctcctcca aaattgaaga aaaagctctt tgagagagat   1920
ttcaggacag ctcctgaatg gcaaagactc ccatacaccc acgttaatga gatccttgga   1980
actaactttg gagttatggg tgtgttggga gatagagttt aaaaccatt ccttcaggat     2040
actatacaac tcgtgcctct ctcattaagt atgactggta tgatgctttc aaatccagtt    2100
accgtgagta gagttcttat gcaagtggga cctaagacat tggtttcttg gtttgctcat    2160
tatttcgcac tcgttgctta ctcattaggt cacgtgttgc tcagtcctct tagaggagtt    2220
gtgccatctt attcatttca gaggatgttg gatgctctcg aatacggaag tggttctgat    2280
tatagatacc atgcacctgc tggaccagca gctggtgcag ctgtttcagc aggaagaggt    2340
gctcctgtgg cagctgcatt gagtgctgca gctaggtcta ttgatggagg tgcagctact    2400
gagtctatga tggaggaga tggaggagat gcagctggaa ggctggagc agctggtaaa     2460
tctgaaggag gttcagttaa aggaagaaag gctcctaaac aacagcaacc agcagctgaa   2520
cctatgccaa tccctgttcc agtggcagct gcaactgctg cagctgcagc tatggctgct   2580
gctactatgg ttgtgggatt gcctggtatc ggacctgtta ctctcggagg cgattataag   2640
```
gatgatgatg ataagtga                                              2658

<210> SEQ ID NO 7
<211> LENGTH: 2625
<212> TYPE: DNA
<213> ORGANISM: Artificial Sequence
<220> FEATURE:
<223> OTHER INFORMATION: Synthetic construct

<400> SEQUENCE: 7

```
atggctcaaa ccatgctgct tacttcaggc gtcaccgccg ccatttttt gaggaacaag      60
agcccttggg ctcagcccaa agttcaccat ctcttcctct ctggaaactc tccggttgca     120
ctaccatcta ggagacaatc attcgttcct ctcgctctct tcgatcaagc atcttcagct     180
ggaaagagat ttgattcatt ggctgcttat ggactcgcta gggatgtttt aaccaagcag     240
gcttctaata tcgagggtaa cccaatagaa tttttggatg tgactgagaa gttctggaga     300
gctctcagga accagaaaca cgagcctgaa aagaaaggac caaaggttgt gacttatgct     360
gatgaacttt tgtttcctga ttctgcaagt tcttcaagtg cttcaacctc ttcaagtcct     420
catccacacg attacgatgt tgtgatttgt ggaggtactt taggtctttt cttggcaaca     480
gctctccagt tacaaggatg gagagttgct atagtggaga aaagacttgt tcagggtagg     540
aatcaagagt ggaatatttc ttggggagag cttgaagttt tggtggagct cggtctctta     600
tcagaagagg aattgaaagg atgcgttatt tctgagttta atccaatcag agtgggtttc     660
aagggaggtg aagatatatg gactcaagat gttcttaact tgggagtgca tcctaggaca     720
cttttggatt cacttaagag aaggttccac gctgcaggag gtattatctt cgaaaacacc     780
gcattcaaac atgctgatgt tcacccagat ggaatcaagc tctctttagc tcctggaggt     840
gctgcagctc cagttgctgt gggagataca aatagaccta acggtcttac tacaggaggt     900
gcagctcctg caccaagtgg tcctgttgct ccaagatcaa tgaccactag gctcttactt     960
gattgtatgg acattactc tgatatagtt aagcaaataa aggaagggt taaaccagat    1020
ggtatggtgt tggttgtggg aggttgcgct gagggttttc ctgcagaagc taacatctct    1080
gctgatttgc tctactctct ctcacatgct agagatgatg ttcaattatt tgggaggca    1140
ttcccagctg aaggtggtca ggctagaaca acctatatgt tcgcatactc tgatgctcac    1200
cctgataggc catcatttga ggctttactt gatacttact tccagatgct tcctgaatac    1260
caaggtattc ctcttgatca gcttaagttt aagagagttc ttttttggagg tttccctgt    1320
tactctaatg gtcctttggc caccagctttc gatagggtta tgcaaatcgg agatgcttca    1380
gcagctcagt caccattgag ttttggaggt ttcggttcta tgatgagaca tttgcctaga    1440
ctcgctaggg gattagatca ggctcttcaa gaggatagat tggctaggcc tgatcttaac    1500
tggcttcacc cttatcaacc aagtctttct gcttcatggt tgttcaaag aagtatgtct    1560
ctcgcagttg gtcaggtggc ttaccctcca gattgccctc atgcaccagc ttattacgca    1620
gctgcaaaag aggctaaggc tgcagctgca gctgcagctg ttgatagagc tgaaggattc    1680
gatggttttgg tgagtacagc aggagagagg gctctttctt tgcaagaagc agctatggag    1740
gcagttgaag ctgtggcagc tagatttgca gctggatctg cagatcctgc tgattatttc    1800
catgttgagc aggaagtgcc tggagctggt tcagatagaa ggactccaca acttgctagt    1860
ggaaaggcac agcctgctcc tccaaaattg aagaaaaagc tctttgagag agatttcagg    1920
acagctcctg aatggcaaag actcccatac acccacgtta atgagatcct tggaactaac    1980
tttggagtta tgggtgtgtt gggagataga gttttaaaac cattccttca ggatactata    2040
```

```
caactcgtgc ctctctcatt aagtatgact ggtatgatgc tttcaaatcc agttaccgtg      2100
agtagagttc ttatgcaagt gggacctaag acattggttt cttggtttgc tcattatttc      2160
gcactcgttg cttactcatt aggtcacgtg ttgctcagtc ctcttagagg agttgtgcca      2220
tcttattcat ttcagaggat gttggatgct ctcgaatacg gaagtggttc tgattataga      2280
taccatgcac ctgctggacc agcagctggt gcagctgttt cagcaggaag aggtgctcct      2340
gtggcagctg cattgagtgc tgcagctagg tctattgatg gaggtgcagc tactgagtct      2400
atggatggag gagatggagg agatgcagct ggagaggctg agcagctgg taaatctgaa      2460 ggaggttcag ttaaaggaag aaaggctcct aaacaacagc aaccagcagc tgaacctatg      2520
ccaatccctg ttccagtggc agctgcaact gctgcagctg cagctatggc tgctgctact      2580
atggttgtgg gattgcctgg tatcggacct gttactctcg atga                      2625

<210> SEQ ID NO 8
<211> LENGTH: 2652
<212> TYPE: DNA
<213> ORGANISM: Artificial Sequence
<220> FEATURE:
<223> OTHER INFORMATION: Synthetic construct

<400> SEQUENCE: 8
atggctcaaa ccatgctgct tacttcaggc gtcaccgccg ccatttttt gaggaacaag        60 agccctttgg ctcagcccaa agttcaccat ctcttcctct ctggaaactc tccggttgca      120
ctaccatcta ggagacaatc attcgttcct ctcgctctct cgatcaagc atcttcagct       180 ggaaagagat ttgattcatt ggctgcttat ggactcgcta gggatgtttt aaccaagcag      240
gcttctaata tcgagggtaa cccaatagaa ttttttggatg tgactgagaa gttctgagag     300
gctctcagga accagaaaca cgagcctgaa aagaaaggac caaaggttgt gacttatgct      360
gatgaacttt tgtttcctga ttctgcaagt tcttcaagtg cttcaacctc ttcaagtcct      420
catccacacg attacgatgt tgtgatttgt ggaggtactt taggtctttt cttggcaaca      480
gctctccagt tacaaggatg gagagttgct atagtggaga aaagacttgt tcagggtagg      540
aatcaagagt ggaatatttc ttggggagag cttgaagttt tggtggagct cggtctctta      600
tcagaagagg aattgaaagg atgcgttatt tctgagtttta atccaatcag agtgggtttc     660
aagggaggtg aagatatatg gactcaagat gttcttaact tgggagtgca tcctaggaca      720
cttttggatt cacttaagag aaggttccac gctgcaggag gtattatctt cgaaaacacc      780
gcattcaaac atgctgatgt tcacccagat ggaatcaagc tctctttagc tcctggaggt      840
gctgcagctc cagttgctgt gggagataca aatagaccta acggtcttac acaggaggt      900 gcagctcctg caccaagtgg tcctgttgct ccaagatcaa tgaccactag gctcttactt      960
gattgtatgg acattactc tgatatagtt aagcaaataa gaggaagggt taaaccagat      1020
ggtatggtgt tggttgtggg aggttgcgct gagggttttc ctgcagaagc taacatctct      1080
gctgatttgc tctactctct ctcacatgct agagatgatg ttcaattatt tgggaggca      1140 ttcccagctg aaggtggtca ggctagaaca acctatatgt tcgcatactc tgatgctcac      1200
cctgataggc catcatttga ggctttactt gatacttact tccagatgct tcctgaatac      1260
caaggtattc ctcttgatca gcttaagttt aagagagttc ttttggagg tttccccttgt      1320 tactctaatg gtccttttggc accagctttc gatagggtta tgcaaatcgg agatgcttca      1380
gcagctcagt caccattgag ttttggaggt ttcggttcta tgatgagaca tttgcctaga      1440
```

```
ctcgctaggg gattagatca ggctcttcaa gaggatagat tggctaggcc tgatcttaac    1500
tggcttcacc cttatcaacc aagtctttct gcttcatggt tgtttcaaag aagtatgtct    1560
ctcgcagttg gtcaggtggc ttaccctcca gattgccctc atgcaccagc ttattacgca    1620
gctgcaaaag aggctaaggc tgcagctgca gctgcagctg ttgatagagc tgaaggattc    1680
gatggtttgg tgagtacagc aggagagagg gctctttctt tgcaagaagc agctatggag    1740
gcagttgaag ctgtgcagc tagatttgca gctggatctg cagatcctgc tgattatttc    1800
catgttgagc aggaagtgcc tggagctggt tcagatagaa ggactccaca acttgctagt    1860
ggaaaggcac agcctgctcc tccaaaattg aagaaaaagc tctttgagag agatttcagg    1920
acagctcctg aatggcaaag actcccatac acccacgtta atgagatcct tggaactaac    1980
tttggagtta tgggtgtgtt gggagataga gttttaaaac cattccttca ggatactata    2040
caactcgtgc ctctctcatt aagtatgact ggtatgatgc tttcaaatcc agttaccgtg    2100
agtagagttc ttatgcaagt gggacctaag acattggttt cttggtttgc tcattatttc    2160
gcactcgttg cttactcatt aggtcacgtg ttgctcagtc ctcttagagg agttgtgcca    2220
tcttattcat ttcagaggat gttggatgct ctcgaatacg gaagtggttc tgattataga    2280
taccatgcac ctgctggacc agcagctggt gcagctgttt cagcaggaag aggtgctcct    2340
gtggcagctg cattgagtgc tgcagctagg tctattgatg gaggtgcagc tactgagtct    2400
atggatggag gagatggagg agatgcagct ggagaggctg agcagctgg taaatctgaa    2460 ggaggttcag ttaaaggaag aaaggctcct aaacaacagc aaccagcagc tgaacctatg    2520
ccaatccctg ttccagtggc agctgcaact gctgcagctg cagctatggc tgctgctact    2580
atggttgtgg gattgcctgg tatcggacct gttactctcg gaggcgatta taaggatgat    2640
gatgataagt ga                                                       2652

<210> SEQ ID NO 9
<211> LENGTH: 596
<212> TYPE: PRT
<213> ORGANISM: Unknown
<220> FEATURE:
<223> OTHER INFORMATION: Synechococcus sp. strain PCC7002

<400> SEQUENCE: 9

Leu Lys Val Phe Ala Trp Ala Ser Gly Phe Pro Gln Pro Gln Ser Leu
1               5                   10                  15

Cys Arg Gln Leu Lys Ser Asp Leu Glu Gln Ala Phe Pro Asn Gln Tyr
                20                  25                  30

Pro Ala Pro Pro Glu Ile Gln Pro Gly Gln Ser Ile Phe Asp Ala Leu
            35                  40                  45

Ala Ala Asp Tyr Pro Lys Thr Val Glu Tyr Phe Gln Lys Phe Pro Gln
        50                  55                  60

Gly Glu Phe Asp Leu Gln Arg Ala Tyr Trp Trp Glu Lys Arg Trp Arg
65                  70                  75                  80

Glu Thr Val Lys Asn Pro Gln Ala Pro Gln Pro Val Ile Phe Glu Lys
                85                  90                  95

Asn Gln Pro Ala Asp Pro Gln Phe Ala Gln Tyr Asp Leu Val Tyr Ile
            100                 105                 110

Gly Gly Ala Leu Gly Val Ile His Ala Ala Val Met Ala Arg Leu Gly
        115                 120                 125

Tyr Lys Val Leu Leu Ile Glu Arg Leu Pro Phe Gly Arg Met Asn Arg
    130                 135                 140
```

```
Glu Trp Asn Ile Ser Arg Ser Glu Leu Gln Ser Leu Ile Asn Leu Gly
145                 150                 155                 160
Leu Phe Asp Glu Thr Glu Ile Glu Thr Leu Val Ala Arg Glu Tyr Lys
            165                 170                 175
Asn Gly Phe Asn Lys Phe Phe Asp Gly Asn Asn Pro Ser His Leu Lys
            180                 185                 190
Ala Asn Ile Leu Tyr Thr Pro Thr Val Leu Asn Ile Ala Val Ala Ser
            195                 200                 205
Glu Leu Leu Glu Lys Cys Gly Glu Lys Leu Arg Ala Ala Gly Gly
210                 215                 220
Glu Ile Trp Asp Gln Thr Glu Phe Ile Arg Ala Asp Ile Gly Arg Glu
225                 230                 235                 240
Arg Ala Gln Ile Phe Thr Lys Ser Leu Val Thr Gly Asp Glu Lys Ile
            245                 250                 255
Val Gln Ala Arg Leu Leu Met Asp Ala Met Gly Thr Ala Ser Pro Ile
            260                 265                 270
Ala Ala Gln Leu Asn Gln Gly Arg Pro Phe Asp Ser Val Cys Pro Thr
            275                 280                 285
Val Gly Ala Val Val Lys Gly Phe Asp Pro Ala Val Trp Asp Ser Glu
290                 295                 300
Tyr Gly Asp Val Leu Asn Ser His Gly Asp Ile Ser Arg Gly Arg Gln
305                 310                 315                 320
Leu Ile Trp Glu Leu Phe Pro Gly Gln Gly Asp Glu Met Thr Ile Tyr
            325                 330                 335
Leu Phe His Tyr His Glu Val Asn Pro Glu Asn Pro Gly Ser Leu Leu
            340                 345                 350
Glu Met Tyr Glu Asp Phe Phe Ser Ile Leu Pro Glu Tyr Arg Arg Cys
            355                 360                 365
Asp Met Ala Gln Leu Thr Phe Glu Lys Ala Thr Phe Gly Tyr Ile Pro
            370                 375                 380
Gly Tyr Phe Asn Val Gly Ala Gly Asp Arg Gln Val Ala Phe Asp Arg
385                 390                 395                 400
Leu Leu Ala Ile Gly Asp Ala Ala Ser Leu Gln Ser Pro Leu Val Phe
            405                 410                 415
Thr Gly Phe Gly Ser Leu Val Arg Asn Leu Asp Arg Leu Thr Lys Leu
            420                 425                 430
Leu Asp Ile Ala Leu Gln Lys Asp Leu Leu Asp Gln Asn Leu Ser
            435                 440                 445
Lys Ile Arg Ala Tyr Gln Ser Asn Ile Ala Val Thr Trp Leu Phe Ser
450                 455                 460
Lys Gly Met Met Val Pro Thr Gly Met Lys Leu Pro Pro Gln Arg Ile
465                 470                 475                 480
Asn Ala Met Leu Asn Thr Phe Phe Gly Leu Leu Ala Asp Ser Ser Pro
            485                 490                 495
Glu Val Ala Glu Thr Phe Ile Lys Asp Arg Thr Ser Trp Leu Met Phe
            500                 505                 510
Asn Lys Leu Ala Leu Val Ala Ala Arg Gln Asn Pro Ala Leu Leu Val
            515                 520                 525
Trp Ile Trp Gln Met Ala Gly Ala Lys Asp Phe Ile Arg Trp Val Gly
            530                 535                 540
Ala Tyr Phe Ala Phe Ser Phe Asp Ala Val Leu Ser Leu Leu Leu Met
545                 550                 555                 560
Gly Trp Leu Pro Gln Trp Leu Glu Asn Ser Glu Ala Trp Leu Ser Glu
```

```
                            565                 570                 575
Lys Tyr Pro Ser Leu Trp Leu Ser Leu Leu Ser Leu Lys Tyr Arg Leu
                580                 585                 590

Thr Val Gly Thr
        595

<210> SEQ ID NO 10
<211> LENGTH: 816
<212> TYPE: PRT
<213> ORGANISM: Chlamydomonas reinhardtii

<400> SEQUENCE: 10

Ser Ala Gly Lys Arg Phe Asp Ser Leu Ala Ala Tyr Gly Leu Ala Arg
1               5                   10                  15

Asp Val Leu Thr Lys Gln Ala Ser Asn Ile Glu Gly Asn Pro Ile Glu
                20                  25                  30

Phe Leu Asp Val Thr Glu Lys Phe Trp Arg Ala Leu Arg Asn Gln Lys
            35                  40                  45

His Glu Pro Glu Lys Lys Gly Pro Lys Val Val Thr Tyr Ala Asp Glu
        50                  55                  60

Leu Leu Phe Pro Asp Ser Ala Ser Ser Ser Ala Ser Thr Ser Ser
65                  70                  75                  80

Ser Pro His Pro His Asp Tyr Asp Val Val Ile Cys Gly Gly Thr Leu
                85                  90                  95

Gly Leu Phe Leu Ala Thr Ala Leu Gln Leu Gln Gly Trp Arg Val Ala
                100                 105                 110

Ile Val Glu Lys Arg Leu Val Gln Gly Arg Asn Gln Trp Asn Ile
            115                 120                 125

Ser Trp Gly Glu Leu Glu Val Leu Val Glu Leu Gly Leu Leu Ser Glu
        130                 135                 140

Glu Leu Lys Gly Cys Val Ile Ser Glu Phe Asn Pro Ile Arg Val
145                 150                 155                 160

Gly Phe Lys Gly Gly Glu Asp Ile Trp Thr Gln Asp Val Leu Asn Leu
                165                 170                 175

Gly Val His Pro Arg Thr Leu Leu Asp Ser Leu Lys Arg Phe His
                180                 185                 190

Ala Ala Gly Gly Ile Ile Phe Glu Asn Thr Ala Phe Lys His Ala Asp
            195                 200                 205

Val His Pro Asp Gly Ile Lys Leu Ser Leu Ala Pro Gly Gly Ala Ala
        210                 215                 220

Ala Pro Val Ala Val Gly Asp Thr Asn Arg Pro Asn Gly Leu Thr Thr
225                 230                 235                 240

Gly Gly Ala Ala Pro Ala Pro Ser Gly Pro Val Ala Pro Arg Ser Met
                245                 250                 255

Thr Thr Arg Leu Leu Leu Asp Cys Met Gly His Tyr Ser Asp Ile Val
            260                 265                 270

Lys Gln Ile Arg Gly Arg Val Lys Pro Asp Gly Met Val Leu Val Val
        275                 280                 285

Gly Gly Cys Ala Glu Gly Phe Pro Ala Glu Ala Asn Ile Ser Ala Asp
    290                 295                 300

Leu Leu Tyr Ser Leu Ser His Ala Arg Asp Asp Val Gln Leu Phe Trp
305                 310                 315                 320

Glu Ala Phe Pro Ala Glu Gly Gly Gln Ala Arg Thr Thr Tyr Met Phe
                325                 330                 335
```

-continued

```
Ala Tyr Ser Asp Ala His Pro Asp Arg Pro Ser Phe Glu Ala Leu Leu
            340                 345                 350

Asp Thr Tyr Phe Gln Met Leu Pro Glu Tyr Gln Gly Ile Pro Leu Asp
        355                 360                 365

Gln Leu Lys Phe Lys Arg Val Leu Phe Gly Phe Pro Cys Tyr Ser
    370                 375                 380

Asn Gly Pro Leu Ala Pro Ala Phe Asp Arg Val Met Gln Ile Gly Asp
385                 390                 395                 400

Ala Ser Ala Ala Gln Ser Pro Leu Ser Phe Gly Phe Gly Ser Met
                405                 410                 415

Met Arg His Leu Pro Arg Leu Ala Arg Gly Leu Asp Gln Ala Leu Gln
        420                 425                 430

Glu Asp Arg Leu Ala Arg Pro Asp Leu Asn Trp Leu His Pro Tyr Gln
            435                 440                 445

Pro Ser Leu Ser Ala Ser Trp Leu Phe Gln Arg Ser Met Ser Leu Ala
        450                 455                 460

Val Gly Gln Val Ala Tyr Pro Pro Asp Cys Pro His Ala Pro Ala Tyr
465                 470                 475                 480

Tyr Ala Ala Ala Lys Glu Ala Lys Ala Ala Ala Ala Ala Val
                485                 490                 495

Asp Arg Ala Glu Gly Phe Asp Gly Leu Val Ser Thr Ala Gly Glu Arg
                500                 505                 510

Ala Leu Ser Leu Gln Glu Ala Ala Met Glu Ala Val Glu Ala Val Ala
            515                 520                 525

Ala Arg Phe Ala Ala Gly Ser Ala Asp Pro Ala Asp Tyr Phe His Val
        530                 535                 540

Glu Gln Glu Val Pro Gly Ala Gly Ser Asp Arg Arg Thr Pro Gln Leu
545                 550                 555                 560

Ala Ser Gly Lys Ala Gln Pro Ala Pro Pro Lys Leu Lys Lys Lys Leu
                565                 570                 575

Phe Glu Arg Asp Phe Arg Thr Ala Pro Glu Trp Gln Arg Leu Pro Tyr
            580                 585                 590

Thr His Val Asn Glu Ile Leu Gly Thr Asn Phe Gly Val Met Gly Val
        595                 600                 605

Leu Gly Asp Arg Val Leu Lys Pro Phe Leu Gln Asp Thr Ile Gln Leu
    610                 615                 620

Val Pro Leu Ser Leu Ser Met Thr Gly Met Met Leu Ser Asn Pro Val
625                 630                 635                 640

Thr Val Ser Arg Val Leu Met Gln Val Gly Pro Lys Thr Leu Val Ser
                645                 650                 655

Trp Phe Ala His Tyr Phe Ala Leu Val Ala Tyr Ser Leu Gly His Val
            660                 665                 670

Leu Leu Ser Pro Leu Arg Gly Val Val Pro Ser Tyr Ser Phe Gln Arg
        675                 680                 685

Met Leu Asp Ala Leu Glu Tyr Gly Ser Gly Ser Asp Tyr Arg Tyr His
    690                 695                 700

Ala Pro Ala Gly Pro Ala Ala Gly Ala Ala Val Ser Ala Gly Arg Gly
705                 710                 715                 720

Ala Pro Val Ala Ala Leu Ser Ala Ala Arg Ser Ile Asp Gly
                725                 730                 735

Gly Ala Ala Thr Glu Ser Met Asp Gly Gly Asp Gly Gly Asp Ala Ala
            740                 745                 750

Gly Glu Ala Gly Ala Ala Gly Lys Ser Glu Gly Gly Ser Val Lys Gly
```

```
                755                 760                 765
Arg Lys Ala Pro Lys Gln Gln Gln Pro Ala Ala Glu Pro Met Pro Ile
770                 775                 780

Pro Val Pro Val Ala Ala Thr Ala Ala Ala Ala Met Ala Ala
785                 790                 795                 800

Ala Thr Met Val Val Gly Leu Pro Gly Ile Gly Pro Val Thr Leu Gly
                805                 810                 815
```

<210> SEQ ID NO 11
<211> LENGTH: 827
<212> TYPE: PRT
<213> ORGANISM: Volvox carteri

<400> SEQUENCE: 11

```
Ser Thr Pro Pro Thr Gln Ser Ala Ser Ala Ala Pro Gly Leu Ala Arg
1               5                   10                  15

Thr Ile Leu Ala Gln Pro Gly Ile Glu Gly Asp Pro Leu Ala Phe Leu
            20                  25                  30

Glu Val Ser Glu Ala Tyr Trp Arg Ala Leu Arg Asn Gln Lys His Asp
        35                  40                  45

Pro Glu Arg Lys Gly Pro Ser Val Val Thr Arg Ala Asp Gly Pro Leu
    50                  55                  60

Pro Thr Pro Pro Arg Pro Ser Ser His Ala Ala Ala Gly Leu Arg Gln
65                  70                  75                  80

Gln Gln His Asp Phe Asp Val Val Ile Cys Gly Gly Thr Leu Gly Leu
                85                  90                  95

Phe Leu Ala Thr Ala Leu Gln Leu Arg Gly Trp Arg Val Ala Ile Val
            100                 105                 110

Glu Lys Arg Leu Val Gln Gly Arg Asn Gln Glu Trp Asn Ile Ser Trp
        115                 120                 125

Gly Glu Leu Glu Val Leu Val Glu Leu Gly Leu Leu Ser Arg Thr Glu
    130                 135                 140

Leu Arg Glu Ala Val Val Ser Glu Phe Asn Pro Ile Arg Val Gly Phe
145                 150                 155                 160

Gln Gly Gly Gln Asp Met Trp Thr Ser Asp Val Leu Asn Leu Gly Val
                165                 170                 175

Gln Pro Arg Arg Leu Leu Glu Ala Leu Arg Arg Phe Thr Ala Ala
            180                 185                 190

Gly Gly Ala Val Tyr Glu Asn Thr Ala Phe Arg Ala Ala Thr Ile His
        195                 200                 205

Ser Asp Gly Leu Leu Asn Leu Ser Pro Gly Gly Ser Ala Gln Pro
    210                 215                 220

Leu Ala Val Gly Asp Thr Asn Arg Pro Asn Gly Leu Asp Ala Ala Ser
225                 230                 235                 240

Ala Ser Ser Ser Arg Ala Pro Pro Ser Pro Pro Pro Arg Thr Leu
                245                 250                 255

Thr Cys Arg Leu Leu Asp Cys Met Gly His Tyr Ser Asp Ile Val
            260                 265                 270

Lys Gln Ile Arg Gly Arg Val Lys Pro Asp Gly Met Cys Met Val Val
        275                 280                 285

Gly Ser Cys Ala Glu Gly Phe Pro Pro Asp Arg Asn Gln Ser Ala Asp
    290                 295                 300

Leu Leu Tyr Ser Leu Ser His Ala Arg His Asp Leu Gln Leu Phe Trp
305                 310                 315                 320
```

-continued

Glu Ala Phe Pro Ala Glu Gly Gly Ala Ala Arg Thr Thr Tyr Met Phe
                325                 330                 335

Ala Tyr Ser Asp Ala His Pro Asp Arg Pro Thr Phe Glu Gln Leu Leu
            340                 345                 350

Asp Thr Tyr Phe Glu Met Leu Pro Glu Tyr Gln Gly Val Ser Leu Asp
        355                 360                 365

Gln Leu Arg Phe Lys Arg Val Leu Phe Gly Gly Phe Pro Cys Tyr Asn
    370                 375                 380

Asn Gly Pro Leu Pro Pro Ala Phe Asp Arg Ile Met Gln Ile Gly Asp
385                 390                 395                 400

Ala Ser Ala Ser Gln Ser Pro Leu Ser Phe Gly Gly Phe Gly Ser Met
                405                 410                 415

Met Arg His Leu Gly Arg Leu Thr Arg Gly Leu Asn Gln Ala Leu Ala
            420                 425                 430

Glu Asp Arg Leu His Gln Lys Asp Leu Ala Trp Leu Gln Pro Tyr Gln
        435                 440                 445

Pro Ser Leu Ser Ala Ser Trp Leu Phe Gln Arg Ser Met Ser Phe Cys
    450                 455                 460

Val Gly Gln Val Ser Tyr Pro Ser Ser Tyr Pro Tyr Thr Pro Pro Tyr
465                 470                 475                 480

Cys Thr Thr Asp Val Thr Leu Pro Pro Ala Leu Ala Thr Asp Ser Thr
                485                 490                 495

Glu Ser Phe Ser Asp Thr Ala Ser Ala Val Leu Val Met Gly Ala Gly
            500                 505                 510

Ala Gly Pro Ala Ala Ala Phe Gln Glu Ala Val Ala Met Ala Ala Ala
        515                 520                 525

Arg Phe Ala Ala Gly Ala Ala Asp Pro Ala Asp Tyr Phe His Glu Glu
    530                 535                 540

Pro Asp Gln Asp Met Gly Ala Ala Ala Ala Ala Ala Ala Ala Ala Thr
545                 550                 555                 560

Thr Ala Ala Ala Thr Lys Leu Ala Ala Ala Thr Thr Thr Thr Thr Thr
                565                 570                 575

Ser Gln Arg Gln Gln Pro Arg Thr Leu Phe Glu Arg Asp Phe Arg
        580                 585                 590

Arg Gly Pro Thr Trp Leu Arg Leu Pro Tyr Thr His Val Asn Glu Ile
    595                 600                 605

Leu Gly Cys Asn Phe Gly Val Met Gly Ile Leu Gly Asp Arg Val Leu
610                 615                 620

Arg Pro Phe Leu Gln Asp Thr Ile Gln Leu Val Pro Leu Ser Leu Ser
625                 630                 635                 640

Met Met Gly Met Met Leu Ala Asn Pro Val Thr Val Ser Arg Val Leu
                645                 650                 655

Leu Gln Val Gly Pro Arg Thr Leu Val Gly Trp Phe Ala His Tyr Ala
            660                 665                 670

Ala Leu Val Ala Tyr Ser Ile Ala Tyr Leu Val Leu Arg Pro Leu Arg
        675                 680                 685

Gln Leu Val Pro Tyr Tyr Ala Phe Gln Arg Leu Leu Asp Ala Leu Glu
    690                 695                 700

Tyr Gly Ser Gly Ser Asp Tyr Arg Tyr His Gly Pro Met Ser Leu Ala
705                 710                 715                 720

Ala Gly Pro Glu Gly Ala Ser Ser Ala Val Ala Gly Ser Gln Gly Ala
                725                 730                 735

Ala Ala Ala Ala Ala Ala Ala Ala Thr Ala Ala Glu Gly Ala Ala

```
              740                 745                 750
Ala Val Arg Gln Gln Met Pro Thr Ser Pro Ser Pro Lys Glu Asn Gly
            755                 760                 765

Ala Thr Asn Ser Asp Gly Asp Gly Asp Gly Pro Gly Leu Asp Val Pro
            770                 775                 780

Arg Gly Val Asp Ser Ser Val Ala Val Pro Met Ser Ala Ala Val His
785                 790                 795                 800

Thr Pro Thr Val Thr Ala Gly Ala Ala Val Ala Ala Ala Ala Ala Ala
                805                 810                 815

Ala Ala Pro His Val Glu Gly Glu Ser Arg Thr
            820                 825

<210> SEQ ID NO 12
<211> LENGTH: 563
<212> TYPE: PRT
<213> ORGANISM: Ostreococcus tauri

<400> SEQUENCE: 12

Arg Thr Ile Glu Ile Met Glu Ser Ile Ala Ser Ala Arg Asp Asp Asp
1               5                   10                  15

Asp Ala Ser Ala Ala Arg Gly Ala Gly Gly Thr Thr Thr Leu Glu Gly
            20                  25                  30

Leu Met Arg Leu Asp Ala Ala Trp Thr Ser Met Arg Arg Gly Ala Gly
            35                  40                  45

Arg Gly Asp Gly Glu Ala Phe Ala Arg Arg Arg Arg Arg Ala Ala
            50                  55                  60

Thr Glu Thr Ala Ser Asp Ala Phe Asp Val Ala Val Cys Gly Gly Thr
65                  70                  75                  80

Leu Gly Ile Leu Val Ala Cys Ala Leu Gln Arg Arg Gly Gly Arg Val
                85                  90                  95

Cys Val Ile Glu Arg Gly Glu Leu Arg Gly Arg Glu Gln Glu Trp Asn
            100                 105                 110

Val Ser Arg Ala Glu Leu Glu Ala Leu Val Arg Ala Gly Ala Leu Thr
            115                 120                 125

Ala Glu Asp Ala Asp Glu Val Thr Met Ile Glu Phe Asn Pro Ile Arg
            130                 135                 140

Cys Gly Phe His Gly Ser Glu Lys Glu Asp Ile Val Thr Arg Asp Val
145                 150                 155                 160

Leu Asn Cys Gly Val Ser Pro Ala Arg Leu Val Ala Lys Cys Arg Glu
                165                 170                 175

Arg Phe Glu Glu Ala Gly Gly Arg Val Met Glu Arg Ala Ser Leu Asn
            180                 185                 190

Gly Val Asp Val Tyr Asp Asp Cys Ala Val Leu Asp Val Asp Gly Asn
            195                 200                 205

Ala Val His Ala Arg Leu Val Leu Asp Cys Met Gly Phe Asn Ser Pro
            210                 215                 220

Ile Val Arg Gln Ile Arg Gly Gly Ala Lys Pro Asp Gly Val Cys Val
225                 230                 235                 240

Val Val Gly Thr Cys Ala Glu Gly Phe Asp Ala Ser Lys Asn Glu Ser
                245                 250                 255

Ala Asp Leu Ile Arg Thr Val Thr Asp Ile Glu Thr Asp Tyr Arg Gly
            260                 265                 270

Gln Tyr Phe Trp Glu Ala Phe Pro Ala Ser Ser Gly Pro Gly Asp Arg
            275                 280                 285
```

```
Thr Thr Tyr Met Phe Thr Tyr Met Asp Ala Glu Glu Ala Arg Pro Ser
    290                 295                 300

Ile Ala Ser Met Leu Asp Asp Tyr Trp Glu Tyr Met Pro Ala Tyr Gln
305                 310                 315                 320

Gly Leu Ser Ser Met Asp Asp Val Lys Val Lys Arg Val Leu Phe Gly
                325                 330                 335

Leu Phe Pro Thr Phe Arg Asn Ser Pro Leu Lys Thr Glu Ile Asp Arg
            340                 345                 350

Val Leu Ala Ile Gly Asp Ala Ser Gly Ile Gln Ser Pro Leu Ser Phe
        355                 360                 365

Gly Gly Leu Ala Ala Ile Leu Arg His Val Asn Arg Ile Thr Gly Ala
    370                 375                 380

Val Glu Glu Ala Leu Asp Ala Asn Ala Leu Asp Arg Asp Ala Leu Arg
385                 390                 395                 400

Ser Ile Asn Ala Tyr Gln Pro Ala Leu Ser Ala Ala Trp Leu Phe Gln
                405                 410                 415

Arg Cys Met Ser Val Arg Ile Gly Ala Lys Pro Lys Arg Asp Phe Ile
            420                 425                 430

Asn Arg Leu Met Thr Thr Asn Phe Gly Val Met Glu Ala Leu Gly Glu
        435                 440                 445

Asp Val Met Arg Pro Phe Leu Gln Asp Val Val Thr Phe Lys Gly Leu
450                 455                 460

Gly Lys Thr Leu Val Ser Met Thr Ala Ser Lys Pro Leu Phe Val Pro
465                 470                 475                 480

Glu Ile Leu Ile Asn Ala Gly Pro Gly Pro Ile Ala Asp Trp Phe Arg
                485                 490                 495

His Phe Ile Ala Leu Gly Met Tyr Asp Leu Leu Ser Ser Pro Ala Gly
            500                 505                 510

Ala Val Ala His Ala Leu Arg Pro Ala Gly Gln Asp Glu Ser Asn Ala
        515                 520                 525

Asn Pro Leu Val Glu Ala Val Ser Gly Ser Leu Ser Pro Arg Gln Lys
    530                 535                 540

Phe Phe Ile Arg Arg His Ala Glu Ala Val Ile Tyr Gly Cys Gly Arg
545                 550                 555                 560

Asp Ala His
```

```
<210> SEQ ID NO 13
<211> LENGTH: 513
<212> TYPE: PRT
<213> ORGANISM: Unknown
<220> FEATURE:
<223> OTHER INFORMATION: Synechococcus sp. strain PCC7002

<400> SEQUENCE: 13

Met Gly Gln Val Lys Thr Ile Leu Gly Ala Met Pro Gly Asp Pro Leu
1               5                   10                  15

Lys Gly Leu Arg Ala Ala Asp Gln Arg Trp Gln Asn Trp Arg Gln Gly
            20                  25                  30

Lys Ile Gly Ala Pro Ala Met Val Gln Ile Gly Thr Glu Asp Cys Pro
        35                  40                  45

Asp Tyr Asp Cys Asp Val Leu Val Cys Gly Gly Thr Leu Gly Leu Leu
    50                  55                  60

Leu Ala Ala Ala Leu Gln Arg Arg Gly Trp Arg Val Ile Ile Leu Glu
65                  70                  75                  80

Arg Gly Pro Leu Gln Gly Arg Val Gln Glu Trp Asn Ile Ser Arg Ser
```

```
                    85                  90                  95
Glu Leu Gln Thr Leu Leu Asp Leu Glu Leu Leu Ser Glu Thr Glu Leu
                100                 105                 110

Arg Glu Val Ile Ala Thr Glu Phe Asn Pro Leu Arg Ile Gln Phe His
            115                 120                 125

Gly Gly Asp Pro Leu Trp Val Lys Asp Ile Leu Asn Ile Gly Val Ser
130                 135                 140

Pro Arg Arg Leu Leu Ala Val Leu Lys Glu Lys Phe Leu Thr Trp Gly
145                 150                 155                 160

Gly Lys Ile Phe Glu Asn His Pro Cys Thr Gly Ile Thr Val Ser Pro
                165                 170                 175

Gln Gly Ala Ile Ala Arg Thr Glu Lys Phe Thr Phe His Thr Arg Leu
                180                 185                 190

Ile Leu Asp Gly Met Gly His Phe Ser Pro Ile Ala Gln Gln Val Arg
            195                 200                 205

Gln Gly Gln Lys Pro Asp Gly Val Cys Leu Val Val Gly Ser Cys Ala
        210                 215                 220

Gln Gly Phe Ala Ala Asn Ser Lys Gly Asp Leu Ile Tyr Ser Phe Thr
225                 230                 235                 240

Pro Ile Arg Asn Gln Cys Gln Tyr Phe Trp Glu Ala Phe Pro Ala His
                245                 250                 255

Asp Gly Arg Thr Thr Tyr Leu Phe Thr Tyr Leu Asp Ala His Pro Gln
                260                 265                 270

Arg Phe Asp Leu Ala Phe Leu Leu Glu Glu Tyr Leu Lys Leu Leu Pro
            275                 280                 285

Asp Tyr Gln Gln Val Asp Leu Ala Ala Leu Asp Phe Gln Arg Phe Leu
        290                 295                 300

Phe Gly Phe Phe Pro Ser Tyr Arg Arg Ser Pro Leu His Tyr Pro Trp
305                 310                 315                 320

Asp Arg Ile Leu Pro Ile Gly Asp Ser Ser Gly Gly Gln Ser Pro Val
                325                 330                 335

Ser Phe Gly Gly Phe Gly Ala Met Leu Arg His Leu Glu Arg Leu Thr
                340                 345                 350

Asn Gly Leu Asp Asp Ala Leu Thr Gln Asp Cys Cys Asp Arg Gln Ser
            355                 360                 365

Leu Ala Gln Leu Gln Pro Tyr Gln Pro Asn Leu Ser Val Thr Trp Leu
        370                 375                 380

Phe Gln Lys Ala Met Ser Val Gly Val Asn Gln Ser Cys Pro Pro Asn
385                 390                 395                 400

Gln Ile Asn Asp Leu Leu Asn Ala Val Phe Gly Val Met Ala Gln Leu
                405                 410                 415

Gly Glu Asp Thr Leu Asn Pro Phe Leu Gln Asp Val Val Gln Phe Gln
                420                 425                 430

Gly Leu Thr Lys Thr Leu Pro Arg Val Asn Phe Lys Thr Val Leu Pro
            435                 440                 445

Leu Leu Pro His Leu Gly Val Gly Ala Leu Ala Asp Trp Leu Arg His
        450                 455                 460

Tyr Leu Ala Leu Gly Leu Tyr Thr Ser Ser Tyr Ala Leu Ser Gln Arg
465                 470                 475                 480

Leu Pro Met Gly Asp Ser Tyr Gln Ala Lys Arg Arg Glu Ala Trp
                485                 490                 495

Gln Tyr Gly Ser Gly Gln Asp Phe His Gln Ala Gly Leu Thr Glu Gln
                500                 505                 510
```

Asp

<210> SEQ ID NO 14
<211> LENGTH: 577
<212> TYPE: PRT
<213> ORGANISM: Chlamydomonas reinhardtii

<400> SEQUENCE: 14

```
Arg Glu Gly Ile Arg Gln Arg Ser Val Ala Ala Asn Ala Gln Ala Ala
1               5                   10                  15

Gly Ala Gly Gly Arg Thr Thr Tyr Ala Ala Phe Lys Ala Ala Asp Glu
            20                  25                  30

Gln Trp Leu Lys Leu Arg Thr Gln Pro Glu Gly Glu Ala Ala Gly Pro
        35                  40                  45

Ala Pro Thr Phe Val Thr Glu Ser Ala Gln Pro Leu Pro Ala Ala Pro
    50                  55                  60

Gln Tyr Asp Val Val Cys Gly Gly Thr Leu Gly Ile Phe Ala Ala
65                  70                  75                  80

Ala Ala Leu Ala Ala Arg Gly Leu Arg Val Ala Val Glu Arg Gly
                85                  90                  95

Pro Leu Arg Gly Arg Ala Gln Glu Trp Asn Ile Ser Arg Lys Glu Leu
            100                 105                 110

Tyr Glu Leu Glu His Val Gly Val Ala Ser Arg Glu Glu Leu Glu Ala
        115                 120                 125

Cys Val Ala Ile Glu Phe Asn Pro Val Arg Ile Gly Phe Ala Trp Asp
    130                 135                 140

Leu Ser Pro Ala Thr Phe Ser Ala Ala Ser Ala Ser Thr Ser Ser
145                 150                 155                 160

Arg Leu Thr Glu Val Trp Thr Arg Asp Val Leu Asn Leu Gly Val Arg
                165                 170                 175

Pro Asp Ala Leu Val Gln Leu Met Arg Ala Lys Leu Glu Ala Ala Gly
            180                 185                 190

Gly Ala Val Ile Glu Gln Ala Ala Leu Ala Gly Ile Ser Val His Pro
        195                 200                 205

Asn Gly Cys Ser Leu Asp Val Lys Thr Asp Ser Gly Ala Gly Ala Gly
    210                 215                 220

Ala Ala Ala Ala Arg Leu Thr Ala Arg Leu Val Val Asp Cys Met Gly
225                 230                 235                 240

His Phe Ser Pro Ile Val Arg Gln Val Arg Trp Gly Thr Lys Pro Asp
                245                 250                 255

Gly Val Cys Leu Val Val Gly Thr Cys Gly Ser Gly Phe Ala Pro Gly
            260                 265                 270

Asn Asn Thr Thr Ala Asp Val Ile Leu Thr Asn Thr Pro Leu Gln Pro
        275                 280                 285

Ala Glu Ala Ala Phe Asn Arg Ala Gln Tyr Phe Trp Glu Ala Phe Pro
    290                 295                 300

Ala Ala Ser Gly Pro Ser Asp Arg Thr Thr Tyr Met Phe Thr Tyr Ile
305                 310                 315                 320

Asp Ala Ala Pro Tyr Arg Lys Pro Leu Ala Ala Met Met Asp Asp Tyr
                325                 330                 335

Trp Arg Leu Met Pro Gln Tyr Gln Gly Val Arg Leu Glu Asp Ile Thr
            340                 345                 350

Phe Lys Arg Val Leu Phe Gly Phe Phe Pro Thr Phe Lys Asp Thr Pro
        355                 360                 365
```

```
Leu Arg Pro Ala Phe Asp Arg Ile Gln Ile Gly Asp Ala Ser Gly
        370                 375                 380

Leu Gln Ser Pro Leu Ser Phe Gly Gly Phe Gly Ala Leu Thr Arg His
385                 390                 395                 400

Leu Ala Arg Leu Thr Asn Ala Leu Thr Glu Ala Ala Glu Ala Asp Ala
                405                 410                 415

Leu Asp Arg Asn Ser Leu Gly Leu Ile His Ala Tyr Asn Pro Gly Leu
                420                 425                 430

Ser Ser Ser Trp Met Met Gln Lys Ala Met Ser Val Arg Glu Gly Asp
                435                 440                 445

Lys Pro Pro Glu Leu Ile Asn Arg Met Leu Ala Gly Asn Phe Arg
450                 455                 460

Ala Met Glu Lys Leu Gly Glu Ala Thr Met Lys Pro Phe Leu Gln Asp
465                 470                 475                 480

Val Ile Gln Phe Gln Pro Met Leu Ala Thr Met Gly Ala Gln Ile Leu
                485                 490                 495

Thr Asp Pro Leu Ser Val Pro Ser Leu Met Ala His Val Gly Pro Gly
                500                 505                 510

Pro Leu Ala Glu Trp Leu Gly His Met Ala Asn Leu Gly Ala Tyr Thr
            515                 520                 525

Ala Leu His Gly Ala Gly Ala Ala Gly Leu Arg Ala Ala Leu Ala
            530                 535                 540

Pro Gly Gly Ala Ala Gly Leu Pro Ala Arg Ala Arg Phe Ala Leu
545                 550                 555                 560

Gly Arg Leu Leu Asp Ala Trp Glu Tyr Gly Ser Gly Lys Asp Tyr Lys
                565                 570                 575

Leu

<210> SEQ ID NO 15
<211> LENGTH: 500
<212> TYPE: PRT
<213> ORGANISM: Volvox carteri

<400> SEQUENCE: 15

Gly Thr Pro Ser Gly Pro Ala Ala Pro Lys Phe Ile Ser Glu Ser Ser
1               5                   10                  15

Glu Pro Leu Gln Thr Ser Pro Glu Phe Asp Val Val Cys Gly Gly
            20                  25                  30

Thr Leu Gly Ile Phe Ala Ala Ala Leu Ala Leu Arg Gly Leu Arg
            35                  40                  45

Val Ala Val Leu Glu Arg Gly Pro Leu Arg Gly Arg Ala Gln Glu Trp
50                  55                  60

Asn Ile Ser Arg Lys Glu Leu Leu Glu Leu Ser Val Gly Val Ala
65                  70                  75                  80

Thr Arg Glu Glu Leu Glu Ala Cys Val Ala Ile Glu Val Arg Lys Leu
                85                  90                  95

Cys Ser Ile Ser Gly Leu Ser Glu Val Trp Thr Arg Asp Ile Leu Asn
                100                 105                 110

Leu Gly Val Ser Pro Asn Ala Leu Val Gly Leu Met Arg Arg Lys Leu
            115                 120                 125

Glu Glu Gln Gly Gly Val Val Leu Glu Arg Thr Ala Leu Glu Gly Val
        130                 135                 140

Ala Ala Arg Arg Asp Asp Asp Asp Gly Ser Pro Ala Ala Ala Thr
145                 150                 155                 160
```

```
Val Thr Ala Arg Leu Val Val Asp Cys Met Gly His Phe Ser Pro Ile
            165                 170                 175

Val Arg Gln Val Arg Arg Gly Ala Lys Pro Asp Gly Val Cys Leu Val
        180                 185                 190

Val Gly Thr Met Gly Ser Gly Phe Thr Asn Asn Thr Thr Ala Asp Val
    195                 200                 205

Ile Leu Thr Ser Thr Pro Leu Gln Pro Glu Asp Ala Lys Ala Gln Tyr
210                 215                 220

Phe Trp Glu Ala Phe Pro Ala Ala Ser Gly Pro Thr Asp Arg Thr Thr
225                 230                 235                 240

Tyr Met Phe Thr Tyr Leu Thr Ala Asp Asp Tyr Arg Pro Pro Leu Ala
                245                 250                 255

Ala Met Met Glu Asp Tyr Trp Arg Leu Met Pro Gln Tyr Gln Gly Val
            260                 265                 270

Arg Leu Glu Asp Ile Thr Phe Lys Arg Val Leu Phe Gly Met Phe Pro
        275                 280                 285

Thr Phe Lys Asp Thr Pro Leu Arg Pro Ala Tyr Asp Arg Val Ile Gln
    290                 295                 300

Ile Gly Asp Ala Ser Gly Leu Gln Ser Pro Leu Ser Phe Gly Gly Phe
305                 310                 315                 320

Gly Ala Leu Thr Arg His Leu Ala Arg Leu Thr Ala Ala Leu Thr Glu
                325                 330                 335

Ala Val Glu Ala Asp Ala Leu Asp Arg Gly Ser Leu Ser Leu Val Gln
            340                 345                 350

Ser Tyr Asn Pro Gly Leu Ser Ser Ser Trp Met Met Gln Lys Ala Met
        355                 360                 365

Ser Val Arg Arg Gly Glu Gln Pro Pro Asp Leu Ile Asn Arg Met
    370                 375                 380

Leu Ala Gly Asn Phe Lys Ala Met Glu Arg Leu Gly Asp Pro Val Met
385                 390                 395                 400

Lys Pro Phe Leu Gln Asp Val Val Gln Phe Gly Pro Met Met Arg Thr
                405                 410                 415

Met Ala Ala Gln Ile Leu Thr Asp Pro Ala Ser Ile Pro Ser Leu Ile
            420                 425                 430

Arg His Val Gly Pro Ala Pro Leu Leu Glu Trp Leu Ser His Met Ala
        435                 440                 445

Asn Leu Ala Ala Tyr Thr Ala Leu His Gly Ala Ala Ser Met Ala Asp
    450                 455                 460

Leu Arg Thr Ala Val Ser Gly Ala Ala Val Leu Thr Pro Arg Glu Arg
465                 470                 475                 480

Phe Ala Leu Asn Arg Leu Leu Asp Ala Trp Glu Tyr Gly Ser Gly Met
                485                 490                 495

Asp Tyr Lys Leu
            500

<210> SEQ ID NO 16
<211> LENGTH: 544
<212> TYPE: PRT
<213> ORGANISM: Physcomitrella patens

<400> SEQUENCE: 16

Arg Thr Gln Arg Ile Met Glu Asn Ile Pro Gly Ser Ala Glu Ala Gly
1               5                   10                  15

Gly Ala Gly Gly Ala Met Ser Tyr Gln Ala Leu Lys Arg Leu Asp Glu
```

His Trp Arg Lys Leu Lys Ala Arg Thr Pro Met Thr Gly Pro Ala Pro
             20                  25                  30
             35                  40                  45

Glu Val Val Thr Arg Arg Gln Gly Lys Trp Ala Asp Ser Gly Leu Ala
 50                  55                  60

Asp Arg Ser Gln Ala Val Phe Asp Val Val Cys Gly Gly Thr Leu
 65                  70                  75                  80

Gly Val Phe Leu Ala Thr Ala Leu Ala Leu Arg Gly Leu Lys Val Ala
                 85                  90                  95

Ile Ile Glu Arg Gly Pro Leu Arg Gly Arg Val Gln Asp Trp Asn Val
             100                 105                 110

Ser Arg Lys Glu Leu Lys Glu Leu Val Tyr Ala Gly Val Leu Thr Glu
             115                 120                 125

Asp Glu Ile Glu Glu Val Ile Ser Ile Glu Phe Asn Pro Ser Arg Val
             130                 135                 140

Gly Phe Ala Gly Gly Thr Glu Leu Trp Val Asn Asp Ile Leu Asn Leu
145                 150                 155                 160

Gly Val Ser Pro Ala Lys Leu Ile Glu Val Cys Lys Lys Arg Phe Val
                 165                 170                 175

Asp Val Gly Gly Glu Val Leu Glu Phe Thr Gly Leu Ser Lys Leu Asp
             180                 185                 190

Val Phe Asn Asp Gly Ala Val Val Ser Leu Asp Asn Gly Lys Thr Leu
             195                 200                 205

Val Gly Arg Leu Leu Leu Asp Val Met Gly Asn Gln Ser Pro Ile Val
             210                 215                 220

Arg Gln Ile Arg Trp Gly Gln His Pro Asp Gly Val Cys Leu Val Val
225                 230                 235                 240

Gly Ala Cys Ala Arg Gly Phe Glu Asn Asn Ser Thr Ser Asp Leu Ile
                 245                 250                 255

Tyr Thr Asn Thr Gln Val Thr Gln Val Gly Ser Ser Lys Thr Gln Tyr
             260                 265                 270

Phe Trp Glu Ala Phe Pro Ala Gly Ser Gly Pro Thr Asp Arg Thr Thr
             275                 280                 285

Tyr Met Phe Ser Tyr Leu Asp Ala Thr Pro Ser Arg Pro Leu Leu Glu
             290                 295                 300

Glu Met Leu Glu Asp Tyr Trp Asp Leu Met Pro Asp Tyr Gln Gly Val
305                 310                 315                 320

Lys Leu Glu Asp Leu Glu Ile Arg Arg Val Leu Phe Gly Cys Phe Pro
                 325                 330                 335

Thr Tyr Arg Ala Ser Pro Leu Pro Ser Ala Phe Asp Arg Val Leu Gln
             340                 345                 350

Ile Gly Asp Ala Ser Gly Ile Gln Ser Pro Ile Ser Phe Gly Phe
             355                 360                 365

Gly Ala Ile Thr Arg His Ile Gly Arg Leu Ser Asn Gly Leu Tyr Asp
             370                 375                 380

Ala Leu Gln Ala Asp Leu Leu Asp Lys Asn Asn Leu Ala Leu Leu Asn
385                 390                 395                 400

Pro Tyr Leu Pro Asn Leu Ser Gly Val Trp Met Tyr Gln Arg Ala Met
                 405                 410                 415

Ser Val Arg Leu Asp Ile Glu Ser Pro Pro Asp Phe Ile Asn Asn Leu
             420                 425                 430

Leu Ser Ile Asn Phe Glu Cys Met Glu Arg Leu Gly Asp Pro Val Val
             435                 440                 445

```
Arg Pro Phe Leu Gln Asp Val Gln Phe Trp Pro Gln Val Arg Leu
    450                 455                 460

Leu Ser Leu Ile Met Leu Thr Lys Pro Leu Phe Ile Pro Gln Ile Phe
465                 470                 475                 480

Arg Gln Val Gly Phe Phe Pro Leu Ile Asp Trp Phe Arg His Phe Ile
                    485                 490                 495

Ala Leu Ala Met Tyr Thr Leu Leu Trp Leu Ala Leu Ser Gly Ser Pro
                500                 505                 510

Arg Thr Trp Val Asn Ser Leu Pro Lys Glu Lys Gln Phe Val Trp Arg
            515                 520                 525

Arg Arg Phe Glu Ala Trp Gln Tyr Gly Ser Gly Leu Asp Tyr His Pro
530                 535                 540
```

<210> SEQ ID NO 17
<211> LENGTH: 544
<212> TYPE: PRT
<213> ORGANISM: Arabidopsis thaliana

<400> SEQUENCE: 17

```
Leu Thr Gln Lys Ile Met Glu Ser Ile Ser Val Gly Gly Glu Ala Gly
1               5                   10                  15

Gly Ala Gly Gly Ala Tyr Ser Tyr Asn Ala Leu Lys Arg Leu Asp Asn
                20                  25                  30

Ile Trp Ser Asn Ile Cys Thr Gln Pro Thr Gly Pro Gln Glu Thr Gln
            35                  40                  45

Gln Ile Val Ser Arg Val Ser Gly Phe Ser Gln Asp Tyr Ser Met Gly
        50                  55                  60

Asn Asn Leu Val Gly Thr Phe Asp Ile Val Cys Gly Gly Thr Leu
65                  70                  75                  80

Gly Ile Phe Leu Ala Thr Ala Leu Cys Ala Lys Gly Leu Arg Val Ala
                85                  90                  95

Val Val Glu Arg Asn Ala Ile Lys Gly Arg Asp Gln Glu Trp Asn Ile
                100                 105                 110

Ser Arg Lys Glu Met Lys Glu Leu Thr Glu Val Arg Val Leu Thr Glu
            115                 120                 125

Asp Glu Ile Glu Glu Val Ile Ala Ala Lys Phe Asn Pro Asn Arg Cys
        130                 135                 140

Gly Phe Glu Asn Leu Gly Asp Ile Trp Val Glu Asp Ile Leu Asn Leu
145                 150                 155                 160

Gly Val Ser Pro Ala Lys Leu Val Glu Thr Val Lys Gln Arg Phe Ile
                165                 170                 175

Ser Leu Gly Gly Val Ile Leu Glu Asp Ser Ser Leu Ser Ser Ile Val
                180                 185                 190

Ile Tyr Asn Asp Leu Ala Val Met Gln Leu Ser Lys Gly Asp Thr Leu
            195                 200                 205

Ser Ser Arg Leu Val Ile Asp Ala Met Gly Asn Phe Ser Pro Ile Leu
        210                 215                 220

Lys Gln Ile Lys Arg Gly Arg Lys Pro Asp Gly Met Cys Leu Val Val
225                 230                 235                 240

Gly Ser Cys Ala His Gly Phe Lys Glu Asn Ser Ser Asp Val Ile
                245                 250                 255

Tyr Ser Ser Ser Ser Val Thr Arg Val Ala Asp Ser Asn Val Gln Leu
                260                 265                 270

Phe Trp Glu Ala Phe Pro Ala Gly Ser Gly Pro Leu Asp Arg Thr Thr
```

```
            275                 280                 285
Tyr Met Phe Thr Tyr Thr Glu Pro Gln Ser Thr Ser Pro Ser Leu Glu
    290                 295                 300

Asp Leu Leu Glu Glu Tyr Trp Lys Leu Met Pro Lys Tyr Gln Gly Val
305                 310                 315                 320

Ser Leu Asp Glu Leu Glu Ile Leu Arg Val Val Tyr Gly Ile Phe Pro
                325                 330                 335

Thr Tyr Arg Asn Ser Pro Leu Pro Ala Ala Phe Asp Arg Val Leu Gln
            340                 345                 350

Phe Gly Asp Ala Ser Gly Ile Gln Ser Pro Val Ser Phe Gly Gly Phe
        355                 360                 365

Gly Ser Leu Thr Arg His Leu Gly Arg Leu Ser Asn Gly Ile Tyr Asp
    370                 375                 380

Ala Ile Asp Gly Asp Leu Leu Asp Ser Asp Ser Leu Ser Lys Leu Asn
385                 390                 395                 400

Pro Tyr Met Pro Asn Leu Ser Ala Ser Trp Leu Phe Gln Arg Ala Met
                405                 410                 415

Ser Ala Lys Gln Gln Leu Asp Val Ser Arg Gly Phe Thr Asn Glu Leu
            420                 425                 430

Leu His Val Asn Phe Ser Cys Met Gln Arg Leu Gly Asp Pro Val Leu
        435                 440                 445

Arg Pro Phe Leu Gln Asp Ile Ile Gln Phe Gly Pro Leu Ala Lys Thr
    450                 455                 460

Leu Gly Leu Val Met Leu Thr Lys Pro Gln Ile Ile Pro Ser Ile Phe
465                 470                 475                 480

Arg Gln Val Gly Ile Pro Val Leu Leu Asp Trp Ser Val His Phe Phe
                485                 490                 495

Met Leu Gly Leu Tyr Thr Leu Leu Ser Ala Tyr Ile Asp Pro Leu Leu
            500                 505                 510

Arg Pro Ser Leu Glu Gly Leu Pro Ser Lys Thr Arg Phe Glu Trp Lys
        515                 520                 525

Arg Cys Leu Glu Ala Trp Lys Tyr Gly Ala Gly Leu Asp Tyr Glu Leu
    530                 535                 540

<210> SEQ ID NO 18
<211> LENGTH: 22
<212> TYPE: DNA
<213> ORGANISM: Artificial Sequence
<220> FEATURE:
<223> OTHER INFORMATION: Synthetic construct

<400> SEQUENCE: 18
cttggcggaa gcagagtatg gc                                        22

<210> SEQ ID NO 19
<211> LENGTH: 23
<212> TYPE: DNA
<213> ORGANISM: Artificial Sequence
<220> FEATURE:
<223> OTHER INFORMATION: Synthetic construct

<400> SEQUENCE: 19
cggcctccct tcatccctcc cac                                       23

<210> SEQ ID NO 20
<211> LENGTH: 15
<212> TYPE: PRT
<213> ORGANISM: Chlamydomonas reinhardtii
```

```
<400> SEQUENCE: 20

Cys Leu Arg Asn Gln Lys His Glu Pro Glu Lys Lys Gly Pro Lys
1               5                   10                  15
```